US010351917B2

(12) United States Patent
Concibido et al.

(10) Patent No.: US 10,351,917 B2
(45) Date of Patent: Jul. 16, 2019

(54) MOLECULAR MARKERS ASSOCIATED WITH SOYBEAN TOLERANCE TO LOW IRON GROWTH CONDITIONS

(75) Inventors: Vergel C. Concibido, St. Louis, MO (US); Susannah G. Cooper, St. Louis, MO (US); David Hoffman, St. Louis, MO (US); Hongwu Jia, St. Louis, MO (US); Thomas Jury, Madison, WI (US); Bradley LaVallee, St. Louis, MO (US); Roger L. Lussenden, Redwood Falls, MN (US); Xianghai Ye, Ankeny, IA (US)

(73) Assignee: Monsanto Technology LLC, St. Louis, MO (US)

( * ) Notice: Subject to any disclaimer, the term of this patent is extended or adjusted under 35 U.S.C. 154(b) by 1393 days.

(21) Appl. No.: 14/240,895

(22) PCT Filed: Aug. 29, 2012

(86) PCT No.: PCT/US2012/052871
§ 371 (c)(1),
(2), (4) Date: May 15, 2014

(87) PCT Pub. No.: WO2013/033221
PCT Pub. Date: Mar. 7, 2013

(65) Prior Publication Data
US 2014/0304860 A1 Oct. 9, 2014

Related U.S. Application Data

(60) Provisional application No. 61/529,838, filed on Aug. 31, 2011.

(51) Int. Cl.
| C12Q 1/68 | (2018.01) |
| A01H 1/04 | (2006.01) |
| A01H 6/54 | (2018.01) |
| C12Q 1/6895 | (2018.01) |
| A01H 5/10 | (2018.01) |
| C07K 14/415 | (2006.01) |

(52) U.S. Cl.
CPC ............ C12Q 1/6895 (2013.01); A01H 1/04 (2013.01); A01H 6/542 (2018.05); A01H 5/10 (2013.01); C07K 14/415 (2013.01); C12Q 2600/156 (2013.01)

(58) Field of Classification Search
None
See application file for complete search history.

(56) References Cited

U.S. PATENT DOCUMENTS

| 6,207,367 | B1 | 3/2001 | Helentjaris et al. |
| 6,399,855 | B1 | 6/2002 | Beavis |
| 6,959,617 | B2 | 11/2005 | Deppermann |
| 7,134,351 | B2 | 11/2006 | Deppermann |
| 7,454,989 | B2 | 11/2008 | Deppermann |
| 7,502,113 | B2 | 3/2009 | Deppermann et al. |
| 7,591,101 | B2 | 9/2009 | Deppermann |
| 7,611,842 | B2 | 11/2009 | Deppermann et al. |
| 7,685,768 | B2 | 3/2010 | Deppermann |
| 7,977,533 | B2 | 7/2011 | Sebastian et al. |
| 9,458,504 | B1 * | 10/2016 | Hamilton ............. C12Q 1/6881 |
| 2005/0015827 | A1 | 1/2005 | Podlich et al. |
| 2005/0204780 | A1 | 9/2005 | Moridaira et al. |
| 2005/0216545 | A1 | 9/2005 | Aldrich et al. |
| 2005/0218305 | A1 | 10/2005 | Tsukamoto et al. |
| 2006/0041951 | A1 | 2/2006 | Sebastian et al. |
| 2006/0042527 | A1 | 3/2006 | Deppermann |
| 2006/0046244 | A1 | 3/2006 | Deppermann |
| 2006/0046264 | A1 | 3/2006 | Deppermann et al. |
| 2006/0048247 | A1 | 3/2006 | Deppermann |
| 2006/0048248 | A1 | 3/2006 | Deppermann |
| 2006/0050453 | A1 | 3/2006 | Duvvury et al. |
| 2007/0204366 | A1 | 8/2007 | Deppermann et al. |
| 2007/0207485 | A1 | 9/2007 | Deppermann et al. |
| 2009/0025288 | A1 | 1/2009 | Deppermann et al. |
| 2009/0036308 | A1 | 2/2009 | Guida, Jr. et al. |
| 2009/0215060 | A1 | 8/2009 | Deppermann et al. |
| 2010/0086963 | A1 | 4/2010 | Deppermann et al. |
| 2010/0099859 | A1 | 4/2010 | Malven et al. |
| 2010/0275286 | A1 * | 10/2010 | Wu .......................... A01H 1/02 800/260 |

OTHER PUBLICATIONS

Charlson et al. (IDS, Journal of Plant Nutrition; vol. 26, Nos. 10 and 11, pp. 2267-2276, (2003)).*
Wang et al. (Theoretical and Applied Genetics, May 2008).*
soybase.org accessd on Sep. 17, 2017.*
Naeve et al. (Agron. J. 98: pp. 808-814 (2006)).*
Funke et al. (Plant Molecular Biology 22: pp. 37-446, (1993)).*
Jun et al. (Euphytica, (2008) 162: pp. 179-191).*
Wu et al. Table 1 from US 2010/0275286 (Oct. 28, 2010).*
Cregan et al. Crop Science 39: 1464-1490 (1999).*
Orf et al. Crop Science 39: 1642-1651 (1999).*
Mansur et al. Crop Science 36: 1327-1336 (1996).*
Marker Satt449 location from SoyBase Composite Map (2003).*
Song et al. Theoretical and Applied Genetics 109(1): 122-128 (Jun. 2004).*
Marker AZ536570 location from SoyBase Composite Map (2003).*
King, "Mineral Evaluation and Quantitative Trait Loci Mapping in a Soybean (*Glycine max* (L.) Merr.) Population Developed for Iron Deficiency Chlorosis Resistance", Graduate Theses and Dissertations, Paper 10298. Iowa State University. 2011 (available online at <http://lib.dr.iastate.edu>).*

(Continued)

*Primary Examiner* — David T Fox
(74) *Attorney, Agent, or Firm* — Thompson Coburn LLP; William A. Holtz; Lawrence M. Lavin, Jr.

(57) ABSTRACT

The present invention provides methods and compositions for identifying soybean plants that are tolerant or have improved tolerance, or those that are susceptible to, iron deficient growth conditions. The methods use molecular markers to identify, select, and/or introgress genetic loci modulating phenotypic expression of an iron deficiency tolerance trait in soybean plant breeding. Methods are provided for screening germplasm entries for the performance and expression of this trait.

4 Claims, No Drawings
Specification includes a Sequence Listing.

(56) References Cited

OTHER PUBLICATIONS

GenBank Accession No. HR127164. GF_Ba Glycine falcata genomic 3-, genomic survey sequence. Oct. 25, 2010 [retrieved Jan. 14, 2013] Retrieved from the internet: <URL: http://www.ncbi.nlm.nih.gov/nucgss/HR127164>.

Foster-Hartnett et al., "Comparative Genomic Analysis of Sequences Sampled from a Small Region on Soybean (*Glycine max*) Molecular Linkage Group G", Genome, 2002, pp. 634-645, vol. 45, No. 4.

Borevitz et al., "Large-Scale Indentification of Single-Feature Polymorphisms in Complex Genomes", Genome Research, Mar. 2003, pp. 513-523, vol. 13 No. 3.

Charlson et al., "Associating SSR Markers with Soybean Resistance to Iron Chlorosis", Journal of Plant Nutrition, 2003, pp. 2267-2276, vol. 26 No. 10 and 11.

Choi et al., "A Soybean Transcript Map: Gene Distribution, Haplotype and Single-Nucleotide Polymorphism Analysis", Genetics, May 2007, pp. 685-696, vol. 176 No. 1.

Dahiya et al., "Effect of Salinity, Alkalinity and Iron Sources on Availability of Iron", Plant and Soil, 1979, pp. 13-18, vol. 51.

Diers et al., "Possible Identification of Quantitative Trait Loci Affecting Iron Efficiency in Soybean", Journal of Plant Nutrition, 1992, pp. 2127-2136, vol. 15.

Gonzalez-Vallejo et al., "Iron Deficiency Decreases the Fe(III)-Chelate Reducing Activity of Leaf Protoplasts", Plant Physiology, 2000, pp. 337-344, vol. 122 No. 2.

Goos et al., "Seed Treatment, Seeding Rate, and Cultivar Effects on Iron Deficiency Chlorosis of Soybean", Journal of Plant Nutrition, 2001, pp. 1255-1268, vol. 24 No. 8.

Goos et al., "A Comparison of Three Methods for Reducing Iron-Deficiency Chlorosis in Soybean", Agronomy Journal, 2000, pp. 1135-1139, vol. 92.

Hintz et al., "Population Development for the Selection of High-Yielding Soybean Cultivars with Resistance to Iron-Deficiency Chlorosis", Crop Science, 1987, pp. 707-710, vol. 27.

Hyten et al., "A High Density Integrated Genetic Linkage Map of Soybean and the Development of a 1536 Universal Soy Linkage Panel for Quantitative Trait Locus Mapping", Crop Science, May 2010, pp. 960-968, vol. 50 No. 3.

Hyten et al., "High-Throughput SNP Discovery and Assay Development in Common Bean", BMC Genomics, 2010, vol. 11.

Lin et al., "Molecular Characterization of Iron Deficiency Chlorosis in Soybean", Journal of Plant Nutrition, 2000, pp. 1929-1939, vol. 23.

Padgette et al., "Development, Identification, and Characterization of a Glyphosate-Tolerant Soybean Line", Crop Science, 1995, pp. 1451-1461, vol. 35.

Yoon et al., "BARCSoySNP23: A Panel of 23 Selected SNPs for Soybean Cultivar Identification", Theoretical and Applied Genetics, Mar. 2007, pp. 885-899, vol. 114 Issue 5.

Karkosh et al., "Seed Treatment for Control of Iron-Deficiency Chlorosis of Soybean", Crop Science, 1988, pp. 369-370, vol. 28.

Song et al., "Development and Evaluation of SoySNP50K, a High-Density Genotyping Array for Soybean", PLOS ONE, Jan. 2013, pp. 1-12, vol. 8, No. 1, e54985.

\* cited by examiner

SEQUENCE LISTING

<160> NUMBER OF SEQ ID NOS: 186

<210> SEQ ID NO 1
<211> LENGTH: 401
<212> TYPE: DNA
<213> ORGANISM: Glycine max

<400> SEQUENCE: 1
atgaagccgg tgcccgtttt gccaaatggc gtgctgtgct caagatcggc ccaaacgaac    60

| | |
|---|---|
| catccgagct ggctatccat gaaaatgcct acggtcttgc ccgatatgcc gtcatatgcc | 120 |
| aggagaatgg tctggtacct attgtagagc cagagatcct ggtggatgga cctcatgaca | 180 |
| tcaacaagtg tgctgaggtg accgagcgcg ttcttgcagc atgctacaag gctctaaatg | 240 |
| atcaccatgt tctgcttgag ggcactctgt tgaagcccaa catggtcacc cctggttcag | 300 |
| agtctaagaa ggtcacccca gaggtgattg ctcaatacac tgttacagct ttgcagcgaa | 360 |
| ctgttcccgc tgctgttccg gccattgtct tcttgtctgg t | 401 |

<210> SEQ ID NO 2
<211> LENGTH: 1168
<212> TYPE: DNA
<213> ORGANISM: Glycine max

<400> SEQUENCE: 2

| | |
|---|---|
| gttatcaatt gcgaaagatg gtggaaagcc aataatctgc tatatcatat agcggatagc | 60 |
| cggatagcat cgtgagcatg taacagaggt cacatataat ggttgaaata tttgatatat | 120 |
| atacactata tatgtatata aaactaagtt gtatgcaaat aaaaataaaa tacataaaat | 180 |
| tggcataata ttaattatta actcaaaagt tcaattggca tatgtatata gtcccaagtg | 240 |
| gatctgagaa attccgctat gcaatagcgc tacaggccta tagcgcacta tagcaactat | 300 |
| ttaacaacat tggtttcctg tttatttttt tcccaaaatt tactaatttc ttagtagtag | 360 |
| tatgtgtcct tgcctcttct cttttgatat aatgttcaaa ttatgactta gatgtggaca | 420 |
| tttatcgtct ctttttttacc tttgacattc tagggtgaag ttgaagatta tcaaaattcc | 480 |
| aaaaagaaag agattaaaaa cttcaaagag aatctgaaat cattctggga caatttggtt | 540 |
| cgtgagtgtc agcatggccc attgtttgat caagttttat ttgacaagtg catggactat | 600 |
| atcattgcac tgtcatggta agtatgctat ttaaaacttc tgactctagg aaaatatata | 660 |
| taccatgact tatctgctac tgtacatatg tagcacccct ccaagagtat accgtcaagt | 720 |
| tgcatcattg atgggtctta gtctggtcac atcatacata actattgcta atatgcttcg | 780 |
| tgctcaaaga gagactactc agagacagtt ggaagctgag aaaaagaaaa gaactgaggg | 840 |
| gcctcgagtg gattcactaa agaaaaggtc ttctgatact catgatagaa tacagttgtt | 900 |
| ggaggagatg atgcgcaaga tatttactgg gtaggagttt gctaaattaa gaaactatt | 960 |
| ttctttataa aggcaaagaa aacaatattt tatcacaagt attgtatttg ctgtggctgt | 1020 |
| atatctaacc tgtccattta atgctttttt gaaggttatt tgtgcatcgc tacagagaca | 1080 |
| ttgaccaaaa tattagaatg tcatgcatcg aatcgttggg tgcatggatc ctgtcatacc | 1140 |
| catcactttt cctgcaggca tgcaagct | 1168 |

<210> SEQ ID NO 3
<211> LENGTH: 902
<212> TYPE: DNA
<213> ORGANISM: Glycine max
<220> FEATURE:
<221> NAME/KEY: misc_feature
<222> LOCATION: (752)..(752)
<223> OTHER INFORMATION: n is a, c, g, or t

<400> SEQUENCE: 3

| | |
|---|---|
| tacagttcag agcttgttct gaacggaatt gtaatccaaa aattggaact tgagaggtat | 60 |
| attttttcctt catatttctg ttctttttttg tccgcaactc tgcatgcaca aggaattttt | 120 |
| ttcctacttt attcttttaa ccttgtttga tatattagcc tagctacata aatgccatct | 180 |
| ttgatctcaa ccatgcacag ttttttccca ctacaatgat ttgttgcctt gaagtaaaaa | 240 |

```
cacctaagaa tattgggttc aaattgtgca aaaagcacat tgggttgaaa ttactgtatg    300
aacccgtagt tttgcattac agtccctctt ttgacattat gtctaaacta agttaagcac    360
aggaaaaaga tcttataaag tgagattttc tttagaggtg aacaagaaca gatgcatata    420
ctatattggc ttttagtggg ttcagatcac agttaatgat tacacccttg agtgtcaact    480
gcggaggata agttcacaag cacaacttac gctatgccat gtagatgagt aagtttcaga    540
caacttagga gtcaaagtag gaatcttttc gcatatttgc atgtagcgag cctattgttc    600
atccctgagg acaaagtaaa actactgtct taccaataaa gtgattagta acgcatcatc    660
tcaacaattt tatcaaaatt taacattatt atgatgaact ttggcagaca ccaactcttc    720
atgaatcaag ttacaaggaa taacccaagt gngtcgaatc ggtttgggaa gatttacaga    780
aggcgtagag gccttttttc tggaccgtag cagattttt gaaagtgtca ttcaggtcta    840
cggtggaact cgtaaaatta atgggcactc tcgtctcaga tgctgactta tgagcgcttc    900
tt                                                                   902

<210> SEQ ID NO 4
<211> LENGTH: 400
<212> TYPE: DNA
<213> ORGANISM: Glycine max

<400> SEQUENCE: 4
ccaacatttt cattttttgaa aaggagttat cctttttgat cgattttcca gaaagcgttc     60
cgattgtgct gctattccgt gtccgactcg gctgagtttg gccgatccaa acaagcgagt    120
cagttgttgg aggaaagccc ctcatccaag aggaaccagt tccacccgta tgctccagat    180
tggaaaaatg gttacactct agaaggttaa accccttctg tggtccctct agcacactat    240
cgaagatact agatactcca tccgcacgtt tcgaagctat tcatgatatt gatttcagtg    300
cttctgactt gaaaacattg gaacgaactg accgaagcaa tttgcttctt cataccatca    360
aaactgaaga gaagaaaacc tctatcgaga atggcagtca                          400

<210> SEQ ID NO 5
<211> LENGTH: 794
<212> TYPE: DNA
<213> ORGANISM: Glycine max
<220> FEATURE:
<221> NAME/KEY: misc_feature
<222> LOCATION: (306)..(306)
<223> OTHER INFORMATION: n is a, c, g, or t
<220> FEATURE:
<221> NAME/KEY: misc_feature
<222> LOCATION: (442)..(442)
<223> OTHER INFORMATION: n is a, c, g, or t
<220> FEATURE:
<221> NAME/KEY: misc_feature
<222> LOCATION: (558)..(558)
<223> OTHER INFORMATION: n is a, c, g, or t

<400> SEQUENCE: 5
gcaatcacag tgaaaataac cagctattat ggcgctacag ggaagcattt ttgaaatccc     60
attttgcctc aatgctgtga cattttgggg gtttgttggg ggcaaattag agattttcat    120
cctccctttt caaaactaaa aaaaaaaaaa caaaagaaa ctacttggat acagttttcc    180
atgcttctct ctcctgtgtg accaaacacc tgtctaccca gactacccat ctatgggttc    240
cgtctgacag tattttttggc aacacccaac caccattatt ttctctgttt taaactctga    300
agcacntcct gaaccacctc tgttcttttc tccatgcaat ggccatgcca ttatctcagc    360
```

```
tgctacacgt cgctatctga gtttgataac tatgatttat cctatacaaa ttttattctt      420
aaggattgac atttagatgc antgatattg atagatatta ttcttaactc aattgaataa      480
cttcttgtat ggcaattcat agcatcaaat cattgtagag tagatatgtt tgtgtattcc      540
tcttgtattt atctaatnga acaaggtgct gtgtgtatgc tttatttctt taaacagact      600
actctcagtg agcatgataa tgaaatgtca aggaggctgg tgaaggtact tgagaagttg      660
agatatacag atcgtgcata ttaccagttg tgccacttg tgaggcaagg tgaacaaccc       720
aaagaaggat tcctccttct ttcaaacctt gttgaggacc agatgggtgg taacagtggg      780
tatgctgaat ggat                                                       794

<210> SEQ ID NO 6
<211> LENGTH: 360
<212> TYPE: DNA
<213> ORGANISM: Glycine max

<400> SEQUENCE: 6
gcccgagtgg tacgtctgga atgggatcgg aggtacctat ctgttcttgg ggttgaaaac       60
aaccaattgt atgagttgag attgcaggtg ccagaaaatg tgttttcaga ggaggaaaat      120
gatcttcgtc gaatcatgga ttcgtttcga gtgaacaaga ttgccgctta gaactagagt      180
gttggataca tgaagatatt ccacggtctt tgaattttaa tcttatttct tctttattct      240
gatgatctct ttctctaatc ttttttctttt ttacttgatt gaattttttt cttcttggc      300 taaattttgg ccatactatc atatcatttg ttacattatt gttctcactt tcccatttat      360

<210> SEQ ID NO 7
<211> LENGTH: 490
<212> TYPE: DNA
<213> ORGANISM: Glycine max

<400> SEQUENCE: 7
tgggttcctc ttcatctttg tgtttcggca cacccaagtt gttcaattca gcaagggtgg       60
cggtgaatgg tcggcgaaga aacaaaggtt tgagttgcaa cgccatgttc ggtctggggg      120
tgcccgaact ggtcgttatt gccggcgtgg ccgcccctggt ttttgggccc aagaaattgc      180
ctgaagtcgg ccgtagcatc ggcaagactg taaagagctt ccaacaggta acccaaatta      240
taacaactgt gaggggaaaa ctaaaatgaa atgggaggat ggttatttgt tggattttgg      300
cattcacttt tgcacattat tgcttttaag gatggttatt attattattt ttggcaaacc      360
aatggtgtag gctgcaaagg agtttgagtc ggagcttaag aaggaacctg attccaccca      420 agggactca tccgagaaac ctattgttac agtcactgag cagcagcagg aggacaatga      480
ggtgtctact                                                            490

<210> SEQ ID NO 8
<211> LENGTH: 19
<212> TYPE: DNA
<213> ORGANISM: Glycine max

<400> SEQUENCE: 8
gcggatagcc ggatagcat                                                   19

<210> SEQ ID NO 9
<211> LENGTH: 44
<212> TYPE: DNA
<213> ORGANISM: Glycine max

<400> SEQUENCE: 9
```

-continued

```
<210> SEQ ID NO 10
<211> LENGTH: 16
<212> TYPE: DNA
<213> ORGANISM: Glycine max

<400> SEQUENCE: 10
catgtaacag aggtca                                                          16

<210> SEQ ID NO 11
<211> LENGTH: 15
<212> TYPE: DNA
<213> ORGANISM: Glycine max

<400> SEQUENCE: 11
atgtagcaga ggtca                                                           15

<210> SEQ ID NO 12
<211> LENGTH: 27
<212> TYPE: DNA
<213> ORGANISM: Glycine max

<400> SEQUENCE: 12
gagtcaaagt aggaatcttt tcgcata                                              27

<210> SEQ ID NO 13
<211> LENGTH: 24
<212> TYPE: DNA
<213> ORGANISM: Glycine max

<400> SEQUENCE: 13
ttactttgtc ctcagggatg aaca                                                 24

<210> SEQ ID NO 14
<211> LENGTH: 16
<212> TYPE: DNA
<213> ORGANISM: Glycine max

<400> SEQUENCE: 14
tttgcaagta gcgagc                                                          16

<210> SEQ ID NO 15
<211> LENGTH: 15
<212> TYPE: DNA
<213> ORGANISM: Glycine max

<400> SEQUENCE: 15
ttgcatgtag cgagc                                                           15

<210> SEQ ID NO 16
<211> LENGTH: 24
<212> TYPE: DNA
<213> ORGANISM: Glycine max

<400> SEQUENCE: 16
ggttccgtct gacagtattt ttgg                                                 24

<210> SEQ ID NO 17
<211> LENGTH: 24
<212> TYPE: DNA
<213> ORGANISM: Glycine max
```

Line preceding: `gcatacaact tagttttata tacatatata gtgtatatat atca    44`

```
<400> SEQUENCE: 17
atggagaaaa gaacagaggt ggtt                                            24

<210> SEQ ID NO 18
<211> LENGTH: 15
<212> TYPE: DNA
<213> ORGANISM: Glycine max

<400> SEQUENCE: 18
cccaaccacc attat                                                      15

<210> SEQ ID NO 19
<211> LENGTH: 14
<212> TYPE: DNA
<213> ORGANISM: Glycine max

<400> SEQUENCE: 19
aacacccaac tacc                                                       14

<210> SEQ ID NO 20
<211> LENGTH: 1159
<212> TYPE: DNA
<213> ORGANISM: Glycine max
<220> FEATURE:
<221> NAME/KEY: misc_feature
<222> LOCATION: (1144)..(1145)
<223> OTHER INFORMATION: n is a, c, g, or t
<220> FEATURE:
<221> NAME/KEY: misc_feature
<222> LOCATION: (1150)..(1151)
<223> OTHER INFORMATION: n is a, c, g, or t
<220> FEATURE:
<221> NAME/KEY: misc_feature
<222> LOCATION: (1156)..(1156)
<223> OTHER INFORMATION: n is a, c, g, or t

<400> SEQUENCE: 20
ctctaggtat gattgtcatc tatggatgtg ttacttcgac tttctaaatg gcttattttt     60 taattctttta tttatttaca aatttggggc tgtgttccag tattatgcct ataaaacagg   120
ttttggaagc aagacctgat atgtgtctgg tggctgaata ccatcagca gaaggaaggt    180 tagatagttt tcacttttag agtatttttgg attttggtgc acttaatttc ttgcaggcgg   240
agggattttt tctttcattc taaaggtcac caattgtttg tgtttctgga ttgtcttgca    300
gttacatcga gacattcgat gctgatatga acagcgagat aagtttgcca tcacaattga   360
gcagccacac gtcagatgga tcaattttta tgagtacatc tgaaagcagc tacaatagtg   420
atcaaggaag tggcaatgag gatggtcaag atgccaacta tgtgatatat gaggaaagct   480
cagatgagat tgacttttttg tccctctagg gaatcctcct tgtgaggcat cagtttagaa   540
ggacaataat ctagtgaact tggtactctc tcattgtctc tgtggatgcg ggtgcacttg   600
tgtgtgttgg gggagggggg ttacaagttg attctaatg tataaaagca ctggtgcctt   660
gaggtcatta gtgaagaaaa caaaactagg aagtaattat tgaaaagaa agaatttatt    720 atataataaa tacaaaaatc atttaatact tgtttaagga attagaaata tttaataggg    780
tgtaataaat actccttcac cattgtcctc aatatacttg cttgacccctt taataaaagc   840 attttactag gatagattag ctttgctttt aggttttgac tttggacaac tatgcactat    900
gaacaagttt gaaagcttac gtagaatatg atgttttaga gattgtcatg gttggcacgt    960
gacaagtttt gctgtctagt atcccatatt ggaaattgga gataccctaac acgtttgtgt  1020 ccacaaaaag ggatgttaca ataaagtttg atgctttgaa attaattcct gctgtgtttt  1080
```

| tttccttcta aactcaatgt tgttcgcct cttggcgttt cttaatattg tgtttgaatt | 1140 |
| tatnncctan ngagcngta | 1159 |

<210> SEQ ID NO 21
<211> LENGTH: 360
<212> TYPE: DNA
<213> ORGANISM: Glycine max

<400> SEQUENCE: 21

| ggattgcaat gggaagatac agaagttatt ggaccaaata tatgaacttt gacctcccta | 60 |
| ttttgcaacg ttgcaatctc caggcgtagc ccaaaattca atattatta ctctacctgg | 120 |
| ctggttttat ttgattaatt tgttggcaca ttaattgcct gcttcagtcg attctttatt | 180 |
| gttctttggc gattcttctt gtaaagccct tcatagatgc atagaatttc ctacatatat | 240 |
| cttttagaa gcttagctaa tttgtagtga cattcagatg aaataagact cgcataggta | 300 |
| ttttagctgc ttggagaaac cattatttgt tgtgtacata attcattccc gtgctatcta | 360 |

<210> SEQ ID NO 22
<211> LENGTH: 935
<212> TYPE: DNA
<213> ORGANISM: Glycine max

<400> SEQUENCE: 22

| ctctctcaaa ctcgcaaagc gaattactga aaccctagcc tctgtttctg tgtttattta | 60 |
| cttttattct acgcatcgaa ttcaattctc tgtgatctga acccgtgaaa tcaatgtgcc | 120 |
| tctttcggaa tcgcagagcg agcaacggtg accgccatca tcatcgatga agcgatcggg | 180 |
| tcggtggcag aggactctga tcctcgctct tctctttctc tccctcgttg ctccgctcgt | 240 |
| ttacgtctct cacctcctca acactctcac ttccgacggt aaataaaaac tcaactcctt | 300 |
| cgcactcgcc cgtgcatacg ccactttcct tgttctgtgt gctctctctc tccgttttag | 360 |
| ttgacttttt gcgtttctgt taaattgcgt tgcaggacga cgagattttc ttgatgattt | 420 |
| atcgagtttt gtaagaatct tgcttctgaa gcctgatcag tttatttat tttattttg | 480 |
| tttatttatt taattgcttc tatagctcaa cctgtttggt ttccgagaag gaataccagt | 540 |
| tagatggaat agaatatagt gaaacatttc tttctttctc tcttttttt caaaattttt | 600 |
| gatttaccgg tgtgttgaaa gtttgccga ccgatagctt actggaactt cttgtacttt | 660 |
| caataatttt agttttggat aaaatgattt ttcatgttta attatttaa ctggattttg | 720 |
| tttttttat gctccatcgg ctgccaattg aaattctaca gcttctgatg ctttattgtg | 780 |
| gatttgggat ttgattttg tttgtatctt gcagacacat aggtcagatc ctttaaatgc | 840 |
| aattgaacag gtagtggaac atgttttag tttgtcttca tcttcttctc tcttcccctg | 900 |
| gtgaatggga gaattaactt tttccttggt atttg | 935 |

<210> SEQ ID NO 23
<211> LENGTH: 1188
<212> TYPE: DNA
<213> ORGANISM: Glycine max

<400> SEQUENCE: 23

| ataattatct gagaccggac atcaaacggg gcaactttac cagagaagaa gaggacacta | 60 |
| taatcagttt gcatgaaatg ttgggaaaca ggtaattaaa ctaattatat attttcccta | 120 |
| gctggcatag catttcacat tagtatagat aatttaatcc aagttaactt caacttaatg | 180 |

```
aaagaaatta atcctttcac cgaaaaccaa gaggttgaaa tttgaaaaac caatagtact    240
caggctcaaa cagtgaaaca aagattcccg gaatatcttc attaatttct atatgttggg    300
tccttttcta ttctgttcca tgaagctgat ggaggagcag atgcatatgg cttcataaac    360
ttctactctt ggtagtatac aaattcatat caaaatctta atttatcggc agcctcgtgt    420
tttcttttat tattactact attttaaaga aagggaatag tttagttact gctcttttt    480 tcagataatt gtttcattgt ttgggcccat gagcactttg gtttttcttt agtttttaag    540
ggaagcaaaa tcataatcag tgggatatat gtcgctctgc aaagattctc tcttttgctg    600
caacatttca cgtgctttct taacataata tatttaagca catcatcatt caatatccca    660
tgacattatt actactgtat tattatggtg acttggagca gcaagctata ccctatttta    720
ttaatgaaaa atgttaaccc aggggtactg aaggtattga ttaaaaaaat ttaaatagaa    780
atatttttat caagagaaag aacattctac acaataaata ttttctttc ttaatttctt     840 acataatatt ctaaagatac tgattaatgt atcctttatt aatttattta atttaatgaa    900
tatttcctcc atcattatcg atcttgtcca ctaatcttgt gataaccttg tgcagatggt    960
cggctattgc ggcaaggttg tcagggagaa cagacaacga gataaaaaac gtgtggcaca   1020
cccacttgaa gaagaggctg ccacaaaatt accaacaaag ccatcacact aaaaaacgaa   1080
gcaaaaaaca accaccaaag ttggatgcgg acgcctccaa atccaaccaa gacgccaaac   1140
tagaacaaca agacccgtt aatattcatg gatcgaactc tgaggaca                 1188

<210> SEQ ID NO 24
<211> LENGTH: 524
<212> TYPE: DNA
<213> ORGANISM: Glycine max

<400> SEQUENCE: 24
ttgcctttga agagattgat tctcctcaga cattctgacc ttccttgcac gaacctgaga     60
ctgcaaccgt gaaagagttt gcatgcattg caaggtagta gccgcttgtc gttgaacaga    120
ttgcccttgc accaacgttt tcaacctcga caaacctctc aagccacgca aggattttct    180
tgcctgaaac cccacataac atggaactat tacacacaaa aagaaggttg aataaattaa    240
atttctcctg taaattaaaa tcaacttata cacttatctg agaagaaaac aagaatgtaa    300
aatgcactta aattttatag ataaatttta ttaggacata attgactttg gtggtaataa    360
catgaacctt ccatgttatt agtcgtttca tttgtgttcc caataaatag gattcataaa    420
agtctatacc gaatatccac ggtatgctgt ttgaatcttg atagctgtca tttcttgatt    480
cgcttttcca ttagaacgag gcgtgtttgt gagacgagta acct                    524

<210> SEQ ID NO 25
<211> LENGTH: 628
<212> TYPE: DNA
<213> ORGANISM: Glycine max

<400> SEQUENCE: 25
atgcctgcag ttaaccacac attaaagacc acggagtttt cgatggttgt atttgtatat     60
acgggtggga ttttttctga ttgtcttaat ttaagattaa aatacaaaaa tacaaatgct    120
gaattctctt gaaaaaaaaa tacaaatact gaattgtagc aaatcaaact ttttttttcta   180 cataaaaaaa aacatttttt ttcctaaaaa tgccttttgt ggttgaagat ggttaacaac    240 catttttattt tcagttatgt attcaaatag taaaatagtaa tattcattta acctaatatt   300
attcatataa tcaaaacttt acacaagata ctagattaaa atctagtgtg atcattgtac    360
```

```
ataaaaagaa taatcgaagc attacactat tttctgtcaa aaaagaaaac aattgaaccg      420
tttcgagcaa atcaaatcat caacatcata tcaagtttat aatcaaagta gatcttttct      480
cgtatcatgt gatttttta tgtgtaaaaa tatgtcaaat taagacaatt ttttttaaga      540
ccctaaatca ataaaaaaaa ttatcgaatc gtgttgggtc aaatttattt attaggaaaa      600
aattcaattt aacttaaatt acccaaat                                         628
```

```
<210> SEQ ID NO 26
<211> LENGTH: 477
<212> TYPE: DNA
<213> ORGANISM: Glycine max
<220> FEATURE:
<221> NAME/KEY: misc_feature
<222> LOCATION: (148)..(148)
<223> OTHER INFORMATION: n is a, c, g, or t

<400> SEQUENCE: 26
aacaagatat tccgatgtct gaagacattg tttctgtttg ttgtgatgaa gaaaggaaga       60
tccattctga agatgaggca ttgggagtac ccaatggaac tgaaacatca tgttttccta      120
caaactcttg tgttgaaaac ataatttntg actgtcaatt atcaccccca tacatacaat      180
cacccccttg tgcacaaccg gttgatgagc ttgataacac caagaaaatt gaagctcgtc      240
tcgaagtgga gatgcctgga gaaactaatt gctttgcac attgagggaa tatttgaaac       300
acaacatatg tctgccagtt gtggaagcag tccaggggac caagatgcag caatttcaag      360
ccccacatga tacttttacc ggacaaccac cttccttgga aatgcattgg tccagctttc      420
aaataaatat tgatccttcg tctttgatg aaaaacatgc tgctgcaggc atgcaaa        477
```

```
<210> SEQ ID NO 27
<211> LENGTH: 774
<212> TYPE: DNA
<213> ORGANISM: Glycine max

<400> SEQUENCE: 27
ggaaaaactt tgagacaaaa actaaaacac ttatgaaatt agacaaaaga atgcaatatt       60
aacagaatgc tacaacattt caagaggacc caaacgtaga ttataaggag aataatgaat      120
cctcctattt aaaacagaaa gaaactccta tcctatctaa aacagaaaga acccaatgag      180
ccaaagtggc tcaaaaatgc aataaagtat tccaatattt tcgcatacaa atgattgatt      240
ctttgaagca gccattaacc aagaaccatc atagagacaa tcctatccta tgacgactgt      300
aaagggaaag aggtgctctt gaaaatacac gcatttcatt acaaccaaat gcactactag      360
ataactacat atactgcaca atgcgataaa atttaacact ctttgttcct ttcaaaacct      420
ttaaggcatg taaagagaaa agctccaacc tatgattgga gaaactcatt gttggctagg      480
aaccccaaaa caattcagca ggtgtaccac aaaagtggcc tacctatagt attatcagct      540
tattttagca tgtttatacc tagatgtctc tatttcttta tgaacttcaa tagttcaact      600
accatttgat gaatgtgtcc atgatcatat cataacttat atcacgcaaa cttcagaggt      660
tattatcttt tttgtttctc attgtattct acaccaatga ggtaaaacaa gcgagcccca      720
aacgcatgat gaaacataat catccattgt tgctacttgt cagatcacct cttg            774
```

```
<210> SEQ ID NO 28
<211> LENGTH: 689
<212> TYPE: DNA
<213> ORGANISM: Glycine max
```

-continued

<400> SEQUENCE: 28

| ttgttatgca ttcgagccaa gtacaaaact ttatatgtgt tagattcgat gcatgataat | 60 |
| ttctcaacca gcaagaagaa cttggatgat gcaatggtag tatttaacat ttattttccc | 120 |
| tcaggaaata tttacattag ttttgtcaaa tttgtatccc tagcttttct gtctgatcca | 180 |
| accaaaccaa tggtattttt atgcaaagaa acatcgtttt aaggagcttc tggtattaat | 240 |
| gaatcctggt ttgaccaaag agagtgcatc aataacactt cttcacgttg atgttcccag | 300 |
| gcagcaaaac atgtgggtag tgtgtgtagc tctaatgttc atttatgtag aaaactcaat | 360 |
| tcatttttgg tgctaatagt atattgtttc tcattgatgc tttatatgtt tgataaagtc | 420 |
| atgcttgtgg catccatgtg ctgaaataca tggaaatttg ggatggatca ataaaatggc | 480 |
| aagacaaaac catgcctgat tatcaacacg tgagtattta tttgtctttt actaaactac | 540 |
| catgtggaag tgggacttac ttttaaaaaa attgcagaaa gaaatcttga agattcgaca | 600 |
| aagcctatat gtggatgggt tcgacatcct aaaaacgaga ttagagaaga gattttgaag | 660 |
| gcagcaggag tatgggggaa attatgctg | 689 |

<210> SEQ ID NO 29
<211> LENGTH: 170
<212> TYPE: DNA
<213> ORGANISM: Glycine max

<400> SEQUENCE: 29

| tatgacagat atgcatagat tgagttctcg cctattaatt ttattagcag aggttccagt | 60 |
| tttatcgatg gtcttctgtc agaaaattgg aggtaggtta tgccggaaag tctatttata | 120 |
| ttccgtcctt tccttcaaat gatggcatag aggatttgtg cattaagaag | 170 |

<210> SEQ ID NO 30
<211> LENGTH: 657
<212> TYPE: DNA
<213> ORGANISM: Glycine max

<400> SEQUENCE: 30

| ctcttatctt cttttgggca gagaggcttc acgcttgagt agccatggcc tccttaagct | 60 |
| gccaggttca ttccaccaac ttgttgaatt ctaagaatgt caatagcagg aggaaacgtt | 120 |
| taatttcttg ctcagcacag cctacacaaa acaatattaa ggtataagct gaatgaaat | 180 |
| gcaatactct ttaattcaat gcacaaaatc aaagtacaaa gtgcttgcat tgcaacgtac | 240 |
| cctttgtgga acaggtagtg attaatggag caaccaagga aataggaaag gcagcagtag | 300 |
| tggcagtgac taaggccaga ggaatggagg tagcaggagc ggtggatact tgtcatatcg | 360 |
| gggaagacat tggaaaggtt tttttttgcc tttggtgtca ttatccaaac caacttaatt | 420 |
| cttatgttgt ccttaatcta ttttttagatt gttttaatt ctttcagata tgtggcatgg | 480 |
| aagagctcct tgaaataccc atcataaatg accttactat gattttgggc tccatatctc | 540 |
| aggtaacaaa cttggtattt ttttctcttc ttaatctgtt ttcttgaata acgttttgaa | 600 |
| tgacaatttg cagtccaagg cagcaggagt tgtagtcgat ttcactgacc cttccta | 657 |

<210> SEQ ID NO 31
<211> LENGTH: 25
<212> TYPE: DNA
<213> ORGANISM: Glycine max

<400> SEQUENCE: 31

| aatatccacg gtatgctgtt tgaat | 25 |

<210> SEQ ID NO 32
<211> LENGTH: 24
<212> TYPE: DNA
<213> ORGANISM: Glycine max

<400> SEQUENCE: 32
ctcgttctaa tggaaaagcg aatc                                          24

<210> SEQ ID NO 33
<211> LENGTH: 17
<212> TYPE: DNA
<213> ORGANISM: Glycine max

<400> SEQUENCE: 33
cttgatagct gccattt                                                  17

<210> SEQ ID NO 34
<211> LENGTH: 14
<212> TYPE: DNA
<213> ORGANISM: Glycine max

<400> SEQUENCE: 34
agctgtcatt tctt                                                     14

<210> SEQ ID NO 35
<211> LENGTH: 27
<212> TYPE: DNA
<213> ORGANISM: Glycine max

<400> SEQUENCE: 35
cgaagcatta cactattttc tgtcaaa                                       27

<210> SEQ ID NO 36
<211> LENGTH: 29
<212> TYPE: DNA
<213> ORGANISM: Glycine max

<400> SEQUENCE: 36
aaaaaatcac atgatacgag aaagatct                                      29

<210> SEQ ID NO 37
<211> LENGTH: 16
<212> TYPE: DNA
<213> ORGANISM: Glycine max

<400> SEQUENCE: 37
caattgaacc atttcg                                                   16

<210> SEQ ID NO 38
<211> LENGTH: 16
<212> TYPE: DNA
<213> ORGANISM: Glycine max

<400> SEQUENCE: 38
ttgaaccgtt tcgagc                                                   16

<210> SEQ ID NO 39
<211> LENGTH: 22
<212> TYPE: DNA
<213> ORGANISM: Glycine max

<400> SEQUENCE: 39

```
ccattctgaa gatgaggcat tg                                              22

<210> SEQ ID NO 40
<211> LENGTH: 28
<212> TYPE: DNA
<213> ORGANISM: Glycine max

<400> SEQUENCE: 40
acaagagttt gtaggaaaac atgatgtt                                        28

<210> SEQ ID NO 41
<211> LENGTH: 15
<212> TYPE: DNA
<213> ORGANISM: Glycine max

<400> SEQUENCE: 41
tccattgggt actcc                                                      15

<210> SEQ ID NO 42
<211> LENGTH: 13
<212> TYPE: DNA
<213> ORGANISM: Glycine max

<400> SEQUENCE: 42
cattgggaac tcc                                                        13

<210> SEQ ID NO 43
<211> LENGTH: 25
<212> TYPE: DNA
<213> ORGANISM: Glycine max

<400> SEQUENCE: 43
cctttcaaaa cctttaaggc atgta                                           25

<210> SEQ ID NO 44
<211> LENGTH: 25
<212> TYPE: DNA
<213> ORGANISM: Glycine max

<400> SEQUENCE: 44
gttcctagcc aacaatgagt ttctc                                           25

<210> SEQ ID NO 45
<211> LENGTH: 16
<212> TYPE: DNA
<213> ORGANISM: Glycine max

<400> SEQUENCE: 45
agctccaaca tatgat                                                     16

<210> SEQ ID NO 46
<211> LENGTH: 16
<212> TYPE: DNA
<213> ORGANISM: Glycine max

<400> SEQUENCE: 46
ctccaaccta tgattg                                                     16

<210> SEQ ID NO 47
<211> LENGTH: 360
<212> TYPE: DNA
<213> ORGANISM: Glycine max

<400> SEQUENCE: 47
```

```
gtatctcaat caatcaacaa aagctcactt tcataaagac acgcacacat attcttgtta      60
cacaaaatgg accaacaaga gggtaacacg tggacaatgc caccgttctg ggcggttgag     120
cagcgaaacc gccgccgtct tcgccgctct tactctctgt tgctcacctc cacctccctc     180
ctcgtactct tcctcgtact cgtgctggtg ttctcgctca tcgtggttcc gacgttgcac     240
tcgttcgctt ccaacatctt caaacctcgt acagttaaga acagctggga ctccctcaac     300
ctcgtactcg ttctcttcgc catttttgc ggcttcctca gcagaaacaa caacacctcc      360
```

<210> SEQ ID NO 48
<211> LENGTH: 364
<212> TYPE: DNA
<213> ORGANISM: Glycine max

<400> SEQUENCE: 48

```
ctttcagagt gctattaatc caccaggtgg cattaggcca gcaagtgaaa ctggagaaat      60
cacatgtcca gatacaagca aaaacattac ggttccatgc cctggagaag ctgtcctatc     120
tgttcttaaa gcagacacct acaacagctt cctttattgt aacacaatat gttttgcttc     180
atctttagct gtttgtctct tgcttgtgag tggactccct cttaataacc gattcttcat     240
ctggttcttc tcaatatgca tgtgcatcac cctcactgcc ctcacccta cctacttata      300 tggtttgcaa atggtcaccc caaacgacgt ttgggataat tcattattca gcatggttgg     360
agtc                                                                 364
```

<210> SEQ ID NO 49
<211> LENGTH: 1015
<212> TYPE: DNA
<213> ORGANISM: Glycine max

<400> SEQUENCE: 49

```
ggttttggag gcatcaccat caccatgaga gcaaaattgt tgtgttccc aatacgaggc       60 aggaactgtt gcttctccag aaccatcgat cactctctct ccgcttccca tgcttcctct     120 caatcccct caaccctcaa agacttgtgg accaacatca acgttggtga taaaccctt       180 aacaccaaaa ctgagctctt tgtcgattac atcgccaaca aggtgacatt tttcttcttt     240
tctcgtgtct ttctctttat gggcatctcg ttttttactct ttggctgttg tgggtcgtag    300
atgaataatg cttggattgg cttggagaag gcgccgagg ggtctttcaa gaacaagatt      360
catgggttag ttttgttttg ttgtttagtg gtgaagttgt ttattactgt aatgttcttg     420
atttcgagtt ttttttttg caggttgggg ttgcggctct tgtcgcgggt taagccctct      480
gagatatttt tgaagtctat atcgaaggaa atcactagtg ttgaaatcat ttatccatca     540
aggttggtgc tggactcttt gtttacatgg cttgtcaaag ggtgctgttt gtttgaagtt     600
ttacttttat tttactacca ttgaatgaaa tgtgtcctct ctctttttgt tgatcttttt     660
gttgtttgtt tgtggttact agatttaacc gatcaagttg ccattgttca actcttgcac     720
tttcttgata ttcaatgacg ataatggagc agtgtgaatg agagattaaa ttatgtcttc     780
tttgcatcta gaggcttttc cgggtggttt tatcttggat tttcatttta aatatcatag     840
ttatccttgt ttgagagaac ctattttctt ttctgtactt atatatagat tttgttgtta     900
tgttctctac agaatcatct cattttgaa catttatggg gaacatgatg ttaagaagaa      960
aatttagcac tatggatagt tttgctttc tttttcaac cttgtatagc aataa          1015
```

<210> SEQ ID NO 50

```
<211> LENGTH: 1049
<212> TYPE: DNA
<213> ORGANISM: Glycine max

<400> SEQUENCE: 50
atattactga ttttggtaac ttttctcac tttccttttt gagtttgcat taattgttca      60
tgtgcatgat ggttgctcat tgttcaatag ctcagagatt tgatgttttt tcagcagtta    120
attgctctat tgatacttgt tcatttcttt gagaaagcct atacactcct tggagaaggg    180
aagaaaagga aagtagtgct gacattggaa gagaacaata caaagccaaa ggaagaggca    240
aacatgttgg caattttcaa ggataatttg gtcaatccac cagaagagct aaacagccct    300
gcttctttga attcatcaaa aaggtctaaa cttccaaatg aaatccttca ggaattccaa    360
tcctacaacc cctccaatgc tttctccatg agctttggaa atgatgcttt gctagcttat    420
tccccttcaa acaagccctc cattcataac gggtatgtgc ccctaccttt cttttaaaaa    480
aagtgatttt gaggtaaaat aataactttt tagagatttt aataaaagtt aatttatgtt    540
tgtttatgat cataaaaatc acttttttt ttaaatagaa ataactgatt ttatgagaat     600
tttgtattta aatttcatga taactcataa taatagacta cagtaatcac acgttacgag    660
ccagattaat cacttaccta atgggttaaa gaatgtccat aattttttac agaagataaa    720
aaaaatagct tttcaatatt aatgataaaa aaatagcttt tcaatattaa tgatattcaa    780
gatagtatcc atctagtgaa attttatatt tttttgtttt tattattctg aaaagctaaa    840
acaaacacat aaaaaaccctt taaaatgatt aattttttaaa aataagtgat ttaaaaaagt   900
gtaacaaatg gacactttgt gtttaaattt cccaacaact cgtaacaatg agatttgaat    960
atttgatttg atttaaaatt tgagaaatga atgtgcatta agttctgttt ctcattctca   1020
tacaaaagat gtctcacaca cacaggttt                                     1049

<210> SEQ ID NO 51
<211> LENGTH: 412
<212> TYPE: DNA
<213> ORGANISM: Glycine max

<400> SEQUENCE: 51
taaacagagt tgagatgaca gacacatatt attacgatga gttcccttcc agagtaagca      60
acttagcatc attgatttga gaataagccc ttgtgtgtgt cttattattt gtataatttg    120
tgagcaggat gtgtttgaag gagcatgtga ctgtgctaga gaatggaatg gtttgttgtg    180
ggaagattca aagaagatgc atatggttgt taagaccgag gtacatccgt atgtacgaga    240
ttatttacgc cgtcaaaagt aacagcaaag gcaacaccat ctcatgcatc ctggtcctgc    300
caacatgcaa atggaaaacc gggggaaaa tgcatttga gctcctttta gaatttttt      360
ttaaaaagaa tgtatttgcc ttcaaggtaa ttagttttga cttccttttt tt           412

<210> SEQ ID NO 52
<211> LENGTH: 301
<212> TYPE: DNA
<213> ORGANISM: Glycine max
<220> FEATURE:
<221> NAME/KEY: misc_feature
<222> LOCATION: (120)..(120)
<223> OTHER INFORMATION: n is a, c, g, or t

<400> SEQUENCE: 52
ccatacatca tcttaattga tatgactgtt cttcctttct tgtctacct tcaaatcagc       60
atgctcaaaa cacttgaaag gtaccagaaa tgcagctatg gtgctgtgga agttagcaan    120
```

```
cctgccaaag agctcgaggt atatagcaac tgcagctctt gctgtttact ggcattacag    180
cttatctcag aaagttcata taggaaacta taatataatt aattatgtaa cataccatat    240
atgtagtttt tctttattat tgttacatct ttcaattctg gttacttttc atttgtagca    300
g                                                                    301
```

```
<210> SEQ ID NO 53
<211> LENGTH: 301
<212> TYPE: DNA
<213> ORGANISM: Glycine max

<400> SEQUENCE: 53
ttaacacaac ctctttttaa cttatttta aagtttgta attaaatttt gaatatttat    60
ttaataagtg ggctaatatt gaatagtaat aaaaagaacg ttgattgcaa tcacctaaat    120
ggattgatat agaccccgca ttttctttt atagtcactc gttagcaaac ttgcgtccat    180
tattcctcag taagccctat acacacttac tagatttgtt ttttttttt actgcaactg    240 taactttttc cccactttag tttcacaaag actcccttat aaattataat caatcacaat    300
c                                                                    301
```

```
<210> SEQ ID NO 54
<211> LENGTH: 670
<212> TYPE: DNA
<213> ORGANISM: Glycine max

<400> SEQUENCE: 54
cacaccagca ttttcagctt gggttggagt ttgacaactc caaacctgcc ttcagttaca    60
atggttctgt tagtcaaagt gtaagccttc caaattccat tttactctct ctcttttcta    120
tcttttcaaa acactgggaa ctctaaatga gaacatttttt ctcactacac tcaactctaa    180
ttggatgttt ttacaataaa ataaaatcag tataaatttt ggatccaaca acggcagaag    240
ttatttaaac tttttcaagt ttctaaccca atcaatttta aattatttt taacatgaaa    300 tcaaacatat caaatatat tcaaaactaa ttttgaattc atcagtatta tgtaaccaaa    360
cacgcatcaa gctcttaggt ggggaaattg gaggttttca tttattcg gtttgactcg    420 ggatgtggaa aatattatat actatgaact acatgtttct tcttttgggg tggtggtttt    480
cttgcttttg gtcttcccat gacatgtttt tgccaaagat ggattcacaa ttaagtagtt    540
tccattcatg gcatgttcaa tgccaacttg aactttctat ttaccttgtt tttggccggg    600
tttatctaca taatctgtct ttattggatt gttttccatt aatttgactt gttccgagct    660
cgtgtttcat                                                          670
```

```
<210> SEQ ID NO 55
<211> LENGTH: 301
<212> TYPE: DNA
<213> ORGANISM: Glycine max
<220> FEATURE:
<221> NAME/KEY: misc_feature
<222> LOCATION: (93)..(93)
<223> OTHER INFORMATION: n is a, c, g, or t

<400> SEQUENCE: 55
ttcatatcat taacctgata tttctcagct tcatgaatca ttctttaat ctgctcagct    60 gaaagccttt tttggtcatt ggttatggta atntcattcc tataaccagt ggttgtttcc    120
tccgcagaaa cagatagaat gccatttaca tctattgtaa agcatacatc cacaggatgg    180
```

```
ccacgaggag caggaaccaa acccaaaaga ctaaagaaac caagcaaatt gttatcattt      240
gctctggttc tctcgccttc ataaacctca atacgcgcag aggtttggtt atcttccttg      300
a                                                                     301

<210> SEQ ID NO 56
<211> LENGTH: 301
<212> TYPE: DNA
<213> ORGANISM: Glycine max
<220> FEATURE:
<221> NAME/KEY: misc_feature
<222> LOCATION: (18)..(18)
<223> OTHER INFORMATION: n is a, c, g, or t
<220> FEATURE:
<221> NAME/KEY: misc_feature
<222> LOCATION: (176)..(176)
<223> OTHER INFORMATION: n is a, c, g, or t

<400> SEQUENCE: 56
atgagataaa aagaaaanga tataaaaata ataaaatgtt aataaaatat ataaaataaa       60
agagcgttga atattactc gatgaaaaaa aaaatccaac ccaaattcct cttcgatatc      120
aacgatcatg ttattagttt tttcatcaat tccaaatttc caatgctatg taactntttc     180
tacatagaat caaggttttc ataatgagct tgtccacatc taacaaacac gatggtggcg     240
catcagatac ctcattagac tacaatagga taaacaaaac aaaagtagca ggggcattaa     300
c                                                                     301

<210> SEQ ID NO 57
<211> LENGTH: 580
<212> TYPE: DNA
<213> ORGANISM: Glycine max

<400> SEQUENCE: 57
tattcaagtt tgcaatagtt cagggagaat tgctttgaat gcttcatatg ttactattac       60
tgaagaaacc aacaacgaag accacaaaat acttaaaatc tcatagcatc tattcccgag     120
gtcatttgac acaagcatct aatatcaata ttaacaaaat ttctacagga cagttgtttg     180
catgtatcct ctcatcctct gtaaataagt agacctacaa ccaaaacaca agttactaaa     240
aataacaata actcaataag gcattaaaaa tttaagtcaa ttgtggctct taatgcttac     300
gacagggaaa ctaacctcaa cattccgacg gtgatatttg acagtcaatt caaaatttga     360
tcaatcagtt tggaataatc ttcaacagct caatatcaaa caagagagtc ttgtctatca     420 accccctgatt cctcaacaca aaatccaagg ctcgttggcc ctgtaaaaat atatttggat     480
tgcatctttc tcataatcca ttcagatagt ggaagaacat agatattcac ttcttaccga     540
gaatgttgtt ggtcttgggc cactcttatt gaaatcattc                            580

<210> SEQ ID NO 58
<211> LENGTH: 301
<212> TYPE: DNA
<213> ORGANISM: Glycine max
<220> FEATURE:
<221> NAME/KEY: misc_feature
<222> LOCATION: (174)..(174)
<223> OTHER INFORMATION: n is a, c, g, or t

<400> SEQUENCE: 58
tctgttttgt tatttattgt attgctgctc agaacaattt gattaagaat aaaatcattt       60
tatttcctcc acatacgtat tgtctatctt cttctttgtt tattatattt tttctgttat     120
aaaacttaca aaatcccagt gaaccaagaa agtttactat ctagactcta gagnaccaaa     180
```

```
gaaattttga acctgagaat cctttaacag tccattacct ggctatatca gacttcgaat    240
ttccaaccag tcaaccgtaa caaaagaatt aaataaagaa aatgtagaaa caattatgtg    300
c                                                                    301
```

<210> SEQ ID NO 59
<211> LENGTH: 254
<212> TYPE: DNA
<213> ORGANISM: Glycine max
<220> FEATURE:
<221> NAME/KEY: misc_feature
<222> LOCATION: (1)..(2)
<223> OTHER INFORMATION: n is a, c, g, or t

<400> SEQUENCE: 59

```
nnttctacat ttcaatgcca agggactctg gatgggaagt cttacagggt ctgttctaca     60
agtgattatt ctgactgttg taacagtgtt aacagattgg cagaaagagg ttggttata    120 cttcttatg tgacttctcc attgctaata attgcttgag tcatttgttt ttttctttt    180 ccaactagtt tttgagccct tttcgttgcc tttgcttgat gaatccaatg gatgtctgtt   240
aattaaagtg gctc                                                      254
```

<210> SEQ ID NO 60
<211> LENGTH: 1385
<212> TYPE: DNA
<213> ORGANISM: Glycine max

<400> SEQUENCE: 60

```
ggcaacgaaa gcaagggaga gaatagttga gaagtcaatt aaagttcata atgattcagt    60
gatatgatcc aaggatccaa tcactataat aacttgggaa gcctaaaaca tgggatgttt   120
agaaggaagt ctagcctata acaataggaa actttgtagc tttgaggcat attggagtct   180
gaatgaaagt ttgagttttc tacctttgt gagagcttcc cttggttcta ggcaaagaac    240
taaatttgac cttatcaagg taacttgtgg cgatcaaatc tatgacttat cacccatctt   300
ctcccctatt tcttgagtgc ggcgtcaata tccttttcta aaagaaaact aaatcaattt   360
cttagtatga aaacttcaac ccgatccgtc tcgtttccgt gttcatatca ttcagtgaga   420 aatttttaa atatagtaga agaatgaaag agtggaaaaa aaggaagta ctgactaatt    480 ttctgttaga ttctggtttt gctattgttt ctatttttg gtgaagtaaa cagataaaag   540
ttattatgtc tgtatatatg tgatttaaga accggaattg tgcctatgaa gtgtaagggt   600
agcacataag tcagaactta gaaaattatt catgacatgc tgcagctggg agagcagtac    660
aagcaaaggt gggcagcgag gtacatcgac accactggac aaaccccaca agacctacac   720
aataaggttc tgaaggatat tggaaaacctt aacaacttgt tgacgatga ccttttaaca    780 gcctctgccc aagagtaagt gagattatat ggtttttttt tttttcatta tcatattatt   840
ggtataaaat atttcatcat ctttaattaa gtctttcttt aaattttact aacggaact    900 caatctaata tcacttggac gaaagacttc ttaatatatt ttgatatata tgacttttta   960
tttataaaaa taaaaataa atgttttttt atgagtaggt ctaattttgt ttttgggtga   1020
acttggatat cttttggcca ggagtgcaga ctaattaatg ttttagata cttaaaattc   1080 atttaagagg ttaacttcta aaaaattta acatatattt tctcatacat ggggaagatt   1140 caatcttta tcacatgttt agcgacaag attatatact aatcatgcca tggaaggtaa    1200
gttgaaaatt tgaactttga ttgtcttacc cttggggcgg tggtgtcttt tcaggtacca   1260
```

-continued

```
gaagcaaggc gttgcaacca tagaagaaaa gatttgctgg atgatgggag acgtgctctt    1320
gttgaagaac cagcttccgt tcccgttgct gcaggtcgac tctacagaag atcccgggta    1380
tccga                                                                1385

<210> SEQ ID NO 61
<211> LENGTH: 301
<212> TYPE: DNA
<213> ORGANISM: Glycine max
<220> FEATURE:
<221> NAME/KEY: misc_feature
<222> LOCATION: (79)..(79)
<223> OTHER INFORMATION: n is a, c, g, or t
<220> FEATURE:
<221> NAME/KEY: misc_feature
<222> LOCATION: (118)..(118)
<223> OTHER INFORMATION: n is a, c, g, or t
<220> FEATURE:
<221> NAME/KEY: misc_feature
<222> LOCATION: (148)..(148)
<223> OTHER INFORMATION: n is a, c, g, or t
<220> FEATURE:
<221> NAME/KEY: misc_feature
<222> LOCATION: (294)..(294)
<223> OTHER INFORMATION: n is a, c, g, or t

<400> SEQUENCE: 61
agccaaaatt caacaaaaca tcaattcttt aatatttaag cgcaaataac tgctaaataa      60 ttattttaa agacaattnt accttatttt ctattatcaa aatacaatta tttagccntt     120
atcatgtata gggaggcaaa tctagtgnag gatgcccttg caaaatatgg actaatttct    180
atggaagggg agggtagaat tttttacgtt tgtcctatct gattttagct gatgtagctg    240
tttgtcctat ccttcatgga gtttaataat attttttct tggggcttta gccnttttct     300
t                                                                    301

<210> SEQ ID NO 62
<211> LENGTH: 301
<212> TYPE: DNA
<213> ORGANISM: Glycine max

<400> SEQUENCE: 62
tttcactaaa ttaacttgtc agggttgcat agccatgctt aatttatgtt attttttcaa     60
gtcaatgtct aatatttgaa ctattatttt ttaagttgta tgaagcttat gaacaagttt    120
gttcaattac atgtgttaac tttgtgactt ggtgttctat gtttgactat gtatttggga    180
gctgtattct tgcatcctgg ttgggaatag ttcctttaca gatttatgta tatatataat    240
gcaaaagttg attgttttgt gccttgtgat actgaaattt tgaattcatt gtcttagtca    300
t                                                                    301

<210> SEQ ID NO 63
<211> LENGTH: 26
<212> TYPE: DNA
<213> ORGANISM: Glycine max

<400> SEQUENCE: 63
tctccattgc taataattgc ttgagt                                          26

<210> SEQ ID NO 64
<211> LENGTH: 25
<212> TYPE: DNA
<213> ORGANISM: Glycine max

<400> SEQUENCE: 64
```
aacgaaaagg gctcaaaaac tagtt                                                25

<210> SEQ ID NO 65
<211> LENGTH: 19
<212> TYPE: DNA
<213> ORGANISM: Glycine max

<400> SEQUENCE: 65
atttgttctt tttcttttc                                                       19

<210> SEQ ID NO 66
<211> LENGTH: 20
<212> TYPE: DNA
<213> ORGANISM: Glycine max

<400> SEQUENCE: 66
atttgttttt tttcttttcc                                                      20

<210> SEQ ID NO 67
<211> LENGTH: 29
<212> TYPE: DNA
<213> ORGANISM: Glycine max

<400> SEQUENCE: 67
gcgtcaatat cctttctaa aagaaaact                                             29

<210> SEQ ID NO 68
<211> LENGTH: 20
<212> TYPE: DNA
<213> ORGANISM: Glycine max

<400> SEQUENCE: 68
gaaacgagac ggatcgggtt                                                      20

<210> SEQ ID NO 69
<211> LENGTH: 18
<212> TYPE: DNA
<213> ORGANISM: Glycine max

<400> SEQUENCE: 69
tcttagtatg aaaacttc                                                        18

<210> SEQ ID NO 70
<211> LENGTH: 16
<212> TYPE: DNA
<213> ORGANISM: Glycine max

<400> SEQUENCE: 70
cttagtctga aaactt                                                          16

<210> SEQ ID NO 71
<211> LENGTH: 301
<212> TYPE: DNA
<213> ORGANISM: Glycine max
<220> FEATURE:
<221> NAME/KEY: misc_feature
<222> LOCATION: (275)..(275)
<223> OTHER INFORMATION: n is a, c, g, or t

<400> SEQUENCE: 71
tccaattccc aaaccaaaac cctcctccta gtctccaaac aaaacaaaac aaaacaatac          60
aatagctatc ttccaaccca agttgccaaa tgttcctgtc ttttcagacg cggatcctct        120

```
ccatttcaca atgtccggtt aaataaagat aaaccattgg atcatatcag tctccctgat    180
cttgccacat gtcatgctac ttttttcctt ccttttttaca ttaaaaataa aataaaatcg   240
aatgctgtaa tgtgaactta gaatgtgaaa tgaantggaa ggttgggaca acttgtattt   300
t                                                                    301
```

<210> SEQ ID NO 72
<211> LENGTH: 301
<212> TYPE: DNA
<213> ORGANISM: Glycine max

<400> SEQUENCE: 72

```
atactcgtga ttgattcaaa atgttacatt tttattgaca tattacatag acattaaatt    60
ttattactgg gcattctaat tgaattctta taaagaacta cgtacaagta agatgaaaag   120
gcatagtcct acccccacat gagattcaaa ttaaaacttg caaccaggtg atctaacagt   180
gaagctccac aagaatcaag cgcaggaaat aataccttct caaagatatt gttttttta   240 atttaatttt ttaacatgta taatacttta attttatatt atattcatta tttttattta   300
g                                                                    301
```

<210> SEQ ID NO 73
<211> LENGTH: 301
<212> TYPE: DNA
<213> ORGANISM: Glycine max

<400> SEQUENCE: 73

```
acggatcccc ttgattaagg ttcgattgta gtttctttt acaataaaac tattggtaga    60
ccacctttga ctcgaggaga gaaaaatgat ctctttgctc acaatctcct aaaagtgtaa   120
tacaaggata tgaatctttt actcctgaag attattgttg acgagagtta tttcaaccag   180
ctatgtgagc tatggtcaga agctcttgtg attaaattgc tcaacaatag tattggagtc   240
ttggttaccc cactacgctt tcaaagttaa agtctttgtg aaaaccacta cgttttgata   300
t                                                                    301
```

<210> SEQ ID NO 74
<211> LENGTH: 301
<212> TYPE: DNA
<213> ORGANISM: Glycine max
<220> FEATURE:
<221> NAME/KEY: misc_feature
<222> LOCATION: (142)..(142)
<223> OTHER INFORMATION: n is a, c, g, or t

<400> SEQUENCE: 74

```
tttccatttg ccagtaagag aggtgattat catcctgaat gataaatcta ctcattacaa    60
gtgttttcca taactttgag actcttcatg tggaggatgt cgtcttacag attactaatc   120
cgtaagttat atacaattta cngattatca atatgtaagt ttaacaggaa aaagaccaga   180
tcaaacacct tacctccgtc attaatggtc aaaccaacca ccgctacaac cgccacttac   240
ccacgaacca ctataaacaa tgcacctcca ccaaagagga cacaacaacg aatgagcaac   300
t                                                                    301
```

<210> SEQ ID NO 75
<211> LENGTH: 301
<212> TYPE: DNA
<213> ORGANISM: Glycine max

<400> SEQUENCE: 75

```
atgtgggtgg cccaatgaca acatcctctc acacctcgga atagacattt tgaatggaga    60
caagtatggg tggcccaatg acaggtctag gataggttct gatatcatca tataacatgg   120
gattatggca atctaagtca aaccccacaa aactagcttg taaagtgagg attgtccaag   180
ttttataaaa accacattga tcatatctct agttgatgca caccccttca taaacactaa   240
gactggacat ctaaagcttg ggaaaatgtt ggtggcccta taacaacatc ccaacactta   300
g                                                                  301
```

<210> SEQ ID NO 76
<211> LENGTH: 301
<212> TYPE: DNA
<213> ORGANISM: Glycine max

<400> SEQUENCE: 76

```
gaaagatatt acacaatcaa ttatcaaaca acaaattgg ctccatagat ggatgcttca     60
ccaaaggtac acacaattgt acacaataaa acagaaaat acacatctaa agagaatgta   120
cttcataatt ccactaaatg tattttaat gctagtcaaa ggcacaaaat caggaagctt   180
atcatgaaat cctacattgt attcctgaga taaagaaaaa tgcttactgg cacccacac   240 aacagaacac cttcatttgc tgattagtgt ccagaagaca tattgcaaat ggctactcac   300
g                                                                  301
```

<210> SEQ ID NO 77
<211> LENGTH: 301
<212> TYPE: DNA
<213> ORGANISM: Glycine max
<220> FEATURE:
<221> NAME/KEY: misc_feature
<222> LOCATION: (63)..(63)
<223> OTHER INFORMATION: n is a, c, g, or t
<220> FEATURE:
<221> NAME/KEY: misc_feature
<222> LOCATION: (286)..(286)
<223> OTHER INFORMATION: n is a, c, g, or t

<400> SEQUENCE: 77

```
ttatgaaata tctttgtctt ataggatgaa gcttcttata ataaaggta tgagatgatt     60 ttnattttaa ataaaatatt tcttttttc tttaaaagaa aaacttaaat ctatatctct    120
ttaacattac aaatagaagt atacctgaga caagtatacc aggttgggat ctgggtgtgg   180
atacgcataa agttttgca ttgttgaaga aaaattttgt tgcttcaaga atgcatatcc    240
gggtacataa aaataaatca taattttcac tgcaagtgtt ggaaanattt ctatgtaacc   300
a                                                                  301
```

<210> SEQ ID NO 78
<211> LENGTH: 394
<212> TYPE: DNA
<213> ORGANISM: Glycine max

<400> SEQUENCE: 78

```
cgagagtgga atagaacaaa gaagatgagc ggcgccagca gcactataag gctatcgccg     60
atggtgagcg tgtccccgaa ttgcaattgc tcatcgatga tggtgatgaa gaagacgacg   120
acggcggtgg ctcctttgtg gatgaaaagc aagagcgcta ggggtggtat taggtgcgag   180
gtggctatta atgcggtgga tgagtcgacg acgtcaccgg agtcgaagat tggagcgcgt   240
gtgaaggtga aggcgggtgt aaaggtgtac cacgtcccca aagtagccga gcttgacctc   300
```

```
acgggtctgg aaggcgagat caagcagtat gttggcctct ggaacggtaa gcgaatctcc      360
gccaatcttc cttacaaggt tcagtttctc accg                                  394

<210> SEQ ID NO 79
<211> LENGTH: 301
<212> TYPE: DNA
<213> ORGANISM: Glycine max

<400> SEQUENCE: 79
atacaagaac tagattttga ctataacttc aacatccctc ggcccaaata agttgtgaat      60
tatacttaaa ttccatgtcc cagtagcaat gtctacaata tttgcaacga ccaacttctc     120
tgccccttgc acaataggag tctcaatgta agggtttcct tcgaaccttca accaaggatc    180 agaccacatg ttgacttcct taccactacc caacctccac cgaagtccct ctttcaacac     240
cacttgcgag gacaacaaac ttcaccaaac aaatgaaggg ttatgcccta taacttgac      300 a                                                                     301

<210> SEQ ID NO 80
<211> LENGTH: 301
<212> TYPE: DNA
<213> ORGANISM: Glycine max

<400> SEQUENCE: 80
tccaccgaag tccctctttc aacaccactt gcgaggacaa caaacttcac caaacaaatg     60
aagggttatg ccctaataac ttgacaccca taaaataccc tcttggggta atatttggat    120
atgaaaatac gtgatggcaa agtgccctgt tccgatacca acctccaggc ttgcttacct    180
agcatagcaa tattgaaagc atgcaaatta caaaaccccg ttccccttttt ctccatcctt   240 ccacattgtt tatcacatga aatccaatct ataccttttg aatctcgttt ccctccaccc    300
c                                                                     301

<210> SEQ ID NO 81
<211> LENGTH: 301
<212> TYPE: DNA
<213> ORGANISM: Glycine max
<220> FEATURE:
<221> NAME/KEY: misc_feature
<222> LOCATION: (122)..(122)
<223> OTHER INFORMATION: n is a, c, g, or t

<400> SEQUENCE: 81
tgaaagtgga caaacatca gagttcaaaa aacagatttg ccgaaggata cgattgcttt     60
tacaaaatac taagaatat tagaatgatt gaggctacac cataaaatca tcaaaagaac   120
antaattaat aaaataaaaa gagaaggatt atcttatagg gaggaggaaa tggaagtgtt  180
aaaactagca gcaacacaag agacaggatg actgtataag atgaattcat atgatataat  240
tcatttagcc tatcgtcgaa aacttgcaac aacgatagca aatatccaac acaagattat  300
t                                                                     301

<210> SEQ ID NO 82
<211> LENGTH: 301
<212> TYPE: DNA
<213> ORGANISM: Glycine max

<400> SEQUENCE: 82
ttatacataa ccgcttagaa tgttacatgg tggcagtttt ataattaaaa agaataattt    60
tttttatgac acagattcta agacggtttc acggaaccgc cttagaatgt cctagggaac   120
```

```
acaaacgaca ccgggttttt attcaaaaac gtcgttgctt ttgtgtggca tgtgctttaa    180
tttcaaatcc atagcttctt tgactcttca ttttctccgt ccactctttc cctctattct    240 ttttttctc ttcctagctt tgggtctgg agcttgatct ccactccatt tgtcggagcg    300
g                                                                    301
```

```
<210> SEQ ID NO 83
<211> LENGTH: 301
<212> TYPE: DNA
<213> ORGANISM: Glycine max

<400> SEQUENCE: 83
aagttattca gcgaccttgt aatttggctc aagcatacaa agataatggt ctcatgttta     60
aatctctctc ttcttctaat tcgggtgcct ccaacattga tggtatttgc tggaaatctc    120
ctaagcatga ccaggttgcc cttaattgtg atgttgtggt cattcaatta gggaaccaag    180
ctgcttatgg tggggctatt tgagatcatc atggggcttt tatttgtaat tttcatgcca    240
aaaatgggtc ttgtgctgtc atttatgcag aactttgggc cattcttttg gcataaagt     300 t                                                                    301
```

```
<210> SEQ ID NO 84
<211> LENGTH: 301
<212> TYPE: DNA
<213> ORGANISM: Glycine max
<220> FEATURE:
<221> NAME/KEY: misc_feature
<222> LOCATION: (115)..(115)
<223> OTHER INFORMATION: n is a, c, g, or t
<220> FEATURE:
<221> NAME/KEY: misc_feature
<222> LOCATION: (124)..(124)
<223> OTHER INFORMATION: n is a, c, g, or t
<220> FEATURE:
<221> NAME/KEY: misc_feature
<222> LOCATION: (132)..(132)
<223> OTHER INFORMATION: n is a, c, g, or t

<400> SEQUENCE: 84
cttaaaatat gcttcaggct tgataattca atataaaagt aaagaaaatg gggaaaacat     60
ttcaatgtca tccctgaata aactcattct tatttaaaat tatggcagca acaanatcca    120
aaantgaaaa anaaagtgtc atgggatggt tcttcaatta atcttttact tttattttg    180 cttttaaagt gccacgaaaa aaacattatt cttttgtcat tgtacaggtc caaatctatg    240
caagaactct cacaaaatta cattgcacag gtcgacatct attaagagtt tacaaaataa    300
t                                                                    301
```

```
<210> SEQ ID NO 85
<211> LENGTH: 301
<212> TYPE: DNA
<213> ORGANISM: Glycine max

<400> SEQUENCE: 85
attctgccat agcattttgt atactatatc caaactttag aacatgcttg aaaactattt     60
gcaattacat taaatcatgg aaggcaacaa gtactgaaat gctatttgca attatatgtc    120
attctgcgga ttgcttttgt aactctagaa gaactaatgc aacatagaat taatctacaa    180
taagcactgt atttctccat agctctgtag agagaatgtt gggcttctct agaagtttgt    240
caacatcatt gagcacaagt attgatatag aataaaaatc aaacgttgag aattctttta    300
``` a                                                                           301

<210> SEQ ID NO 86
<211> LENGTH: 301
<212> TYPE: DNA
<213> ORGANISM: Glycine max

<400> SEQUENCE: 86
ctctcttttt gtatacaaga aatagactaa gactcaaagt catgacttaa ataaatccta      60
ctcttgtaca tccttttcta caactcataa agtatcctta aagggtccta ctttcctcga     120
acaagtccat ccttgtcctt agtatttgtt gtcgcatttc catcatttct gtacaatcac     180
acaaaattat ctgtcttctt ttgaaaaatg aatgattat ggagtgagtc tctcgcctcc      240
tctaaaacca caaacaaaat gagcttgagg tctcacaaca atcattaac cttgtgattc      300 t                                                                           301

<210> SEQ ID NO 87
<211> LENGTH: 301
<212> TYPE: DNA
<213> ORGANISM: Glycine max

<400> SEQUENCE: 87
acacgcggag atttacatcg tcatccgcgc ttgctgtaat cctgacctat gaattctgat      60
gacgtacgga gataccccga gtggttatcc gtacaaagac aatttctatt aatactaacc     120
cgtgaagttg ggtggcaggc taagagaccc aagtggttat ccgtataaac actctttcgc     180
tattcgtaac tctcaaagca cgataaaatg tagagactaa cttcttcgtc tccacccttt     240
gtaaatcgcg gccaatgagc ccgttgacac catgagattt acttcgtctt tcgcgctttc     300
t                                                                           301

<210> SEQ ID NO 88
<211> LENGTH: 301
<212> TYPE: DNA
<213> ORGANISM: Glycine max

<400> SEQUENCE: 88
gccaacatgt ctgtaggaca aagtctttat tacctttacc tacgcatttt taacatttag      60
tgatggtttt tgtccgtagg cataagtcat ttttcttgta gtgcgatata gtctacctat     120
aaaaatcaag ttaatgtgaa aactttactc tattgacaaa tcatcttgtc acccaggccc     180
taactatgat atggatcggc taaacatcaa ctctacattt gacaaattcc tcagcttcat     240
ttgtttatca caatggatac atactaacaa atgaataagg agtatacttc aagtcttcct     300
t                                                                           301

<210> SEQ ID NO 89
<211> LENGTH: 301
<212> TYPE: DNA
<213> ORGANISM: Glycine max

<400> SEQUENCE: 89
tagagctttc gaaggaaaat aagttgtatg ctaaggtgtc taagtgtgaa ttttggttaa      60
gtgaatttaa atttccagga catgtgatat ctgctgaagg gatagttgtg gatccaacaa     120
aagcggaagt tgtgttgcaa aagacctaag aaaattacga ttataagagg ctttattggt     180
ttcacaaaat attgtagaag atttatgaaa ggattctcga ggatagtttc tcctttgacg     240
cgactaactc ataaggatca accttttata tggttagaag agtgtgagaa gagattccta     300

| | |
|---|---|
| g | 301 |

<210> SEQ ID NO 90
<211> LENGTH: 301
<212> TYPE: DNA
<213> ORGANISM: Glycine max

<400> SEQUENCE: 90

| | |
|---|---|
| tctagggttt tcaactaac ccttcttact tctcttctct ctacactttg agcttggaca | 60 |
| ttagatgaaa ttgtttgttt tgtgtgtgtg tgtttgtttg ttttgtgtg tgtgcacgtg | 120 |
| cacgcgcatt tgatccatgt gaatataagg ggagaatgag tgtgttttgt gtcaacatgg | 180 |
| actcaggttc aagagacata agtgaggata atttaggaaa taacaaaata ggtcaagact | 240 |
| taatgaagaa attgttgtaa aatttgaatt ttagtgtctc tcccgatgag atatttcagc | 300 |
| c | 301 |

<210> SEQ ID NO 91
<211> LENGTH: 301
<212> TYPE: DNA
<213> ORGANISM: Glycine max

<400> SEQUENCE: 91

| | |
|---|---|
| ccatgtatca tacaagtcgt ttgttaactg atccaagact tctctcacat ggcttagtct | 60 |
| ttgtcgattg gtttttgata agtccttact aataacggta aaccattctt ataaccccc | 120 |
| cggagctata ataattgccc aaaaaccatt ataagcacc tataataatg attagctagg | 180 |
| agttaaaggt agaggcgacc acttgaaagc ttaggaggag gccgtgtcta taagaacccc | 240 |
| gaggacaaag ttgagaaggt agattatagt agtctcaatt gaatgctttt ggactaggta | 300 |
| t | 301 |

<210> SEQ ID NO 92
<211> LENGTH: 301
<212> TYPE: DNA
<213> ORGANISM: Glycine max

<400> SEQUENCE: 92

| | |
|---|---|
| aagctcttat acatgacttc ctatggtggt gagcttgttc ttgactcatc ttttccttga | 60 |
| agtgacttct ctaatcacct ttcctccttc tccattctgc tatcattgat tttcaagaag | 120 |
| caaaggactc cattgatgaa gaacatccaa ggcctacaag ctctacatgg agctacatca | 180 |
| gtaatggtat tacatttgta ttccccattc atttttgaa ttatcaattg gtaataacca | 240 |
| tataggatgt tgaatccaca tccttggttt taattatgac aaaccattag caatgcaaat | 300 |
| t | 301 |

<210> SEQ ID NO 93
<211> LENGTH: 301
<212> TYPE: DNA
<213> ORGANISM: Glycine max

<400> SEQUENCE: 93

| | |
|---|---|
| catcaaccat ggttggccta tcagaaccaa cttcttgcaa tcattttct attgtctcac | 60 |
| taaatttcct tagtgagttt tcatctatat ggtccttcat ggaaggatca attatccttt | 120 |
| ggagcatccc cttgttttc caagcattc cccattaaac caagtttatc tgttctgctg | 180 |
| gaagcaatgg atcaagggtc agtcttgcac ataacacttc caaagagct accccaaatg | 240 |

```
attagacggt aaaatttcga gggtttccta gattcacaat tataggaaac taacagaatc    300
t                                                                   301
```

```
<210> SEQ ID NO 94
<211> LENGTH: 301
<212> TYPE: DNA
<213> ORGANISM: Glycine max

<400> SEQUENCE: 94
tggattgtag tcacgaacaa gaaaaacatg tgtttcccca tatgcgggga gtttccaagt     60
gaaacactgg ggttttagaa tttatgaaga ctaatagagt tatgctcctc caataatggc    120
cacatgaatg aggacccgat tgggttgcta gttgctatag ctacaattgg agttttgaga    180
agcgattggc tgattgactc atacgttcaa caaaaggcca gtgcagtctg cagacccctt    240
taccctcaac cccactgcac tatcaaccgt gaacattttc gtggtaggga atacttatgc    300
a                                                                   301
```

```
<210> SEQ ID NO 95
<211> LENGTH: 301
<212> TYPE: DNA
<213> ORGANISM: Glycine max
<220> FEATURE:
<221> NAME/KEY: misc_feature
<222> LOCATION: (123)..(123)
<223> OTHER INFORMATION: n is a, c, g, or t

<400> SEQUENCE: 95
atacaaaaat ctttaactaa tgttcttaaa aaactgatta acatttgtaa ataaagaatt     60
tgatagtacg aaaacacttg ttttgtgtgt gattttaaaa tttaggcgtg agataacaca    120
aangaagcac aggatataag taaaatgaac aaactactta ctgaactgat agcttcttat    180
cccacaacaa tttcacccaa tccttttcac ctgttcaata aaactaactt tctctccact    240
ttgcccctcg taaaaaaatg tttgggttcg tttgacaatt gagttttata agaaaataaa    300
a                                                                   301
```

```
<210> SEQ ID NO 96
<211> LENGTH: 301
<212> TYPE: DNA
<213> ORGANISM: Glycine max
<220> FEATURE:
<221> NAME/KEY: misc_feature
<222> LOCATION: (72)..(72)
<223> OTHER INFORMATION: n is a, c, g, or t
<220> FEATURE:
<221> NAME/KEY: misc_feature
<222> LOCATION: (113)..(113)
<223> OTHER INFORMATION: n is a, c, g, or t
<220> FEATURE:
<221> NAME/KEY: misc_feature
<222> LOCATION: (159)..(159)
<223> OTHER INFORMATION: n is a, c, g, or t

<400> SEQUENCE: 96
acaaattatg agaaaaaaga ctatgagatg atagtataga ataattttat attatcattc     60
aattacattt tntaatttat gataagtttg ttaaatttta taaattatt ttnaaagtta    120
aatcaacatt aatttgtaat tagaataata atataaaant attttacatt gtgaataatc    180
ataattaaac ttataaattt tattgaaaaa tttaaagtcg tgtggtgtgt ggtggttgtc    240
gacgtcaact ttatattgta gaaataatta aaggaataac tcagtttaaa tcaattttac    300
a                                                                   301
```

<210> SEQ ID NO 97
<211> LENGTH: 301
<212> TYPE: DNA
<213> ORGANISM: Glycine max
<220> FEATURE:
<221> NAME/KEY: misc_feature
<222> LOCATION: (4)..(4)
<223> OTHER INFORMATION: n is a, c, g, or t
<220> FEATURE:
<221> NAME/KEY: misc_feature
<222> LOCATION: (195)..(195)
<223> OTHER INFORMATION: n is a, c, g, or t

<400> SEQUENCE: 97

```
atgnccttttt agtggaaata aattttgtt gaacaagtct tcaatgaaat cgtattttca      60
ttgcatacaa taggagcgaa aaaaaataaa gcaacaaaaa tggaaatgca attttgttgt     120
acatcatgca acgaaattat atttctatta ctttattttt tttacccctt tgtgtgtaac     180
aaaaatacga ttctnttgta cactgtgcaa caaccaaatt gcatttctgt tgttggctcc     240
taccagcaac aacacagatt ctcccaccat aatcaccatc ccaaactcat aacaacaac     300
a                                                                      301
```

<210> SEQ ID NO 98
<211> LENGTH: 301
<212> TYPE: DNA
<213> ORGANISM: Glycine max

<400> SEQUENCE: 98

```
agatggtaaa gagacatcta acagtgatgc tcctgagaac aatcctcagt atactactgt      60
ttatgtgggt aaccttgctc cagaggtaag agcttttctt gtgtttttta attttaatt     120
tacatttaga acaataccat ttcatcaact gttatttgat tgaaaagttt gcaaacttat     180
aatttttgaa gtccattact tatattggcg ttgccaaatt ttacattacc tctatcatct     240
tgtttgttct ccttatctct tttggctatt atgtatactt gtgcgttatg ttttgaattc     300
t                                                                      301
```

<210> SEQ ID NO 99
<211> LENGTH: 301
<212> TYPE: DNA
<213> ORGANISM: Glycine max
<220> FEATURE:
<221> NAME/KEY: misc_feature
<222> LOCATION: (45)..(45)
<223> OTHER INFORMATION: n is a, c, g, or t

<400> SEQUENCE: 99

```
atgatggctt tggaagagaa atttgacatt tccattggag agggnggagc tgagaacatc      60
tccaccgttc aagatgctgc tgatctgatt gagaaggtga cgaatgcttc aacctaagcc     120
aagctgcgtt cacatcatag ctttcatcac tatcctttt agattttgac aaaaattgat     180
tcaatagaat gcttaatttc aagtgggttg tcacatctcc acatttactt agtttcctcg     240
aataaaagtg gctagctctt aagtcttttg aattgaaaag attgattgct tgaggccata     300
a                                                                      301
```

<210> SEQ ID NO 100
<211> LENGTH: 301
<212> TYPE: DNA
<213> ORGANISM: Glycine max

<400> SEQUENCE: 100

```
gtcctcaatg tgtaaaccag tcatcctcgg tgctctccca aagggaaata ttgatgcagg    60
aaacaaactg gacgggtttt tcctccaaaa gaaagatttt tgagttcgag tacaactttg   120
gtggcaacat ttgtgatatg tgtttatgt tcgtaaacga acacaacatg ggtacttatt    180
tcgagtctac ctacaaccac aagagttatg ttgctaatga tgtcttttg ttttattctt    240
tttctgctgt ctttatttca tcttttcca aaagaaaac tctcaaacct taaacctggc     300
a                                                                    301
```

<210> SEQ ID NO 101
<211> LENGTH: 301
<212> TYPE: DNA
<213> ORGANISM: Glycine max
<220> FEATURE:
<221> NAME/KEY: misc_feature
<222> LOCATION: (5)..(5)
<223> OTHER INFORMATION: n is a, c, g, or t

<400> SEQUENCE: 101

```
cccgntctgg gctcttatat tatatgggtt atcactatat ctaattgaag ataagattaa    60
tgttcgtctt gttttcacc tcttaatcgt aaatgcatac tttgaagcac caacatgaag    120
gcccacaacc accgctatct ttaccttgta ggcttgcacc atgctatttt ggtcaaacac   180
attaattcat gcttcctatg acaaaaattg atcacccatg ttgtatatat tacatgagta    240
atatcagagg atgaagccac aaaaatacat tagtcacatc ttattatttt ctttctctt     300
a                                                                    301
```

<210> SEQ ID NO 102
<211> LENGTH: 301
<212> TYPE: DNA
<213> ORGANISM: Glycine max
<220> FEATURE:
<221> NAME/KEY: misc_feature
<222> LOCATION: (117)..(117)
<223> OTHER INFORMATION: n is a, c, g, or t
<220> FEATURE:
<221> NAME/KEY: misc_feature
<222> LOCATION: (277)..(277)
<223> OTHER INFORMATION: n is a, c, g, or t

<400> SEQUENCE: 102

```
tgatgcatcc gcgaatttga attctcagta cgacaagccg tgtacatttt attgggaatc    60
ttagaagaac taggtgagct aaaagttttt acatctatac attatggtca aattttntta   120
tttttatttt tcactgtctt ctgtcaaact agacaacatt ggttaattaa caaaaattag   180
ttccattaat aagaatgaaa ttcacatctt aacaagaatg tagactccaa tcccactggc    240
aatgcaagaa ccttgttaat aaatgatcga taaatantt tataaaatac ttaatgagta     300
t                                                                    301
```

<210> SEQ ID NO 103
<211> LENGTH: 301
<212> TYPE: DNA
<213> ORGANISM: Glycine max
<220> FEATURE:
<221> NAME/KEY: misc_feature
<222> LOCATION: (74)..(74)
<223> OTHER INFORMATION: n is a, c, g, or t

<400> SEQUENCE: 103

```
ttaaatctac attttcattt gaatcttta cttttcttta tcaaacttga ttgtacttag     60
```

```
taacaactta catnctggga caaccacata acatggtgaa tggttttaaa atcaaaatat    120
taatatattt aacttcatat ctcgtgatta tctggtctta aattgaatta aactcgaccg    180
caatactggt gcaatttgtt atcacaaagc ataatccaca accctgaaaa taacaattga    240
gagccatcgc gccattgcac tgattgtatg tgtttttgtg tcgtggttat gtagtaccat    300
c                                                                   301

<210> SEQ ID NO 104
<211> LENGTH: 301
<212> TYPE: DNA
<213> ORGANISM: Glycine max
<220> FEATURE:
<221> NAME/KEY: misc_feature
<222> LOCATION: (64)..(64)
<223> OTHER INFORMATION: n is a, c, g, or t
<220> FEATURE:
<221> NAME/KEY: misc_feature
<222> LOCATION: (81)..(81)
<223> OTHER INFORMATION: n is a, c, g, or t
<220> FEATURE:
<221> NAME/KEY: misc_feature
<222> LOCATION: (95)..(95)
<223> OTHER INFORMATION: n is a, c, g, or t
<220> FEATURE:
<221> NAME/KEY: misc_feature
<222> LOCATION: (209)..(209)
<223> OTHER INFORMATION: n is a, c, g, or t
<220> FEATURE:
<221> NAME/KEY: misc_feature
<222> LOCATION: (217)..(217)
<223> OTHER INFORMATION: n is a, c, g, or t

<400> SEQUENCE: 104
tgaaaataga ttgactttta gaattaaatt tacaaaaaat cattcttttt atattgaact    60
ttcnattatg aaactcaatg ngaatccttg cactntaatg gactttctat agactctcaa    120
acaccaatcc ttgaatgaat tgttagggtt gttgcttcct gcatctctta gaaagaattg    180
gtgatgggtg gttactttta agttattant acgacantct aacaatgtta aaaaaaattt    240
ctaaggtcga ttatgataaa aaaataatta acatcgatat atatatatat atatatatat    300
a                                                                   301

<210> SEQ ID NO 105
<211> LENGTH: 301
<212> TYPE: DNA
<213> ORGANISM: Glycine max

<400> SEQUENCE: 105
ttaactagcc cactccttaa ataatacaaa attaagaaca ccaccttaca aattgtgtat    60
tttttgtgtg gagatgtatg ctctacaaag gggaaagcat acaaaagttg agatgcataa    120
gttaacttgg attcatttta tttccctacc atacacaagt cacctctttg agttatattt    180
ttttatccat ataaatttag agagagaaga tggtgtttca gtccaagtct ccaagataga    240
aaaagtgttt gggctgaaaa cacatttcta aaggtactta catttacctt atccaaaaaa    300
a                                                                   301

<210> SEQ ID NO 106
<211> LENGTH: 301
<212> TYPE: DNA
<213> ORGANISM: Glycine max

<400> SEQUENCE: 106
```

```
gagttaattg ttttttattg tttgggggg ctttttgtcc ttgaccttgt cttttgtgat    60
ctctctctcc cactattgaa cattgaacaa cgataataat ataaaagcac gttagtaatg  120
atgcaaatga cagtgacatg atgactttcc tactgttcat catgttacgt gtgtcatgtc  180
actacgcctc tgtcgttaac tgtcaagagt acatgaagct agaggtgttc ttgttctatg  240
gaggaacaaa aataatctaa tttaattatt gtagttttgt tattttattt gattttgaat  300
t                                                                  301

<210> SEQ ID NO 107
<211> LENGTH: 301
<212> TYPE: DNA
<213> ORGANISM: Glycine max
<220> FEATURE:
<221> NAME/KEY: misc_feature
<222> LOCATION: (289)..(289)
<223> OTHER INFORMATION: n is a, c, g, or t

<400> SEQUENCE: 107
ttcttcttta agaaatgcta gtaacatatt ttccataaca ctcttttaaa cacattatta   60
atggttgaaa tttgttggaa atcacaaaat tatttggtgg gtttcacttc ttatttaacg  120
agtttcactc gtaatttgta gtttcttata cattttactc aataatatag agtttgatag  180
aagtagtgta ttcaagagtg agtggttagc agtagcactc gtattttct tccagtgtca   240 ttatgattcc atttaataga atctctttaa tcaatatcaa atgtcacant gcattttgta  300
a                                                                  301

<210> SEQ ID NO 108
<211> LENGTH: 301
<212> TYPE: DNA
<213> ORGANISM: Glycine max

<400> SEQUENCE: 108
tttaatgatg tattatataa taatcaattt ttttcacaa atcaactgt attatcaatt     60 aaaaatattt ggggtaaaaa tatactactc gttgagttaa aaatattttc ttttttgtttg  120 agaaggaaag cttttacgaa tcggggtaat gattacgaat accgttgttc agtgactagg  180
ggaggtcaca tgtatgagac aatgagggat gaaatcaata cgtagaaaat gtaaagttta  240
attatttagt ttttattatt acatcaactt aattttcgt tttaattcat atacctaaga   300
t                                                                  301

<210> SEQ ID NO 109
<211> LENGTH: 301
<212> TYPE: DNA
<213> ORGANISM: Glycine max
<220> FEATURE:
<221> NAME/KEY: misc_feature
<222> LOCATION: (44)..(44)
<223> OTHER INFORMATION: n is a, c, g, or t
<220> FEATURE:
<221> NAME/KEY: misc_feature
<222> LOCATION: (260)..(260)
<223> OTHER INFORMATION: n is a, c, g, or t

<400> SEQUENCE: 109
aatcaagctg atcaatccac aaatacaaat gcttcttcgg atgntgtaga gaaagtgaat   60
aatgccagaa gcatacctgt gaagcagata gaatcccacg aaggaaaaaa tgtttctctc  120
gatcaaatgg aagagaatgt gacacaaaag gactcttgca ctggggacaa aaagagacaa  180
tctacatctt cacctaaagg atccaagtta cctccggttt gtctgagagt tgatccacta  240
```

```
ccaaggaaga aaaatggccn cgggagttcg agttcgaggt ccccaagtcc accttcatca      300
a                                                                     301

<210> SEQ ID NO 110
<211> LENGTH: 301
<212> TYPE: DNA
<213> ORGANISM: Glycine max
<220> FEATURE:
<221> NAME/KEY: misc_feature
<222> LOCATION: (2)..(2)
<223> OTHER INFORMATION: n is a, c, g, or t

<400> SEQUENCE: 110
tncatcagtt atttaactct caacaagtta caagagaaca attttcttag ctgacaaaat      60
gaacttagtt tacctggaga acattacaaa ctccataaag gatcttgtag gcatagccca     120
actctgcatg acagaccatg tgtcaccatc taccggcatg ggaggcaaag aatccgcatc     180
accttttacc ccatacattc tcctcatggc ttctgagaaa gcaaaccttc actcaaacac     240
aaatgaagag aaaatcaagc tatatcttta aaaatgtaaa aggtaacgaa aagcaaagat     300
c                                                                    301

<210> SEQ ID NO 111
<211> LENGTH: 26
<212> TYPE: DNA
<213> ORGANISM: Glycine max

<400> SEQUENCE: 111
attacgaata ccgttgttca gtgact                                          26

<210> SEQ ID NO 112
<211> LENGTH: 38
<212> TYPE: DNA
<213> ORGANISM: Glycine max

<400> SEQUENCE: 112
atcttaggta tatgaattaa aacgaaaaat taagttga                             38

<210> SEQ ID NO 113
<211> LENGTH: 19
<212> TYPE: DNA
<213> ORGANISM: Glycine max

<400> SEQUENCE: 113
tcatccctca tagtctcat                                                  19

<210> SEQ ID NO 114
<211> LENGTH: 18
<212> TYPE: DNA
<213> ORGANISM: Glycine max

<400> SEQUENCE: 114
catccctcat tgtctcat                                                   18

<210> SEQ ID NO 115
<211> LENGTH: 301
<212> TYPE: DNA
<213> ORGANISM: Glycine max

<400> SEQUENCE: 115
taaccctctt ctcttgaact aaccttccga agtaacttag acttagtccg tttctaatat     60
```

| | |
|---|---|
| aattgattca ttttcaatgc gcacaaactc aaaatgatcc cccaagtttc taccttaatt | 120 |
| ggtggtttat attacggtgg cagtaactga atcagaatca tagagagaac aaatcatttt | 180 |
| caggagtttt ggtaggtttg aactctccca cagcaaccta aattcctctt aaatcacacg | 240 |
| atcaccctct cagtcttttt tcttatttat aagcaacatg ccttattttt ctaattatcc | 300 |
| t | 301 |

<210> SEQ ID NO 116
<211> LENGTH: 301
<212> TYPE: DNA
<213> ORGANISM: Glycine max

<400> SEQUENCE: 116

| | |
|---|---|
| agaaagaggt gaatgggtcc gtgttcactt taattaattg gtacttgatt attaaagatt | 60 |
| ttccattttt tggtatagga gtacttgggg agttcggtgt ttttttttctt cttttttttta | 120 |
| ttaaagggag gctatagcca ttacaaacga ataactctag ggaaacaagt tcccatacaa | 180 |
| tcactccaaa gcaaaccctt acaatctaca ggaagtagcc cgaaaatgtg cactcctata | 240 |
| gggatgtcaa gacccttggc tgccaaacaa tcagctacat tatgcaacat tgtttcctg | 300 |
| a | 301 |

<210> SEQ ID NO 117
<211> LENGTH: 301
<212> TYPE: DNA
<213> ORGANISM: Glycine max

<400> SEQUENCE: 117

| | |
|---|---|
| aatttacaag tattaagcta tatttggaaa ttaattatat ttggtaatt tttaataagc | 60 |
| ttaataacaa gtttgaaaca tatgtggcat accataatga tgtttggttt ttttaagttt | 120 |
| cacttccatt ctacttttag ccatagagaa aggagagaag gataatgaaa gttggtctaa | 180 |
| agggtatgaa aacttagcgg taaataaggt tatagaaatt gcaagaccgg aaactgacac | 240 |
| gttcctaaaa tagaaacagc tgaaatgtct ctcgtccaca ctccattgca agaaaccac | 300 |
| g | 301 |

<210> SEQ ID NO 118
<211> LENGTH: 301
<212> TYPE: DNA
<213> ORGANISM: Glycine max

<400> SEQUENCE: 118

| | |
|---|---|
| tagaaccagc atttcctgac cagaatacac aaaagtttaa gagagaaaaa ttagaacaga | 60 |
| atacaagctt gaattcatta atatcatgga tttttacaaa ttgaattgta aattaaaaaa | 120 |
| ttagtatttt tttaatttgg aaaagttttt ttatgtatat ataagggaaa taaacaaaa | 180 |
| gctaaacatg aataaaataa tcccctataa catccgttag aagaaggaaa caaaatgtca | 240 |
| ggaatagaag aactctaaga aatgaaatca catctcgaga cgcgcggaaa tttggaatga | 300 |
| a | 301 |

<210> SEQ ID NO 119
<211> LENGTH: 121
<212> TYPE: DNA
<213> ORGANISM: Glycine max

<400> SEQUENCE: 119

| | |
|---|---|
| tatgtattaa tctatatgag catatagatg tccaataggt acataggtta aaagatgaca | 60 |

```
aaacaagtta gacccatgca agataacycg tctagttact aaataaaatg ataggggtgg    120
a                                                                   121

<210> SEQ ID NO 120
<211> LENGTH: 300
<212> TYPE: DNA
<213> ORGANISM: Glycine max
<220> FEATURE:
<221> NAME/KEY: misc_feature
<222> LOCATION: (52)..(52)
<223> OTHER INFORMATION: n is a, c, g, or t
<220> FEATURE:
<221> NAME/KEY: misc_feature
<222> LOCATION: (144)..(144)
<223> OTHER INFORMATION: n is a, c, g, or t

<400> SEQUENCE: 120
taaagcaatc aattcaacgt ctatttattt tcattgacgt agggttttct tnttcactct    60
tgaaaaacag agaaatagat cgtacgagtt tagtttaatt tacttaaaaa attaaaaata    120
tattttccta aattatttt tttnaaaata gttatcttaa tactcttta cctattaagc     180 tttacaaagt gatataccaa atagaatatg tttggaaaat ggttcaaccc ctttaaccgc    240
caatgaccag tgaaagtggc aatgtgtctc cgaaagcgaa aaacactaaa aaccgaacac    300

<210> SEQ ID NO 121
<211> LENGTH: 301
<212> TYPE: DNA
<213> ORGANISM: Glycine max
<220> FEATURE:
<221> NAME/KEY: misc_feature
<222> LOCATION: (157)..(157)
<223> OTHER INFORMATION: n is a, c, g, or t
<220> FEATURE:
<221> NAME/KEY: misc_feature
<222> LOCATION: (265)..(265)
<223> OTHER INFORMATION: n is a, c, g, or t

<400> SEQUENCE: 121
ctcttttaat gattttttt ataattaaac aaagaaaaac aaagactggc cacatataag     60
aatatattta attaacagcc gaagactaca actctcattt agaagcatat gaactattaa    120
aatggaattt aaatgtctta atagagtttt ttttatncac ataattataa aataactata    180
atcaatatat tacagatact caacatgatg tcacacccttt caagtttcca atgagatcaa   240
actctgcgtc aaaaaaaaa aaaanagaga tcaaactcat aattactatg gcaattattt    300
t                                                                   301

<210> SEQ ID NO 122
<211> LENGTH: 301
<212> TYPE: DNA
<213> ORGANISM: Glycine max

<400> SEQUENCE: 122
aataaaaaaa aaacaaaaac tgattattta attatctctt tcttacactc ttgcaccata    60
tatttccatt ggtgttgttc ttgtatctct gtattgtttt taaattttag gattatgcaa    120
tgaattattc agaattaaga gatgaagaga atacgttgat attgtacgca gaggctgaag    180
aattagatac gtggtagtgt aatataagct agaacgggta gttggcttaa tttaaatgcc    240
tttgtaataa ttggctgtac actgaaatga ccactttggt tggtgaatac ttaagttttt    300
c                                                                   301
```

<210> SEQ ID NO 123
<211> LENGTH: 301
<212> TYPE: DNA
<213> ORGANISM: Glycine max

<400> SEQUENCE: 123

```
gagataaaaa aaaataatta ttaaaatgat cttttatctt taaaaaaaat aaatgagagt    60
aaaatatttg aaagactaac aaaacaaaac tatagagaaa tagctttgaa gaaccgtaat   120
ctgttgctga ataaatttat ccgcaattca cgtgtttgat agcagaaaaa gtggaaagat   180
tgcgggttgc ttttggaatc atatgatgtc cctttcggag cgtgttgcct cacctaaacc   240
cggagtcctc tgtataagtt gattccttaa tttttctcct cattcaaata gactgagaaa   300
a                                                                  301
```

<210> SEQ ID NO 124
<211> LENGTH: 301
<212> TYPE: DNA
<213> ORGANISM: Glycine max
<220> FEATURE:
<221> NAME/KEY: misc_feature
<222> LOCATION: (146)..(146)
<223> OTHER INFORMATION: n is a, c, g, or t

<400> SEQUENCE: 124

```
ttcatctatc aacatgaaac cctacattac cttctccatg ttgtcactct ctcaaaacct    60
caccgtgttt cactcagaac tctcagtgga ttctctcact caaactcaaa gaacagaaca   120
gatcaaacgc tcgactagga gaanaata tttcgtatc aacgaattat gatccgttga   180
cgaatgaaaa ttggcaaatt atgatccggt gggtcccata gtcatattca tcagtaccaa   240
gtagggttgt ataaaaatta attcgataaa taaaaaatta aactgaattg atttaaatt    300
a                                                                  301
```

<210> SEQ ID NO 125
<211> LENGTH: 301
<212> TYPE: DNA
<213> ORGANISM: Glycine max

<400> SEQUENCE: 125

```
tttaatatta ttttaataaa ataatattca ctagtttttt ttttctgaag agaatattca    60
cttttttata ttattaaatt tacttatcaa atagactgta tctaaaaaaa aatactattc   120
aaatagagaa aactaattga gtcttgaggt ttcttatcga cccttgacga ataaatatgg   180
gtactcctct caccttctct tccctttgttt tcttcttcta ttttcataga catagctaaa   240
cttgcgccaa tactgttttt ttttttacg gaaacttgca acagtaatgt tattcgcatt   300
t                                                                  301
```

<210> SEQ ID NO 126
<211> LENGTH: 301
<212> TYPE: DNA
<213> ORGANISM: Glycine max

<400> SEQUENCE: 126

```
tcattttttc ttcttatttc ctattcccct aaatatccat ggaagccaaa atgaaggttt    60
taaaaaacag tctctgccac catgatttag gtcacaacat caaggttttt taaccgtccg   120
caaccgcaat tgcgactgca ttggtccgcg atatcaacaa tttaaaaagc ttaaacaaac   180
agaactttgg atacaaaagt agcagtggtg tttcatgttt gctaactcac ctccaacaaa   240
```

```
tcatgagtcc ttctcatgtc atctctagaa agctcctcac agaagaccct caccacctcg    300
g                                                                     301
```

<210> SEQ ID NO 127
<211> LENGTH: 301
<212> TYPE: DNA
<213> ORGANISM: Glycine max
<220> FEATURE:
<221> NAME/KEY: misc_feature
<222> LOCATION: (20)..(20)
<223> OTHER INFORMATION: n is a, c, g, or t

<400> SEQUENCE: 127

```
cctatccatg taatttactn cccgccaaac cattacaaaa ctaaacaccc agctaccaca     60
ttgtctagta tggctcttaa tctcttaatt tcaatcccat tcttttttact ctttgtagtg   120 aatccatttc actttgttga gccaagaacc ttagaagtct ccgagcatcc attcaccaga   180
actctccgaa aactcaagga aatcaacaag ggacaaaggg tgagaggcgt gggcgagctc   240
aaaagctacc taaaaaaatt tggctaccta acaacaaatg acaattcttc aaacaacaac   300
c                                                                     301
```

<210> SEQ ID NO 128
<211> LENGTH: 301
<212> TYPE: DNA
<213> ORGANISM: Glycine max
<220> FEATURE:
<221> NAME/KEY: misc_feature
<222> LOCATION: (90)..(90)
<223> OTHER INFORMATION: n is a, c, g, or t
<220> FEATURE:
<221> NAME/KEY: misc_feature
<222> LOCATION: (268)..(268)
<223> OTHER INFORMATION: n is a, c, g, or t
<220> FEATURE:
<221> NAME/KEY: misc_feature
<222> LOCATION: (287)..(287)
<223> OTHER INFORMATION: n is a, c, g, or t

<400> SEQUENCE: 128

```
ggttttgcat gaaatgggtc acattctagg tcttggacat agtgacgttc acacttcggt    60
tatgtttccc actattcaag ggacaaggan ggttctaagc caggatgata ttaatggcat   120
acgagccctg tatggattat agaactagaa cttgatattg tgttaaaaaa gaaagctcgg   180
gtgtagcacg tgtgttggct acttgttaac ttggctgctg aaatgttaag ggcagagttg   240
catgtattaa tctataacta ataaccnac catgtacact tgtgatnata tccttataat   300
a                                                                     301
```

<210> SEQ ID NO 129
<211> LENGTH: 301
<212> TYPE: DNA
<213> ORGANISM: Glycine max

<400> SEQUENCE: 129

```
catttctaat attccatgtg cactgtacac cattgaactt tagaatgatc catactttga    60
ctttagaacc ttgatagata tataatacac tattgaccaa cgttggtcaa tagtatatta   120
ttaaactcct ccttcctcct ttttatcttg taaatagtgt tccaacttgc tcacaccaat   180
ttctctcatt cctcaccact accccaaggg gaccaacttt aaaaattaat gttaatctaa   240
taaatatata tccatcaaaa tctatacaaa atgttttcat atagttaaat attttcaaac   300
``` c                                                                            301

<210> SEQ ID NO 130
<211> LENGTH: 301
<212> TYPE: DNA
<213> ORGANISM: Glycine max

<400> SEQUENCE: 130
attatatcac aattccaatt taattattat gaagcaattt ttcttataat ataatttata        60
aatttaaaaa tatctattta tcttaaatta taattataat tatttaaaac aatttttatc       120
ctatgtaata ctcatgttaa aatatcactt actagatgaa atacttatgt gtgtgcatgt       180
tgttagggaa ttttcatgtg aacacatggt ccagatcgtc tccgagaaga ctagtaattt       240
caaggcaatt ccaataacaa gactaagttt ctgtaagagt atttctcaat ggtttgtgtt       300
t                                                                            301

<210> SEQ ID NO 131
<211> LENGTH: 301
<212> TYPE: DNA
<213> ORGANISM: Glycine max
<220> FEATURE:
<221> NAME/KEY: misc_feature
<222> LOCATION: (297)..(297)
<223> OTHER INFORMATION: n is a, c, g, or t

<400> SEQUENCE: 131 atttttttt aaaaaataag atatgtatct tacatgagaa attatatctt agcaatataa         60
aataatattt atttgataca taataatatc ataattaaat tataattaac taaaaataga       120
aaaaaatata aaaatgtgat ttttaaagt tttttaaaa aatttagagc aaaattgtat         180
atagatttca tacaatcaca taacactttc gggaccaaac aaataactta aagaatgtta       240
attggagatg ctctttcgag cacaacgcgg ttgaaaagtc atggcttgaa ttgtggnatt       300
g                                                                            301

<210> SEQ ID NO 132
<211> LENGTH: 301
<212> TYPE: DNA
<213> ORGANISM: Glycine max
<220> FEATURE:
<221> NAME/KEY: misc_feature
<222> LOCATION: (210)..(210)
<223> OTHER INFORMATION: n is a, c, g, or t
<220> FEATURE:
<221> NAME/KEY: misc_feature
<222> LOCATION: (244)..(244)
<223> OTHER INFORMATION: n is a, c, g, or t

<400> SEQUENCE: 132
cctttcaatt atattgaatt gttttgggca cactacttgg ctgacttcag tttcaggtag        60
gggacatgaa tttattactt ttttggtaca gacacgacta cgttacgtta ctttagccaa       120
acggattaaa taattgaatg ctaatgatgg aaaaggtcga gagtgaatca aattaccccc       180
acaaaagctt acaaattaac ttaagggaan aaaattcata acgaatgaaa ttcgactcaa       240
tgtnaaaagt ttgtttgact aatttacaac aatttgagaa actgatcata aaaaaggtg        300 a                                                                            301

<210> SEQ ID NO 133
<211> LENGTH: 301
<212> TYPE: DNA
<213> ORGANISM: Glycine max
<220> FEATURE:
<221> NAME/KEY: misc_feature
<222> LOCATION: (61)..(61)
<223> OTHER INFORMATION: n is a, c, g, or t
<220> FEATURE:
<221> NAME/KEY: misc_feature
<222> LOCATION: (162)..(162)
<223> OTHER INFORMATION: n is a, c, g, or t
<220> FEATURE:
<221> NAME/KEY: misc_feature
<222> LOCATION: (289)..(289)
<223> OTHER INFORMATION: n is a, c, g, or t

<400> SEQUENCE: 133
ttgatattct cctaagtagt tagataagaa gaaaaaaaga aataaagata gtataaaaac    60
naataattat ttcaattatt gagatgtcct cccgagtcaa tagaggacat aaacaatgat   120
aagcttctca ataagagagc atatcaattt ttgagttact anagtgaagg cagcatggat   180
attatttatt taccacctaa cgatgcacac aaaccaagat tttgcacgtg tatcaatttt   240
ttgagttact attgggaaga tgacacggat attattaatt atctaacang tgtaaggaga   300
g                                                                  301

<210> SEQ ID NO 134
<211> LENGTH: 301
<212> TYPE: DNA
<213> ORGANISM: Glycine max

<400> SEQUENCE: 134
acaaagtcca catggttgaa ttcaacttcc cctgaaacgt tctccagaat ctcctcagcc    60
atgctatcag aatcaatctt tggaacccct tttatcactt ccattatgcg ttctcctgcg   120
gtacttgctt ctgagaagta cttcacgttc gacaaaccag cacctagtgc cctgtttcac   180
aaagaaaata gcaacaaaaa agtgtcactt aaacttagaa ttataagcat agttttaaat   240
tgtgaccaat tgtgagaaaa tgcgactaat gaggtcacaa ttgcgattga gatgcagtgg   300
t                                                                  301

<210> SEQ ID NO 135
<211> LENGTH: 301
<212> TYPE: DNA
<213> ORGANISM: Glycine max
<220> FEATURE:
<221> NAME/KEY: misc_feature
<222> LOCATION: (54)..(54)
<223> OTHER INFORMATION: n is a, c, g, or t

<400> SEQUENCE: 135
gcaacaagat aatatgttgg ttcatccatc cttagattat ttaggagaaa gttngcacat    60
aaattagcta ataaatatat accattctaa atttataata atagacatta aaagttttaa   120
taatattgct tctttaatta ttttcattaa ttactttat actttatcat cgatgttaca   180
tatctgaata ccaaatcatt actgaattga ttaaccccag ctcctcctat ctcccgtact   240
ttcataaatt tgggttaaag tggtgttcca agttatcaaa gctttatcat tagttgataa   300
a                                                                  301

<210> SEQ ID NO 136
<211> LENGTH: 301
<212> TYPE: DNA
<213> ORGANISM: Glycine max
<220> FEATURE:
<221> NAME/KEY: misc_feature
<222> LOCATION: (47)..(47)

<223> OTHER INFORMATION: n is a, c, g, or t

<400> SEQUENCE: 136

```
cctctctgaa taataaggtc aaatgtatgc gaggatcctc aaaaatngat ggactatttt    60
tttaccaggt aaggtacacc tgctttaatt tgttgttttt ctcaactgtg ggtggtggtg   120
atggaatgat agtcccatag tggggatttt gtaggtggga tatggatctt gatgctttgc   180
ctttaaaaaa gaatttgcga agcaactgtt tgtctggatt tgatatatat gctcgtgaat   240
aatggatctt gaatattata tatatgataa attcttaatt actggcgtta taaacacgtt   300
c                                                                   301
```

<210> SEQ ID NO 137
<211> LENGTH: 301
<212> TYPE: DNA
<213> ORGANISM: Glycine max

<400> SEQUENCE: 137

```
gcagcctcaa caatgtcttc ctcattggca tcttcttttc caaaaagtat attctcctta    60
atgctagttg caaaaagagt aggctcttgg ctaaccaaac ccatttgaga cctaaaccac   120
ttgagttgca acctattaat agccacacca tcaagacgta tctctccctc aattgggtca   180
taaaatcttt gcaaaagtga atcagagtg actttcctg acccacttcc tccaaccaat    240
gccactgtgt tccctgctgg aatctttagg cagaaatcat tcagaataac actgtctggc   300
c                                                                   301
```

<210> SEQ ID NO 138
<211> LENGTH: 301
<212> TYPE: DNA
<213> ORGANISM: Glycine max
<220> FEATURE:
<221> NAME/KEY: misc_feature
<222> LOCATION: (108)..(108)
<223> OTHER INFORMATION: n is a, c, g, or t

<400> SEQUENCE: 138

```
cttgaacata taattttgt attaaatatc ttatgtttat caggattttg gattaaaaaa    60
atctaatgag gacaatatat aacttttatg gggataaaaa aaaatttnta tacattaaca   120
aaaaaaaatc tggtggaaat aattacccca cagcatataa gatgcatttg cccgtactta   180
caccaaggac tttgaaagaa taaaattta tcgttatata cccataata aatacatgtg    240
tacttctaga actccatcca tattccatac catcaatttt cataggtttt atgtttggat   300
a                                                                   301
```

<210> SEQ ID NO 139
<211> LENGTH: 301
<212> TYPE: DNA
<213> ORGANISM: Glycine max

<400> SEQUENCE: 139

```
tgttattttt atttaaggaa aaatggtaaa tgatctttac cttctcatta ttaagtttta    60
gacactactt gttatgacg tgtctgagga ttcaagagca aaataaaaaa agtaaataaa   120
atgcgctgta acaagtcaca cactttacat tagaccagct ttacatatgc ctcctttgct   180
tagttctcat tatttggcag tttccttact ataccagaga gtgaaatgag tctggcacat   240
gagttcttac aatggtaaaa taacctactt tttaggtatt ttttaacaag ataaagtta   300
a                                                                   301
```

<210> SEQ ID NO 140
<211> LENGTH: 301
<212> TYPE: DNA
<213> ORGANISM: Glycine max
<220> FEATURE:
<221> NAME/KEY: misc_feature
<222> LOCATION: (7)..(7)
<223> OTHER INFORMATION: n is a, c, g, or t
<220> FEATURE:
<221> NAME/KEY: misc_feature
<222> LOCATION: (24)..(24)
<223> OTHER INFORMATION: n is a, c, g, or t

<400> SEQUENCE: 140
tgccgcngcc ggcttatatg gggngggttg gtcatcatgg acacgtgtaa atcattcttt    60
ggtctttgtg aaaagcgaag tcgtattggc tctcgaaaat agagaattgg tcgcctcaat   120
ataaaaacaa aatcgattat tctatgggcg gttccttaca ttttgatcca acggcttata   180
ttgtgcttca ttgcacggct ttgatctctt gatcttcccc caattatggg gtagatttca   240
gattggtgaa atcaaagggc tcatagcata ttcagtggaa gaactgatta ttttttttcct  300 c                                                                   301

<210> SEQ ID NO 141
<211> LENGTH: 301
<212> TYPE: DNA
<213> ORGANISM: Glycine max
<220> FEATURE:
<221> NAME/KEY: misc_feature
<222> LOCATION: (67)..(67)
<223> OTHER INFORMATION: n is a, c, g, or t
<220> FEATURE:
<221> NAME/KEY: misc_feature
<222> LOCATION: (137)..(137)
<223> OTHER INFORMATION: n is a, c, g, or t

<400> SEQUENCE: 141
ttcgtacaat attctctcct aaaaaggtta atctttttc aaaaggaaat caaacattat     60
acgaacntct ttcttaataa gaacttaatt atttaaacag caattcacta tttcttgaga   120
cattagtcct ttttgcnaca tctattggaa ggctattaca tgaggctgga aagtggaaac   180
ccaatggccc aaattgccac tgacaattaa ggggatttcc ctcatctgcg gatccacatg   240
ttataacttg atgggtttaa aggatcccag ctaagcccaa tacttattgg aaaaatattg   300
t                                                                   301

<210> SEQ ID NO 142
<211> LENGTH: 301
<212> TYPE: DNA
<213> ORGANISM: Glycine max
<220> FEATURE:
<221> NAME/KEY: misc_feature
<222> LOCATION: (89)..(89)
<223> OTHER INFORMATION: n is a, c, g, or t
<220> FEATURE:
<221> NAME/KEY: misc_feature
<222> LOCATION: (128)..(128)
<223> OTHER INFORMATION: n is a, c, g, or t

<400> SEQUENCE: 142
gaataaaatg attttaaaaa ataagggaac aaaaattata tttttaatct attattaaag    60
gatatctcac aaaaaccaag aagaagacna aagacacttt agcctaacat gaaaagtttt   120
attatccnaa cttaactctt ttaaaagccc aaataaacgg gcttctctaa gcccaattgt   180
atcagcagca gcaaacacag acaagttaaa aaaaccaaaa ctatacggtt gtcaaattag    240
tttctaaaat taaataagtt cctcaaataa gaatttataa atataaagta acttattaag    300
t                                                                    301

<210> SEQ ID NO 143
<211> LENGTH: 301
<212> TYPE: DNA
<213> ORGANISM: Glycine max
<220> FEATURE:
<221> NAME/KEY: misc_feature
<222> LOCATION: (33)..(33)
<223> OTHER INFORMATION: n is a, c, g, or t
<220> FEATURE:
<221> NAME/KEY: misc_feature
<222> LOCATION: (251)..(251)
<223> OTHER INFORMATION: n is a, c, g, or t
<220> FEATURE:
<221> NAME/KEY: misc_feature
<222> LOCATION: (264)..(264)
<223> OTHER INFORMATION: n is a, c, g, or t

<400> SEQUENCE: 143
tatttagtat aaactattca ctgaatatca ganttcagaa ggcgtgtgaa catgttttag    60
tataaactat tcattgaata tctgaattca gaaggcgtgt gaagatgttc acattcaagt   120
taaaattttg gtgaaaagca gagatatcca attagaaaag tctggctgct atagccttca   180
gttcacttca gggatcacag tattattttt ctccttgtaa taaaactggc tttttaagac   240
ggcaaattcg ncttgtttca tttnccgatt atcttttctc atagaagggg aaatcgttga   300
a                                                                    301

<210> SEQ ID NO 144
<211> LENGTH: 301
<212> TYPE: DNA
<213> ORGANISM: Glycine max
<220> FEATURE:
<221> NAME/KEY: misc_feature
<222> LOCATION: (10)..(10)
<223> OTHER INFORMATION: n is a, c, g, or t

<400> SEQUENCE: 144
aggaacattn tcaaaaaaaa aacaaaaaaa ctaagtaata actaacgttt atataaaaa    60 aattgatttg tgtttacaac tttaacaata caatcattgt cagttgtatt tttttttttt   120
atgtaaaaaa tttcagagga gaagacgatg gtccagtcta agatagaaaa accttcggct   180
caaaaaatgt ctcgctactt ctcagttgtt tcataaattt tttttatag aatatgtata   240 agagttatat aacgaatata ttttcttttt agaaattaaa attatctttt attgttttc   300 t                                                                    301

<210> SEQ ID NO 145
<211> LENGTH: 301
<212> TYPE: DNA
<213> ORGANISM: Glycine max
<220> FEATURE:
<221> NAME/KEY: misc_feature
<222> LOCATION: (274)..(274)
<223> OTHER INFORMATION: n is a, c, g, or t
<220> FEATURE:
<221> NAME/KEY: misc_feature
<222> LOCATION: (281)..(281)
<223> OTHER INFORMATION: n is a, c, g, or t

<400> SEQUENCE: 145
aagaaaaata aatctaaaag atataaaaaa tatcaaaaaa ggaagatggc tggcaaacac    60

```
aactttaaaa gggagtcaag tcaactataa aaatggagtc aagtcaagta gaaaacaatg      120
ccacataacc ctctagggtt tcatttactc ccttcctttc tttcacccCtt ctatcctacc      180 ggttttata ccccatccat tgtaaagcca tcaatgacca tcaatggtac tgctaattag      240
ggtctggcag acatgcaaat atgacttgca gatntaaaaa ngatagatta aagagaaaa      300 a                                                                    301
```

<210> SEQ ID NO 146
<211> LENGTH: 301
<212> TYPE: DNA
<213> ORGANISM: Glycine max
<220> FEATURE:
<221> NAME/KEY: misc_feature
<222> LOCATION: (12)..(12)
<223> OTHER INFORMATION: n is a, c, g, or t
<220> FEATURE:
<221> NAME/KEY: misc_feature
<222> LOCATION: (24)..(24)
<223> OTHER INFORMATION: n is a, c, g, or t
<220> FEATURE:
<221> NAME/KEY: misc_feature
<222> LOCATION: (281)..(281)
<223> OTHER INFORMATION: n is a, c, g, or t

<400> SEQUENCE: 146

```
acattggctt antttattat aacngggcca attttttaa agagggatcc aaaacaatat      60
atccattcgg acataatggt tttctaaatt actaaaatta atctatagtt atcactaaaa      120
gagttattta atattagaaa aaaataagtg tcaaatattt ttttctcttc ttttCttat      180 tttgataaaa ggcaagggct aagaccaagc acttcaaaac cttctagga aaagcaatac      240 cataggcacc cctggtggat gggacccata ctacggggaa natatgactg agtccatttc      300
a                                                                    301
```

<210> SEQ ID NO 147
<211> LENGTH: 301
<212> TYPE: DNA
<213> ORGANISM: Glycine max

<400> SEQUENCE: 147

```
agatgcttac tcaaggagac cgtgagttta tatatatata tatatatata tatatatata      60
tatatatata tatatatata ttatttatcg tttttgtgtt tttaggtaga gattggagtt      120
tgtttcggtt gatgctggtt gttggaaata aataccgtta aattggtggc ataattaata      180
tattctctct ctctttttttt tttcttctaa tatactactg ttcggttagg tgacgagcaa      240
gcgaacgatt cgattatttt actatttatt tattttCtctt ttttttttat atgcggctgg      300
g                                                                    301
```

<210> SEQ ID NO 148
<211> LENGTH: 301
<212> TYPE: DNA
<213> ORGANISM: Glycine max
<220> FEATURE:
<221> NAME/KEY: misc_feature
<222> LOCATION: (123)..(123)
<223> OTHER INFORMATION: n is a, c, g, or t

<400> SEQUENCE: 148

```
tgtttcttct cttcccatat ttttctatt ctaattgctt gtatttaagc ccatcacttt      60
tgaccatcaa gccctaaata actattatcc actattccaa ggagaataaa cgaagaatgc     120
```

```
tcngggtatt aaagtattga ctaaaacatt acttcactit ttgatagctg ccgtagcatt    180
gttgtgtctc tatggttcac ttttgattcc gccgtttcat acagtaacag atggcaaata    240
tcaatcattt taaattggcc aagcgataga aaaatgccaa tgccgcgctg ctgtatgaaa    300
c                                                                    301
```

```
<210> SEQ ID NO 149
<211> LENGTH: 301
<212> TYPE: DNA
<213> ORGANISM: Glycine max
<220> FEATURE:
<221> NAME/KEY: misc_feature
<222> LOCATION: (276)..(276)
<223> OTHER INFORMATION: n is a, c, g, or t
<220> FEATURE:
<221> NAME/KEY: misc_feature
<222> LOCATION: (300)..(300)
<223> OTHER INFORMATION: n is a, c, g, or t

<400> SEQUENCE: 149
```

```
atattatttt ttggtgttat tcttgtcaat tttttgtatt aagaaaatta tttgactgat     60
caaaattgac acactaaaat taatgtttag agtatcatgt ttagagattc atttgtttat    120
aattatagct gtaaaattta actgccagag agagattgct gaactttgct gccttccttc    180
atccacatga ctactatttc atcgtcggta taaatgacct tgtgcatgtt tcatggacat    240
ctaaactggg ctggatagtt atgggccaat acctgnccca tttccttcca agtgaacaan    300
t                                                                    301
```

```
<210> SEQ ID NO 150
<211> LENGTH: 301
<212> TYPE: DNA
<213> ORGANISM: Glycine max
<220> FEATURE:
<221> NAME/KEY: misc_feature
<222> LOCATION: (16)..(16)
<223> OTHER INFORMATION: n is a, c, g, or t
<220> FEATURE:
<221> NAME/KEY: misc_feature
<222> LOCATION: (40)..(40)
<223> OTHER INFORMATION: n is a, c, g, or t
<220> FEATURE:
<221> NAME/KEY: misc_feature
<222> LOCATION: (43)..(43)
<223> OTHER INFORMATION: n is a, c, g, or t
<220> FEATURE:
<221> NAME/KEY: misc_feature
<222> LOCATION: (74)..(74)
<223> OTHER INFORMATION: n is a, c, g, or t
<220> FEATURE:
<221> NAME/KEY: misc_feature
<222> LOCATION: (81)..(81)
<223> OTHER INFORMATION: n is a, c, g, or t

<400> SEQUENCE: 150
```

```
aagtagtcat actttnaatt aatcttcttg cagccaactn ccnccgccat tctcaaaaca     60
aaaaacattg cccnaagttt ngtttgaaga atagaacaaa accttagtct cctagaaaaa    120
gcttaaacaa tgttatattc atcatcccaa ataaccccat cacacgaaat tgcgtttatg    180
gtctaacaga caacatcatc acatttaaat cccatcacga agttgtgtat atcggtaaaa    240
aaatctcatc aattctatat ttttcaggga attttatagg agatttcaca agtaaactca    300
a                                                                    301
```

```
<210> SEQ ID NO 151
<211> LENGTH: 301
```

```
<212> TYPE: DNA
<213> ORGANISM: Glycine max
<220> FEATURE:
<221> NAME/KEY: misc_feature
<222> LOCATION: (148)..(148)
<223> OTHER INFORMATION: n is a, c, g, or t
<220> FEATURE:
<221> NAME/KEY: misc_feature
<222> LOCATION: (277)..(277)
<223> OTHER INFORMATION: n is a, c, g, or t

<400> SEQUENCE: 151
tcctgtcttt cttagtctct ctacctcttt tcaaaggact aaaaacagtg atctactctt      60
ttcattagtt tttccagtga ccattttaca tgtgtccaaa ccaccttaaa atatgtcatt     120
ttttcctcat tgatgcctca ccatctantc atatatactc atactcatta catatcttgt     180
cttttcttgc ttggccacac atccatctta agttttaagg aacataatat atgtaaaaaa     240
ggtgaaaaga acatgttatt gaatagaatt ctgtagntct ttctatcaat ataattcctg     300
t                                                                    301

<210> SEQ ID NO 152
<211> LENGTH: 301
<212> TYPE: DNA
<213> ORGANISM: Glycine max
<220> FEATURE:
<221> NAME/KEY: misc_feature
<222> LOCATION: (6)..(6)
<223> OTHER INFORMATION: n is a, c, g, or t
<220> FEATURE:
<221> NAME/KEY: misc_feature
<222> LOCATION: (54)..(54)
<223> OTHER INFORMATION: n is a, c, g, or t
<220> FEATURE:
<221> NAME/KEY: misc_feature
<222> LOCATION: (82)..(82)
<223> OTHER INFORMATION: n is a, c, g, or t

<400> SEQUENCE: 152
gtcacnagag acttattaca aaatatgatt ttaaatgaga gatttacgta aatnatttat      60
gtctataaac aatttgtctt tnttatttta catatatatg aactgctcaa agcttcttta     120
ccatgatgct tcttcaggca ggttctgcat atgcgctttg aattttctgc ttggacccgt     180
aaagcttttg ggagggcttt tgggtaagta gtgctctgtc tctttgacag atcttggcac     240
tatcattata aatctcttcg gtacgtaaaa caaaatgata tgcatgtaat ttattgagtt     300
g                                                                    301

<210> SEQ ID NO 153
<211> LENGTH: 301
<212> TYPE: DNA
<213> ORGANISM: Glycine max
<220> FEATURE:
<221> NAME/KEY: misc_feature
<222> LOCATION: (101)..(101)
<223> OTHER INFORMATION: n is a, c, g, or t
<220> FEATURE:
<221> NAME/KEY: misc_feature
<222> LOCATION: (286)..(286)
<223> OTHER INFORMATION: n is a, c, g, or t

<400> SEQUENCE: 153
taaacgagaa actaatgtaa aaggcacttc atttttttgcg gcttttttttc cacatacatg     60 taaacatttt ttgttgggcc agactaggtt ggcctgcatg ntacatggat tactaaatta     120
gtcattcctg tctatttatt catgctaatc ccccttttac tttaattaat ttatactgac     180
```

```
ttaaatctct atcgcatgct attaggaact cctccttatg gtagttttgt tttgcttggg    240
tgcaaacaac cccccaatta ataaaaaaaa ataaaaaaca ttgccncaca atcggcgagt    300
t                                                                    301
```

```
<210> SEQ ID NO 154
<211> LENGTH: 955
<212> TYPE: DNA
<213> ORGANISM: Glycine max
<220> FEATURE:
<221> NAME/KEY: misc_feature
<222> LOCATION: (205)..(205)
<223> OTHER INFORMATION: n is a, c, g, or t
<220> FEATURE:
<221> NAME/KEY: misc_feature
<222> LOCATION: (606)..(606)
<223> OTHER INFORMATION: n is a, c, g, or t
<220> FEATURE:
<221> NAME/KEY: misc_feature
<222> LOCATION: (942)..(942)
<223> OTHER INFORMATION: n is a, c, g, or t

<400> SEQUENCE: 154
tgataaacca atatcatctt acaatgagag gatggccaaa gttttgttag ctgaatatat    60
taactatatc ctgatttctg tctcaggttt tataattcgt gaatcaagtt ccaaaactaa   120
agttaatttc aaagacaact accggaactg ctaaacttgg gattgcaaag atgatgctgg   180
tctgtcaagt tgtttgagtt atganagttt tgagctaaga ctgcaagtgg tgctcttggc   240
tgctgattta ttggagttcc atttcgtaaa tgtgatcggt cctcaaattt gatcttttct   300
gcatcatcag caatatcggc cctcctatat tccaatagga taatatgtta gcacttctct   360
ttgtagaatt tgtgtatttt gatacataca gtatacagta cctcaaattc ttaataggta   420
ctccagattc tgatgttgta tccatattat tacaatgttg gagcatcatc ctcttgttat   480
ttgaattgat gtatgaagtg ctgttctctt ttgctaaagc tgcatatttc tgtttcttcc   540
tgcagatgaa taagaaattg cagcaattga gggcaccaaa aaagaagcag cttcaggcta   600
caaaantgag cgtggaaggt cgtggtatga tcaaatattt ataaatgtga ccacgttgat   660
actggatggg tttgtttgtc ctgctgcaag cttttcatat aatgtgctgc ctgcattgat   720
gtggattctt ctaaaggtgg gctattcgtt cagtgatcta catggaaatt tgatggagag   780
ggatgttatg aaaataccat ccgtatgctg catttgtgta ttcatctagt gcagtaggaa   840
atccaaaata cattggacgg ttatgcattc gtatatatag tcaagcttgt catcagttta   900
atgaaaatgt ggattttgca ttcgtccttg gtacaagtaa tntttgtagt gcagc         955
```

```
<210> SEQ ID NO 155
<211> LENGTH: 401
<212> TYPE: DNA
<213> ORGANISM: Glycine max

<400> SEQUENCE: 155
gccctgtttg gaaggccaga tattcgtgtc tccgacgatg gttcaattga acatccaat     60 gatgaattgc tttcactcac tttctcgggc ctgactatgc tagttttgga ggcaattgct   120
tttggatcat tcctatggga caaagaaaac tatgttgaat ccaagtaccc ttttcttaat   180
gagtagacta gatgacagta cacagattct ttcctttcac tgcatggaac ttggtaactt   240
agtaatatgt taggcggcgt ttgggtggtc ttgctatctt aactggtgtg ctttcaaact   300
attatagaat ctgaaacaaa tcatgggcgt ggagttatat aggaaaatgt acatatttag   360
catgtagaca tgataataat ctatgcaagc ctggactttg a                        401
```

<210> SEQ ID NO 156
<211> LENGTH: 301
<212> TYPE: DNA
<213> ORGANISM: Glycine max
<220> FEATURE:
<221> NAME/KEY: misc_feature
<222> LOCATION: (198)..(198)
<223> OTHER INFORMATION: n is a, c, g, or t

<400> SEQUENCE: 156

| | | | | | |
|---|---|---|---|---|---|
| agatttgttt | gttcacaatt | tcccatacat | atagaaagaa | ttaaacaatt | ttttattata | 60 |
| tatttattat | gtagtcgaat | tttttgactc | aacctaattc | taattgaatg | tactaaatat | 120 |
| tgagttacgt | gcgttgaacg | cacacaaccc | acttacaccc | ataaaaaaac | caatggaaag | 180 |
| taacatatta | agattatnta | tatggaattg | aagctgcttc | tatacctaca | ctgctgcact | 240 |
| tgtgtttgcc | tttaaactca | tgtttatatc | catgtataaa | acaatacatg | tacagcatca | 300 |
| t | | | | | | 301 |

<210> SEQ ID NO 157
<211> LENGTH: 301
<212> TYPE: DNA
<213> ORGANISM: Glycine max

<400> SEQUENCE: 157

| | | | | | |
|---|---|---|---|---|---|
| caaaagtggt | taagatggct | gccgggaggc | ttgaacagat | gccaccggag | gcgccgaaaa | 60 |
| acaatatgca | agttgtgttc | acttcgactt | gcccacagcc | atcattcacg | ctgccacgga | 120 |
| caaggtcatt | tccatttttcc | aacttctctt | aatattttt | ttcttcacta | aaagtttttg | 180 |
| catggttcct | aattatttag | aagttctgaa | ccacacataa | ccatacatct | cgacccatct | 240 |
| ctacatgaca | catattaatc | aaggtgtcat | taattgtttt | ttcttaaaat | ttaaaaactt | 300 |
| a | | | | | | 301 |

<210> SEQ ID NO 158
<211> LENGTH: 301
<212> TYPE: DNA
<213> ORGANISM: Glycine max
<220> FEATURE:
<221> NAME/KEY: misc_feature
<222> LOCATION: (45)..(45)
<223> OTHER INFORMATION: n is a, c, g, or t
<220> FEATURE:
<221> NAME/KEY: misc_feature
<222> LOCATION: (92)..(92)
<223> OTHER INFORMATION: n is a, c, g, or t
<220> FEATURE:
<221> NAME/KEY: misc_feature
<222> LOCATION: (135)..(135)
<223> OTHER INFORMATION: n is a, c, g, or t
<220> FEATURE:
<221> NAME/KEY: misc_feature
<222> LOCATION: (223)..(223)
<223> OTHER INFORMATION: n is a, c, g, or t

<400> SEQUENCE: 158

| | | | | | |
|---|---|---|---|---|---|
| tcccaatttc | tgcatctttc | aagtgcttca | atgctatgca | caganattaa | cagccttctc | 60 |
| agaagcttaa | atagttttct | cctaattact | cncagacaag | tgataaaata | gcgtaccgtg | 120 |
| tcacgcgata | ctatngattt | ttcgggacga | aaactgtgaa | gggaagctgc | aattttgcga | 180 |
| accctaacac | aatcacgacg | aacgaagaag | accaccgatg | agnaagcaaa | ttgaaacgac | 240 |
| agcgttttat | atcaatgtgc | acgtttcgat | tgcattaaaa | ttaataatt | tgttttttt | 300 | c                                                                                  301

<210> SEQ ID NO 159
<211> LENGTH: 301
<212> TYPE: DNA
<213> ORGANISM: Glycine max
<220> FEATURE:
<221> NAME/KEY: misc_feature
<222> LOCATION: (58)..(58)
<223> OTHER INFORMATION: n is a, c, g, or t
<220> FEATURE:
<221> NAME/KEY: misc_feature
<222> LOCATION: (96)..(96)
<223> OTHER INFORMATION: n is a, c, g, or t
<220> FEATURE:
<221> NAME/KEY: misc_feature
<222> LOCATION: (297)..(297)
<223> OTHER INFORMATION: n is a, c, g, or t

<400> SEQUENCE: 159
ttaaagcata attttataat gtgtttggaa gagaagatga aaataatatt gaagaaanat      60
tttgtatttt tttagtggga caaagacctt tttacnctat tttaatttaa aaatttatct     120
tctattttca ttgtgaaaac caaacacacc agagaggaat agatcgtacc gatgggttca     180
caaagcattt cttcattcca actgttaacg ctgggttgga ttaaaatttg aaaagtactt     240
ttacaaagtt cattacataa taagaaattc caatgcacca aatgaagaaa gaaaaanttg     300
t                                                                    301

<210> SEQ ID NO 160
<211> LENGTH: 1274
<212> TYPE: DNA
<213> ORGANISM: Glycine max
<220> FEATURE:
<221> NAME/KEY: misc_feature
<222> LOCATION: (1164)..(1164)
<223> OTHER INFORMATION: n is a, c, g, or t

<400> SEQUENCE: 160
cttctcccat ctatgccaag aagtcctgga agagcagata atccaattag ccctggatca      60
cgttggaaaa aaggaaagct gcttggcaga ggcacatttg acatgtcta tgttggcttt      120
aataagtatg tgcttgtgac caaaagttct tgattatatt atgaagaaat cttttttata     180
cttttaaatc cattagttta tacatcttat aaattgtttg gttaaaatgt tgtcatgtgt     240
agggaaagtg gtgaaatgtg tgctatgaaa gaggtaactc tgttttcaga tgatgccaaa     300
tctaaagaaa gtgctaagca attaatgcag gtaaattgat ttccttttttg accttttgaaa    360
ttttttttgtg ggactgaata gatttccttt ttgacctttg tgcaatatgt cagtatctat     420
ttctgtttca aatttggtgt agctttgaaa atctaactcc cagattctgg caggaaatta     480
ccttgttgag ccggttacga catccaaata ttgtgcagta ttatggttcc gaaacagtaa     540
gctctccatt tcctgtttct ttctcattct cctgttttta ttagctgttt gtgagtgatc     600
atggatttat tttgggattt atctgcagca ggtctttgat gatcatcttc agcttatcac     660
tacacatgct ttcaagtccc tcaggaatcg gtcgccttat ttcggaaaaa agcttccggg     720
ccaagtctct gagaagctcc tcagttttac aagattgaga acggtaacc caaacacagg      780
cttttgaagtg ttttcttact tctggatcat cgaatacttt cttaccaaa gtagttttttc    840
ccatccctcc cattccagtg acagaaatca cttttcgtcc ggtacaacca ttaatcaacc     900
acccgatcag ctgctttta ggcctgtcta ttccaactag atcagtgttg tccaggagaa      960
gggcgtctcc ccgttgatca tgccacgcgt taactgtttc aagatatgtt tattgtacta    1020

```
gctcacaagt gagaattgtg tatatagcaa accgaataca ctttccttgt tagaatgaaa    1080
attgttcact accacttgct cactttctac atgcacttca ttaacactat cagtctatta    1140
taaaaatgca agttatgtaa gtgnaattta aatgcatcaa tgatgtaaaa gaagaggtaa    1200
acataatcac caattggagg ttcaaattgt tattacttga agctttcaaa ttctagactt    1260
gtatagtgaa acat                                                      1274

<210> SEQ ID NO 161
<211> LENGTH: 301
<212> TYPE: DNA
<213> ORGANISM: Glycine max
<220> FEATURE:
<221> NAME/KEY: misc_feature
<222> LOCATION: (214)..(214)
<223> OTHER INFORMATION: n is a, c, g, or t
<220> FEATURE:
<221> NAME/KEY: misc_feature
<222> LOCATION: (237)..(237)
<223> OTHER INFORMATION: n is a, c, g, or t
<220> FEATURE:
<221> NAME/KEY: misc_feature
<222> LOCATION: (242)..(242)
<223> OTHER INFORMATION: n is a, c, g, or t

<400> SEQUENCE: 161
ggcacacatg ggcttcagag aagctagagg agacacaaaa cgcaataaaa agagggttct     60
tggtagagga agagaattgt cgttgagttt ggattatagt agtttctagt gaaagggtaa    120
gacgttggtt agctcataag atttagcgct tgagttctcc caatgtgtcg ttgtcgcaaa    180
cacaaatggt gtactcgttg ttgaagttgt agcngtagta gccatgcctg ctcctcngtc    240
anacactact cactcaacca ctactatttc tttcttcctt cttttacaac aagagggcaa    300
c                                                                    301

<210> SEQ ID NO 162
<211> LENGTH: 301
<212> TYPE: DNA
<213> ORGANISM: Glycine max
<220> FEATURE:
<221> NAME/KEY: misc_feature
<222> LOCATION: (27)..(28)
<223> OTHER INFORMATION: n is a, c, g, or t
<220> FEATURE:
<221> NAME/KEY: misc_feature
<222> LOCATION: (62)..(62)
<223> OTHER INFORMATION: n is a, c, g, or t
<220> FEATURE:
<221> NAME/KEY: misc_feature
<222> LOCATION: (148)..(148)
<223> OTHER INFORMATION: n is a, c, g, or t
<220> FEATURE:
<221> NAME/KEY: misc_feature
<222> LOCATION: (194)..(194)
<223> OTHER INFORMATION: n is a, c, g, or t
<220> FEATURE:
<221> NAME/KEY: misc_feature
<222> LOCATION: (269)..(269)
<223> OTHER INFORMATION: n is a, c, g, or t
<220> FEATURE:
<221> NAME/KEY: misc_feature
<222> LOCATION: (273)..(273)
<223> OTHER INFORMATION: n is a, c, g, or t

<400> SEQUENCE: 162
tataattcct taaaatctga ttttttnnaa atgggagtcc ctacgtggat gtactaacac     60
tnaagttata aaactagtaa ttgaaaagaa gtgagatttg aggatgagac cgtgaagggg    120
```

```
tgatgcgaag aagaagagga ggggcgcnag gaggcagaga aagaggacaa cgagaagagg    180
gaaatgggat cccntggttc tgttgttgtt ggatggcatt gcagatctta atccatgtct    240
tgtctctttg tgttagcttc tatagttcnt ttntctctca cacacaggca ttcactccct    300
t                                                                   301
```

```
<210> SEQ ID NO 163
<211> LENGTH: 301
<212> TYPE: DNA
<213> ORGANISM: Glycine max
<220> FEATURE:
<221> NAME/KEY: misc_feature
<222> LOCATION: (31)..(31)
<223> OTHER INFORMATION: n is a, c, g, or t
<220> FEATURE:
<221> NAME/KEY: misc_feature
<222> LOCATION: (42)..(42)
<223> OTHER INFORMATION: n is a, c, g, or t
<220> FEATURE:
<221> NAME/KEY: misc_feature
<222> LOCATION: (207)..(207)
<223> OTHER INFORMATION: n is a, c, g, or t
<220> FEATURE:
<221> NAME/KEY: misc_feature
<222> LOCATION: (227)..(227)
<223> OTHER INFORMATION: n is a, c, g, or t

<400> SEQUENCE: 163
```

```
agtttgtaaa ccttttgctg aagaagaatc natttaacga gnatacataa tatattccaa    60
ctatgatgga acatcacatt cttataaata gttccagaat aattaaatta cctaacagta   120
acagtttcat aaacttattg aacacattta aacttattct atatatatgg ctatttgacc   180
ggggtcaggt tataggcagg tgctttngta cctaattatg tttgggntat gatatgaaaa   240
taatgtaaaa ggtgaaagat atacaaagac agtacagaga aagaactaat atattaaaag   300
a                                                                   301
```

```
<210> SEQ ID NO 164
<211> LENGTH: 301
<212> TYPE: DNA
<213> ORGANISM: Glycine max
<220> FEATURE:
<221> NAME/KEY: misc_feature
<222> LOCATION: (15)..(15)
<223> OTHER INFORMATION: n is a, c, g, or t
<220> FEATURE:
<221> NAME/KEY: misc_feature
<222> LOCATION: (81)..(81)
<223> OTHER INFORMATION: n is a, c, g, or t
<220> FEATURE:
<221> NAME/KEY: misc_feature
<222> LOCATION: (118)..(118)
<223> OTHER INFORMATION: n is a, c, g, or t
<220> FEATURE:
<221> NAME/KEY: misc_feature
<222> LOCATION: (292)..(292)
<223> OTHER INFORMATION: n is a, c, g, or t

<400> SEQUENCE: 164
```

```
taaacatgat agganattat tataaattct gatatttgta tttgatttct actaattaaa    60
aaaaaaatgt ttttggtaat ntcttgagag agaaaaaaaa tgtttccatt ctgtttcngc   120
gaacgaaact ccacatgtgg agtagttcct ccccgcggga aattgcggag tgaaggaaat   180
tctcttcttt ttgtcttttt tacactgaac gaacgtaaca ttcattccat tattccaatt   240
tctgaacaca atgttattgt taatgttccg tagttgccac gttcctatgt cnccccacac   300
a                                                                   301
```

<210> SEQ ID NO 165
<211> LENGTH: 301
<212> TYPE: DNA
<213> ORGANISM: Glycine max

<400> SEQUENCE: 165 aattttcgg aattttaaat ttctccatcc aaacacactc ttaaaattta acggtagct       60 tgggaattcc aatatcgcaa attgagaaag aaccaacttg tgttattgga gccaacgtac    120
attatgttca acatatcttg tttacaaaca caccctaaca gggtgtcaaa tagaagtccc    180
tgaatctcct agttatgcca aaagtaaata ttgaactttt taaatatttc catcatgttt    240
gtgatcatgt atcttcttaa gagaacatgc aacagaagga tagaaagaaa taaacaaatt    300
t                                                                    301

<210> SEQ ID NO 166
<211> LENGTH: 301
<212> TYPE: DNA
<213> ORGANISM: Glycine max
<220> FEATURE:
<221> NAME/KEY: misc_feature
<222> LOCATION: (227)..(227)
<223> OTHER INFORMATION: n is a, c, g, or t
<220> FEATURE:
<221> NAME/KEY: misc_feature
<222> LOCATION: (261)..(261)
<223> OTHER INFORMATION: n is a, c, g, or t

<400> SEQUENCE: 166
ttctatataa tgttctgagt gactatagtt caaatttgtc ttcctctctg tctttacttt     60
tcttgcttta tcctaaccat catcaaagaa aataccattt agaagaataa tctggaattt    120
ctcgttattt gttaatttgc agaagtatag acttggacag caagctcgga aacaaaatga    180
ggatatgcac aaagaaaata atagtgagtc cattgcaagt tttaacnaac actgggcatc    240
ccatgcattt cttttactta ntatctagaa tagtttgtcc aacttctccc acagagattt    300
t                                                                    301

<210> SEQ ID NO 167
<211> LENGTH: 301
<212> TYPE: DNA
<213> ORGANISM: Glycine max
<220> FEATURE:
<221> NAME/KEY: misc_feature
<222> LOCATION: (196)..(196)
<223> OTHER INFORMATION: n is a, c, g, or t

<400> SEQUENCE: 167
acagttggag ttggcatatc tgaagattca ttgctacaga ctccatgcat gttctccacc     60
tagtaatcat gatcagcccc cactcgtgtt gcctcccctc attctttctg ttcgtcatct    120
tctaaggcag aattgggaag ttcatatgca ccatactctt tcgtgaagaa aattcttgtc    180 ctgtttttt tttttngcaa agtatgatgg agctgcgcac tgtgatttcc tccatgttca    240
tgcaagtccc ccccaggaac tagctttacc ttgcaagctg atgctatggg cattctgttt    300
c                                                                    301

<210> SEQ ID NO 168
<211> LENGTH: 301
<212> TYPE: DNA
<213> ORGANISM: Glycine max

<400> SEQUENCE: 168

```
tttctacatc tactagtctc taccacatca ctttaatgtt attttttaatt agagttaatt    60
atttattatg tgttgttgat caaaaaagga ggtgggtccc acgtgatttt tgttttttg    120
gagatgacgg atatggccct cggtgggaga agcgtgcaca tttgtttgta ttggggttat   180
ggtcattgtc cagttgtgct aggccactta catggggtag ggtgtagtgg gattaatttg   240
tgcgtctcac tgtggagtgt ggacagctaa gcgtgacatt attgaaattt caattttcaa   300
a                                                                   301
```

<210> SEQ ID NO 169
<211> LENGTH: 301
<212> TYPE: DNA
<213> ORGANISM: Glycine max

<400> SEQUENCE: 169

```
ttggcatata tgaaccatta caaattaact tttttttaac ctatgatgcc ccattgcata    60
tatatgatgc tttgtgtaag ctatttagaa ggataactta gatcctgttg ttcccaagca   120
catccacaca ataaatacaa ggcggctttc tgaagtcaaa tagtactaaa aagcagtttc   180
tatttagagt agtaatacat tagttatgct gcttcctagg atgagatttt tcacagaagg   240
taggtcccaa ttcatttaat atgggataat ggtttctata agctcttgaa ggggcgcaag   300
c                                                                   301
```

<210> SEQ ID NO 170
<211> LENGTH: 544
<212> TYPE: DNA
<213> ORGANISM: Glycine max

<400> SEQUENCE: 170

```
attgtgagcc tcaaagaaga ggcgcactta aacacttgct tcaagcattt tatactcttc    60
acctgtgtaa gtctcatatt ttcctttcat ttatttattt ttgtgtacgt tggcttgttt   120
ctattcaaaa ctctctttaa aaatactaat aatttaaatc agctaattgt ctaacattgc   180
agattttgtt tgaaactttt gttatgcagg agttcgggct gattgacaaa aaggagcttg   240
cgccccttca agagcttata gaaaccatta tcccatatta aatgaattgg gacctacctt   300
ctgtgaaaaa tctcatccta ggaagcagca taactaatgt attactactc taaatagaaa   360
ctgcttttta gtactatttg acttcagaaa gccgccttgt atttattgtg tggatgtgct   420
tgggaacaac aggatctaag ttatccttct aaatagctta cacaaagcat catatatatg   480
caatggggca tcataggtta aaaaaaagtt aatttgtaat ggttcatata tgccaaatgt   540
tatc                                                                544
```

<210> SEQ ID NO 171
<211> LENGTH: 682
<212> TYPE: DNA
<213> ORGANISM: Glycine max
<220> FEATURE:
<221> NAME/KEY: misc_feature
<222> LOCATION: (50)..(50)
<223> OTHER INFORMATION: n is a, c, g, or t
<220> FEATURE:
<221> NAME/KEY: misc_feature
<222> LOCATION: (397)..(397)
<223> OTHER INFORMATION: n is a, c, g, or t

<400> SEQUENCE: 171

```
ttaatgtaat caaagaaagg tagtttcttg ctgataaaaa aaaaggaaan ctagtttcat    60
```

```
attggtgggc catgtgtcca aatagtgatg gatagttgat agttgtctgg tgacatggga      120
taggttttta aaggaaatat tgaatatggc tattttctct aattgtctgg tgatatgatt      180
ttcaatattg ggtcatcagt gaactaatgg aatctttaat tttccctcaa tgtcttctcc      240
atcttgttct ttgtgttctt gttttctctc cctattactt tgagatacat tcttatgta       300 gccttgttat agttgtttac ttttttgggt gtgtgaatgg aagctggtat tgatatttga      360
taccatgtta atgactacga catgcacgca ctgaagntca cattttttat tttgtagagt      420
tataaaaagt gtagtgaaag tgagagggga gataaataat tggagttata ttttgatgat      480
tgaagtgatt ttagtcatta tatataagta aatggtgggg tttgaggtaa tttggatatt      540
aacttatttt tatgacaatg gaaaagggga gcatataaat ttcattacgc agagtgtgta      600
agaaaagttt tcttctggac attacctaaa gtattttcct caacagattc atgggcagag      660
aggggttact ttttcaattc aa                                               682

<210> SEQ ID NO 172
<211> LENGTH: 301
<212> TYPE: DNA
<213> ORGANISM: Glycine max
<220> FEATURE:
<221> NAME/KEY: misc_feature
<222> LOCATION: (210)..(210)
<223> OTHER INFORMATION: n is a, c, g, or t
<220> FEATURE:
<221> NAME/KEY: misc_feature
<222> LOCATION: (280)..(281)
<223> OTHER INFORMATION: n is a, c, g, or t

<400> SEQUENCE: 172
ggtaagattc tgaaacaatg gtggcagtaa gtgaaaggtg aagaagaggg tgcaaagaga       60
ggaggagaag ctgagtattt ggcttgcttt tagaggctgt gatgcagcaa gacctcttcc      120
tttgccaagt atttgttcca tcctcaagag agaccttgaa tcagccatgg aaacaaacaa      180
aaccttcact gcctaactat agaatagcan tatattgttt tcttttgtac agtttaatta      240
tgagagtctt aaatatataa ttatattaaa tatttttttn naaaaattgt tattcatata      300
g                                                                     301

<210> SEQ ID NO 173
<211> LENGTH: 338
<212> TYPE: DNA
<213> ORGANISM: Glycine max

<400> SEQUENCE: 173
gaagtctaag ttcccttttc atagatcaga aattcatcat caggttcatt acttttcaca       60
cattgcaccc ctaggtgcaa cctttaagga acccaagggg tttggaccta ccccaaggaa      120
aatgaagaag agcaagaaga tgaaaaagga ctatggagaa gatgaagatg aagaagaaga      180
agaagaagat gaagatgaag aagagagcc agacagggga gttattcctg aagtagtgac      240
caacagaatg atgaacagga tggcagtgtc tgtagggatt ccactgggtg ttgggctttt      300 gttttttccca ttattttact atctcaaggt tgggttga                             338

<210> SEQ ID NO 174
<211> LENGTH: 301
<212> TYPE: DNA
<213> ORGANISM: Glycine max

<400> SEQUENCE: 174
```

```
tttttttttt cttcttcttc ttatttatgt ctctttgcct ccctcattaa ccgctttcat      60 ttcatcctc cgacgaacat ttcttcacgt tcaccctctt tgtttaatgt gacaataacc     120
ttgttttcgt ttctattaat tattctttcc aatgagtaat aatagcacta gatgggtttg    180
tttctctctt atctcggtga tcggggattg attgtgattt acacaaaagc taaagagaga    240
atcagaagga gaagacgggt gcgtgaggga cgtgtcagaa aacttcggct tcgacacgct    300
t                                                                   301
```

```
<210> SEQ ID NO 175
<211> LENGTH: 23
<212> TYPE: DNA
<213> ORGANISM: Glycine max

<400> SEQUENCE: 175
ccgtatgctg catttgtgta ttc                                            23

<210> SEQ ID NO 176
<211> LENGTH: 24
<212> TYPE: DNA
<213> ORGANISM: Glycine max

<400> SEQUENCE: 176
tgcataaccg tccaatgtat tttg                                           24

<210> SEQ ID NO 177
<211> LENGTH: 15
<212> TYPE: DNA
<213> ORGANISM: Glycine max

<400> SEQUENCE: 177
tagtgcagca ggaaa                                                     15

<210> SEQ ID NO 178
<211> LENGTH: 14
<212> TYPE: DNA
<213> ORGANISM: Glycine max

<400> SEQUENCE: 178
tgcagtagga aatc                                                      14

<210> SEQ ID NO 179
<211> LENGTH: 21
<212> TYPE: DNA
<213> ORGANISM: Glycine max

<400> SEQUENCE: 179
cccgatcagc tgcttttag g                                               21

<210> SEQ ID NO 180
<211> LENGTH: 19
<212> TYPE: DNA
<213> ORGANISM: Glycine max

<400> SEQUENCE: 180
cgcccttctc ctggacaac                                                 19

<210> SEQ ID NO 181
<211> LENGTH: 18
<212> TYPE: DNA
<213> ORGANISM: Glycine max

<400> SEQUENCE: 181
```

```
ctgatctagt tggaatag                                                    18

<210> SEQ ID NO 182
<211> LENGTH: 19
<212> TYPE: DNA
<213> ORGANISM: Glycine max

<400> SEQUENCE: 182
actgatctag taggaatag                                                   19

<210> SEQ ID NO 183
<211> LENGTH: 28
<212> TYPE: DNA
<213> ORGANISM: Glycine max

<400> SEQUENCE: 183
gaatggaagc tggtattgat atttgata                                         28

<210> SEQ ID NO 184
<211> LENGTH: 26
<212> TYPE: DNA
<213> ORGANISM: Glycine max

<400> SEQUENCE: 184
ttatctcccc tctcactttc actaca                                           26

<210> SEQ ID NO 185
<211> LENGTH: 16
<212> TYPE: DNA
<213> ORGANISM: Glycine max

<400> SEQUENCE: 185
tgactacgac atgcac                                                      16

<210> SEQ ID NO 186
<211> LENGTH: 17
<212> TYPE: DNA
<213> ORGANISM: Glycine max

<400> SEQUENCE: 186
tgactatgac atgcacg                                                     17
```

MOLECULAR MARKERS ASSOCIATED WITH SOYBEAN TOLERANCE TO LOW IRON GROWTH CONDITIONS

CROSS-REFERENCE TO RELATED APPLICATIONS

This application is a 35 U.S.C. § 371 National Phase application of International Patent Application No. PCT/US2012/052871, filed Aug. 29, 2012 and incorporated herein by reference in its entirety which claims the benefit of U.S. Provisional Patent Application No. 61/529,838, filed Aug. 31, 2011, which is incorporated herein by reference in its entirety.

INCORPORATION OF SEQUENCE LISTING

A sequence listing is contained in the file named "46_21_57867.txt" which is 96,920 bytes (measured in MS-Windows) and was created on Aug. 29, 2012, and comprising 186 nucleotide sequences and is electronically filed herewith and is incorporated herein by reference.

INCORPORATION OF APPENDIX

A listing of various soybean markers is provided herewith in an Appendix to the Specification as Tables 12, 14, 17, 20, 23, 26, and 29.

BACKGROUND OF INVENTION

Soybean, *Glycine max* (L.) Merril, is a major economic crop worldwide and is a primary source of vegetable oil and protein (Sinclair and Backman, *Compendium of Soybean Diseases*, 3$^{rd}$ Ed. APS Press, St. Paul, Minn., p. 106. (1989). Growing demand for low cholesterol and high fiber diets has increased soybean's importance as a health food.

Soybean varieties grown in the United States have a narrow genetic base. Six introductions, 'Mandarin,' 'Manchu,' 'Mandarin' (Ottawa), "Richland,' 'AK' (Harrow), and 'Mukden,' contributed nearly 70% of the germplasm represented in 136 cultivar releases. To date, modern day cultivars can be traced back from these six soybean strains from China. In a study conducted by Cox et al., *Crop Sci.* 25:529-532 (1988), the soybean germplasm is comprised of 90% adapted materials, 9% un-adapted, and only 1% from exotic species. The genetic base of cultivated soybean could be widened through exotic species. In addition, exotic species may possess such key traits as disease, stress, and insect resistance.

The availability of a specific micronutrient, such as iron (Fe), is often related to soil characteristics. Soil pH has a major impact on the availability of Fe. Iron deficiency has been a common, serious, and yield limiting problem for soybean production in some parts of the United States.

Iron is one of the necessary micronutrients for soybean plant growth and development. Iron is needed for the development of chlorophyll. It is involved in energy transfer, plant respiration, and plant metabolism. It is a constituent of certain enzymes and proteins in plants. Iron is also necessary for soybean root nodule formation and has a role in N-fixation, thus, low levels of Fe can lead to reduction in N-fixation.

When Fe is limited, iron deficiency chlorosis (IDC) can be expressed in soybean plants. IDC in soybean is the result of a complex interaction among many factors including soil chemistry, environmental conditions, and soybean physiology and genetics. The most common IDC symptom is interveinal chlorosis in which leaf tissue of newly developed soybean leaves turn yellow, while the veins remain green. The leaves may develop necrotic spots that eventually coalesce and fall off the plant. Iron deficiency symptoms are similar to that of Manganese (Mn), therefore, only soil and tissue analysis can confirm the deficiency.

Severe yield reductions have been reported from IDC throughout the North-Central U.S with losses estimated to be around $120 million annually. Soybean IDC symptoms typically occur between the first and third trifoliate stage. Depending on the severity of the problem, symptoms might improve later in the season. Severe stress can stunt soybean plants causing more than 50% or more yield reduction and may even kill the plants.

Some calcareous soils with pH more than 7.4, heavy, poorly drained, and compacted soils may exhibit IDC symptoms, due to insufficient Fe uptake. However, soil pH is not a good indicator and does not correlate very well with IDC. Symptoms are highly variable between years and varieties and depend on other soil factors and weather conditions.

There is a direct relationship between IDC and high concentrations of calcium carbonate and soluble salts. Iron uptake is adversely impacted by high concentrations of phosphorous (P), manganese (Mn), and zinc (Zn). High levels of calcium (Ca) in the soil cause Fe molecules to bind tightly to the soil particles and become unavailable for uptake. It is important to measure the percentage of calcium carbonate and soluble salts in the soil as some combinations of percentage of free calcium carbonate and soluble salts can cause severe IDC. Sandy soils with low organic matter also may exhibit IDC symptoms.

Weather also plays a role in IDC symptoms. Cool soil temperature and wet weather, combined with soils that have marginal levels of available Fe can increase IDC symptoms.

Soybean producers have sought to develop plants tolerant to low iron growth conditions (thus not exhibiting IDC) as a cost-effective alternative or supplement to standard foliar, soil and/or seed treatments (e.g., Hintz et al. (1987) "Population development for the selection of high-yielding soybean cultivars with resistance to iron deficiency chlorosis," Crop Sci. 28:369-370). Studies also suggest that cultivar selection is more reliable and universally applicable than foliar sprays or iron seed treatment methods, though environmental and cultivar selection methods can also be used effectively in combination. See also, Goos and Johnson (2000) "A Comparison of Three Methods for Reducing Iron-Deficiency Chlorosis in Soybean" Agronomy Journal 92:1135-1139; and Goos and Johnson "Seed Treatment, Seeding Rate, and Cultivar Effects on Iron Deficiency Chlorosis of Soybean" Journal of Plant Nutrition 24 (8) 1255-1268. U.S. Pat. No. 7,977,533 discloses genetic loci associated with iron deficiency tolerance in soybean.

Soybean cultivar improvement for IDC tolerance can be performed using classical breeding methods, or, more preferably, using marker assisted selection (MAS). Genetic markers for low iron growth condition tolerance/susceptibility have been identified (e.g., Lin et al. (2000) "Molecular characterization of iron deficiency chlorosis in soybean" Journal of Plant Nutrition 23:1929-1939). Recent work suggests that marker assisted selection is particularly beneficial when selecting plants because the strength of environmental effects on chlorosis expression impedes progress in improving tolerance. See also, Charlson et al., "Associating SSR Markers with Soybean Resistance to Iron Chlorosis," Journal of Plant Nutrition, vol. 26, nos. 10 & 11; 2267-2276 (2003). Molecular Markers and Marker Assisted Selection. U.S. Pat. No. 7,977,533 also discloses genetic loci associated with iron deficiency tolerance in soybean.

There is a need in the art of plant breeding to identify additional markers linked to genomic regions associated with tolerance to low iron growth conditions (e.g., IDC tolerance) in soybean. There is in particular a need for numerous markers that are closely associated with low iron growth condition tolerance in soybean that permit introgression of such regions in the absence of extraneous linked DNA from the source germplasm containing the regions. Additionally, there is a need for rapid, cost-efficient method to assay the absence or presence of IDC tolerance loci in soybean.

SUMMARY OF INVENTION

In certain embodiments, the present invention provides for compositions and methods for identifying soybean plants or germplasm with tolerance to low iron growth conditions. Certain embodiments of the invention provide for polymorphic nucleic acids useful for identifying or producing soybean plants or germplasm with tolerance to low iron growth conditions. Certain embodiments of the invention also provide for methods for selecting, producing, and/or breeding soybean plants or germplasm with tolerance to low iron growth conditions. In certain embodiments, the present invention further relates to methods to determine the presence or absence of quantitative trait loci (QTL) conferring tolerance to low iron growth conditions to soybean plants, including but not limited to exotic germplasm, populations, lines, elite lines, cultivars and varieties. In certain embodiments, the invention relates to methods that provide for identification of molecular markers associated with low iron growth condition tolerance trait QTL. In certain embodiments, the present invention relates to the use of molecular markers to screen and select for low iron growth condition tolerance within soybean plants, including but not limited to exotic germplasm, populations, lines, elite lines, and varieties.

Methods of identifying a soybean plant that comprises a genotype associated with a low iron growth condition tolerant phenotype are provided. In certain embodiments, these methods of identifying a soybean plant that comprises a genotype associated with a low iron growth condition tolerant phenotype can comprise: i) detecting in the soybean plant an allele in at least one polymorphic nucleic acid marker locus associated with the low iron growth condition tolerant phenotype wherein the marker locus is in a: a) linkage group N genomic region flanked by loci Glyma03g34510 and Glyma03g42250, b) linkage group L genomic region flanked by loci Glyma19g32880 and Contig9146, c) linkage group O genomic region flanked by loci NS0116559 and Gm_W82_CR10.G236520, d) linkage group O genomic region flanked by loci NS0116559 and TA68568_3847, e) linkage group O genomic region flanked by loci Glyma10g37560 and Gm_W82_CR10.G236520, f) linkage group M genomic region flanked by loci Gm_W82_CR07.G4950 and Glyma070g33560, g) linkage group M genomic region flanked by loci Gm_W82_CR07.G4950 and Glyma07g12210, or h) linkage group M genomic region flanked by loci Glyma07g29640 and Glyma070g33560; and ii) denoting that said plant comprises a genotype associated with a low iron growth condition tolerant phenotype. In certain embodiments, these methods can further comprise the step of selecting the denoted plant from a population of plants. In certain embodiments of these methods, a denoted and/or selected plant exhibits a low iron growth condition tolerant phenotype. In certain embodiments of any of the aforementioned methods, a genotype associated with a low iron growth condition phenotype comprises at least one allele associated with a low iron growth condition tolerant phenotype of a polymorphic nucleic acid marker selected from the group consisting of SEQ ID NOs: 1-7, 20-30, and 47-51.

Also provided herein are methods for obtaining a soybean plant comprising in its genome at least one low iron growth condition tolerance locus. In certain embodiments, the methods for obtaining a soybean plant comprising in its genome at least one low iron growth condition tolerance locus can comprise genotyping a plurality of soybean plants with respect to at least one locus in a: a) linkage group N genomic region flanked by loci Glyma03g34510 and Glyma03g42250, b) linkage group L genomic region flanked by loci Glyma19g32880 and Contig9146, c) linkage group O genomic region flanked by loci NS0116559 and Gm_W82_CR10.G236520, d) linkage group O genomic region flanked by loci NS0116559 and TA68568_3847, e) linkage group O genomic region flanked by loci Glyma10g37560 and Gm_W82_CR10.G236520, f) linkage group M genomic region flanked by loci Gm_W82_CR07.G4950 and Glyma070g33560, g) linkage group M genomic region flanked by loci Gm_W82_CR07.G4950 and Glyma07g12210, or h) linkage group M genomic region flanked by loci Glyma07g29640 and Glyma070g33560; and ii) selecting a soybean plant comprising in its genome at least one low iron growth condition tolerance locus comprising a genotype associated with a low iron growth condition tolerant phenotype. In certain embodiments of these methods, the selected soybean plant exhibits tolerance to low iron growth conditions. In certain embodiments of the aforementioned methods, the methods can further comprise assaying the selected plant of step (ii) for a low iron growth condition tolerant phenotype. In certain embodiments of any of the aforementioned methods, the methods can further comprise a step wherein a low iron growth condition tolerance locus is genotyped for at least one allele of a polymorphic nucleic acid marker selected from the group consisting of SEQ ID NOs: 1-7, 20-30, and 47-51.

Also provided are methods for identifying a soybean plant comprising in its genome at least one introgressed low iron growth condition tolerance locus. In certain embodiments, methods for identifying a soybean plant comprising in its genome at least one introgressed low iron growth condition tolerance locus can comprise crossing a first soybean plant with a second soybean plant, the second plant comprising: i) a low iron growth condition tolerance locus in a: a) linkage group N genomic region flanked by loci Glyma03g34510 and Glyma03g42250, b) linkage group L genomic region flanked by loci Glyma19g32880 and Contig9146, c) linkage group O genomic region flanked by loci NS0116559 and Gm_W82_CR10.G236520, d) linkage group O region flanked by loci NS0116559 and TA68568_847, e) linkage group O genomic region flanked by loci Glyma10g37560 and Gm_W82_CR10.G236520, f) linkage group M genomic region flanked by loci Gm_W82_CR07.G4950 and Glyma070g33560, g) linkage group M genomic region flanked by loci Gm_W82_CR07.G4950 and Glyma07g12210, or h) linkage group M genomic region flanked by loci Glyma07g29640 and Glyma070g33560; and ii) detecting the polymorphic nucleic acid in at least one soybean plant from the population of soybean plants, wherein the one soybean plant lacks the additional polymorphic locus, thereby identifying a soybean plant comprising in its genome at least one introgressed low iron growth condition tolerance locus. In certain embodiments, these methods can further comprise the step of selecting the one soybean plant, thereby obtaining a soybean plant comprising in its genome at least one introgressed low iron growth condition tolerance locus. In certain embodiments of any of the aforementioned methods, the identified or the selected plant is tolerant to low iron growth conditions. In certain embodiments of any of the aforementioned methods, the identified or selected plant is assayed for tolerance to low iron growth conditions. In certain embodiments of any of the aforementioned methods, the additional polymorphic locus is detected with a genotypic marker, a phenotypic marker, or both.

In certain embodiments of any of the aforementioned methods, the additional polymorphic locus is a linked polymorphic locus located on linkage group N, L, O, or M, but not within a: a) linkage group N genomic region flanked by loci Glyma03g34510 and Glyma03g42250, b) linkage group L genomic region flanked by loci Glyma19g32880 and Contig9146, c) linkage group O genomic region flanked by loci NS0116559 and Gm_W82_CR10.G236520, d) linkage group O genomic region flanked by loci NS0116559 and TA68568_3847, e) linkage group O genomic region flanked by loci Glyma10g37560 and Gm_W82_CR10.G236520, f) linkage group M genomic region flanked by loci Gm_W82_CR07.G4950 and Glyma07␣g33560, g) linkage group M genomic region flanked by loci Gm_W82_CR07.G4950 and Glyma07g12210, or h) linkage group M genomic region flanked by loci Glyma07g29640 and Glyma07␣g33560.

Also provided herein are soybean plants obtainable by any of the aforementioned methods. Soybean plants comprising genomic regions associated with a low iron growth condition tolerant phenotype wherein immediately adjacent genomic regions and/or one or more adjacent genomic regions characteristic of soybean germplasms that lack the genomic regions associated with a low iron growth condition phenotype and/or that are distinct from the germplasm from which the genomic region is derived are also provided.

In certain embodiments, a soybean plant comprising i) a low iron growth condition tolerance locus in a: a) linkage group N genomic region flanked by loci Glyma03g34510 and Glyma03g42250, b) linkage group L genomic region flanked by loci Glyma19g32880 and Contig9146, c) linkage group O genomic region flanked by loci NS0116559 and Gm_W82_CR10.G236520, d) linkage group O genomic region flanked by loci NS0116559 and TA68568_3847, e) linkage group O genomic region flanked by loci Glyma10g37560 and Gm_W82_CR10.G236520, f) linkage group M genomic region flanked by loci Gm_W82_CR07.G4950 and Glyma07␣g33560, g) linkage group M genomic region flanked by loci Gm_W82_CR07.G4950 and Glyma07g12210, or h) linkage group M genomic region flanked by loci Glyma07g29640 and Glyma07␣g33560; and ii) one or more polymorphic loci comprising alleles or combinations of alleles that are not found in a low iron growth condition tolerant soybean varieties harboring said tolerance locus, and that are linked to said locus, wherein said soybean plant is tolerant to low iron growth conditions is provided.

In any of the aforementioned embodiments, the soybean plant can comprise an allele of one or more polymorphic markers selected from the group consisting of SEQ ID NOs: 1-7, 20-30, and 47-51. In certain embodiments, the nucleic acid can further comprise a detectable moiety. In certain embodiments, the detectable moiety can be selected from the group consisting of a chromophore, a fluorophore, and a hapten.

Certain other methods of identifying a soybean plant that comprises a genotype associated with a low iron growth condition tolerant phenotype are provided. In certain embodiments, these methods comprise: i) detecting in said soybean plant an allele in at least one polymorphic nucleic acid marker locus associated with the low iron growth condition tolerant phenotype wherein the marker locus is in a: a) linkage group G genomic region flanked by loci FE898349 and Cf14688d, b) linkage group A1 genomic region flanked by loci Mt7 and BARCSOYSSR_05_0640, c) linkage group M genomic region flanked by loci BQ081048 and TA53357_3847, d) linkage group D2 genomic region flanked by loci BG726970 and Contig41076, e) linkage group L genomic region flanked by loci Glyma19g01630 and TC27203, or f) linkage group K genomic region flanked by loci Cf4289d and Cf974d; and ii) denoting that said plant comprises a genotype associated with a low iron growth condition tolerant phenotype. In certain embodiments, these methods can further comprise the step of selecting said denoted plant from a population of plants. In certain embodiments of these methods, a denoted and/or selected plant exhibits a low iron growth condition tolerant phenotype. In certain embodiments of any of the aforementioned methods, a genotype associated with a low iron growth condition tolerant phenotype comprises at least one allele associated with a low iron growth condition tolerant phenotype of a polymorphic nucleic acid marker selected from the group consisting of SEQ ID NOs: 52-62, 71-93, 94-110, 115-123, 124-138, and 139-174.

Also provided herein are methods for obtaining a soybean plant comprising in its genome at least one locus associated with a low iron growth condition tolerant phenotype. In certain embodiments, these methods can compromising the steps of: i) genotyping a plurality of soybean plants with respect to at least one low iron growth condition tolerance locus in a:

a) linkage group G genomic region flanked by loci FE898349 and Cf14688d, b) linkage group A1 genomic region flanked by loci Mt7 and BARCSOYSSR_05_0640, c) linkage group M genomic region flanked by loci BQ081048 and TA53357_3847, d) linkage group D2 genomic region flanked by loci BG726970 and Contig41076, e) linkage group L genomic region flanked by loci Glyma19g01630 and TC27203, or f) linkage group K genomic region flanked by loci Cf4289d and Cf974d; and ii) selecting a soybean plant comprising in its genome at least one low iron growth condition tolerance locus comprising a genotype associated with a low iron growth condition tolerant phenotype. In certain embodiments of these methods, the selected soybean plant exhibits tolerance to low iron growth conditions. In certain embodiments of the aforementioned methods, the methods can further comprise assaying said selected plant of step (ii) for a low iron growth condition tolerant phenotype. In certain embodiments of any of the aforementioned methods, the methods can further comprises a step wherein said low iron growth condition tolerance locus is genotyped for at least one polymorphic allele of any of the markers selected from the group consisting of SEQ ID NOs: 52-62, 71-93, 94-110, 115-123, 124-138, and 139-174.

Also provided are methods for identifying a soybean plant comprising in its genome at least one introgressed low iron growth condition tolerance locus. In certain embodiments, these methods can comprising crossing a first soybean plant with a second soybean plant, the second plant comprising: i) a low iron growth condition tolerance locus in a: a) linkage group G genomic region flanked by loci FE898349 and Cf14688d, b) linkage group A1 genomic region flanked by loci Mt7 and BARCSOYSSR_05_0640, c) linkage group M genomic region flanked by loci BQ081048 and TA53357_3847, d) linkage group D2 genomic region flanked by loci BG726970 and Contig41076, e) linkage group L genomic region flanked by loci Glyma19g01630 and TC27203, or f) linkage group K genomic region flanked by loci Cf4289d and Cf974d; and ii) at least one additional polymorphic locus located outside of said region, to obtain a population of soybean plants segregating for the low iron growth condition tolerance loci and said at least one additional polymorphic locus; and detecting said polymorphic nucleic acid in at least one soybean plant from said population of soybean plants, wherein said one soybean plant lacks said additional polymorphic locus, thereby identifying a soybean plant comprising in its genome at least one introgressed low iron growth condition tolererance locus. In certain embodiments, these methods can further comprise the step of selecting said one soybean plant, thereby obtaining a soybean plant comprising in its genome at least one introgressed low iron growth condition tolerance locus. In certain embodiments of any of the aforementioned methods, the identified or selected plant is tolerant to low iron growth conditions. In certain embodiments of any of the aforementioned methods, the identified or selected plant is assayed for tolerance to low iron growth conditions. In certain embodiments of any of the aforementioned inventions, the additional polymorphic locus is detected with a genotypic marker, a phenotypic marker, or both.

In certain embodiments of any of the aforementioned methods, the additional polymorphic locus is a linked polymorphic locus located on linkage group G, A1, M, D2, L, or K, but not within a: a) linkage group G genomic region flanked by loci FE898349 and Cf14688d, b) linkage group A1 genomic region flanked by loci Mt7 and BARCSOYSSR_05_0640, c) linkage group M genomic region flanked by loci BQ081048 and TA53357_3847, d) linkage group D2 genomic region flanked by loci BG726970 and Contig41076, e) linkage group L genomic region flanked by loci Glyma19g01630 and TC27203, or f) linkage group K genomic region flanked by loci Cf4289d and Cf974d.

Also further provided herein are soybean plants obtainable by any of the aforementioned methods. Soybean plants comprising genomic regions associated with a low iron growth condition tolerant phenotype wherein immediately adjacent genomic regions and/or one or more adjacent genomic regions characteristic of soybean germplasms that lack the genomic regions associated with a low iron growth condition phenotype and/or that are distinct from the germplasm from which the genomic region is derived are also provided.

In certain embodiments, a soybean plant comprises: i) a low iron growth condition tolerance locus in a: a) linkage group G genomic region flanked by loci FE898349 and Cf14688d, b) linkage group A1 genomic region flanked by loci Mt7 and BARCSOYSSR_05_0640, c) linkage group M genomic region flanked by loci BQ081048 and TA53357_3847, d) linkage group D2 genomic region flanked by loci BG726970 and Contig41076, e) linkage group L genomic region flanked by loci Glyma19g01630 and TC27203, or f) linkage group K genomic region flanked by loci Cf4289d and Cf974d; and ii) one or more polymorphic loci comprising alleles or combinations of alleles that are not found in a low iron growth condition tolerant soybean varieties harboring said tolerance locus, and that are linked to said locus, wherein said soybean plant is tolerant to low iron growth conditions is provided.

In any of the aforementioned embodiments, the soybean plant can comprise an allele of one or more markers selected from the group consisting of SEQ ID NOs: 52-62, 71-93, 94-110, 115-123, 124-138, or 139-174. In certain embodiments, the nucleic acid can further comprise a detectable moiety. In certain embodiments, the detectable moiety can be selected from the group consisting of a chromophore, a fluorophore, and a hapten. Also provide herewith are isolated nucleic acid molecules selected from the group consisting SEQs ID NO: 1-186.

Further areas of applicability will become apparent from the description provided herein. It should be understood that the description and specific examples are intended for purposes of illustration only and are not intended to limit the scope of the present disclosure.

DESCRIPTION OF INVENTION

I. Definitions

Unless otherwise indicated herein, nucleic acid sequences are written left to right in 5' to 3' orientation. Numeric ranges recited within the specification are inclusive of the numbers defining the range and include each integer or any non-integer fraction within the defined range. Unless defined otherwise, all technical and scientific terms used herein have the same meaning as commonly understood by one of ordinary skill in the art to which the invention pertains.

As used herein, an "allele" refers to one of two or more alternative forms of a genomic sequence at a given locus on a chromosome. When all the alleles present at a given locus on a chromosome are the same, that plant is homozygous at that locus. If the alleles present at a given locus on a chromosome differ, that plant is heterozygous at that locus.

As used herein, the term "bulk" refers to a method of managing a segregating population during inbreeding that involves growing the population in a bulk plot, harvesting the self-pollinated seed of plants in bulk, and using a sample of the bulk to plant the next generation.

As used herein, the term "comprising" means "including but not limited to".

As used herein, the term "denoting" when used in reference to a plant genotype refers to any method whereby a plant is indicated to have a certain genotype. Such indications of a certain genotype include, but are not limited to, any method where a plant is physically marked or tagged. Physical markings or tags that can be used include, but not limited to, a barcode, a radio-frequency identification (RFID), a label or the like. Indications of a certain genotype also include, but are not limited to, any entry into any type of written or electronic database whereby the plant's genotype is provided.

As used herein, the term "locus" refers to a position on a genomic sequence that is usually found by a point of reference; e.g., a short DNA sequence that is a gene, or part of a gene or intergenic region. A locus may refer to a nucleotide position at a reference point on a chromosome, such as a position from the end of the chromosome.

As used herein, "linkage group N" corresponds to the soybean linkage group N described in Choi, et al., Genetics. 2007 May; 176(1): 685-696. Linkage group N, as used herein, also corresponds to soybean chromosome 3 (as described on the World Wide Web at soybase.org/LG2Xsome.php).

As used herein, "linkage group M" corresponds to the soybean linkage group M described in Choi, et al., Genetics. 2007 May; 176(1): 685-696. Linkage group M, as used herein, also corresponds to soybean chromosome 7 (as described on the World Wide Web at soybase.org/LG2Xsome.php).

As used herein, "linkage group L" corresponds to the soybean linkage group L described in Choi, et al., Genetics. 2007 May; 176(1): 685-696. Linkage group L, as used herein, also corresponds to soybean chromosome 19 (as described on the World Wide Web at soybase.org/LG2Xsome.php).

As used herein, "linkage group O" corresponds to the soybean linkage group O described in Choi, et al., Genetics. 2007 May; 176(1): 685-696. Linkage group O, as used herein, also corresponds to soybean chromosome 10 (as described on the World Wide Web at soybase.org/LG2Xsome.php).

As used herein, "linkage group G" corresponds to the soybean linkage group G described in Choi, et al., Genetics. 2007 May; 176(1): 685-696. Linkage group G, as used herein, also corresponds to soybean chromosome 18 (as described on the World Wide Web at soybase.org/LG2Xsome.php).

As used herein, "linkage group A1" corresponds to the soybean linkage group A1 described in Choi, et al., Genetics. 2007 May; 176(1): 685-696. Linkage group A1, as used herein, also corresponds to soybean chromosome 5 (as described on the World Wide Web at soybase.org/LG2Xsome.php).

As used herein, "linkage group D2" corresponds to the soybean linkage group D2 described in Choi, et al., Genetics. 2007 May; 176(1): 685-696. Linkage group D2, as used herein, also corresponds to soybean chromosome 17 (as described on the World Wide Web at soybase.org/LG2Xsome.php).

As used herein, "linkage group L" corresponds to the soybean linkage group L described in Choi, et al., Genetics. 2007 May; 176(1): 685-696. Linkage group L, as used herein, also corresponds to soybean chromosome 19 (as described on the World Wide Web at soybase.org/LG2Xsome.php).

As used herein, "linkage group K" corresponds to the soybean linkage group K described in Choi, et al., Genetics. 2007 May; 176(1): 685-696. Linkage group K, as used herein, also corresponds to soybean chromosome 9 (as described on the World Wide Web at soybase.org/LG2Xsome.php).

As used herein, "polymorphism" means the presence of one or more variations of a nucleic acid sequence at one or more loci in a population of at least two members. The variation can comprise, but is not limited to, one or more nucleotide base substitutions, the insertion of one or more nucleotides, a nucleotide sequence inversion, and/or the deletion of one or more nucleotides.

As used herein, "genotype" means the genetic component of the phenotype and it can be indirectly characterized using markers or directly characterized by nucleic acid sequencing.

As used herein, the term "introgressed", when used in reference to a genetic locus, refers to a genetic locus that has been introduced into a new genetic background. Introgression of a genetic locus can thus be achieved through both plant breeding methods or by molecular genetic methods. Such molecular genetic methods include, but are not limited to, various plant transformation techniques and/or methods that provide for homologous recombination, non-homologous recombination, site-specific recombination, and/or genomic modifications that provide for locus substitution or locus conversion. In certain embodiments, introgression could thus be achieved by substitution of a locus not associated with tolerance to low iron growth conditions with a corresponding locus that is associated with low iron growth condition tolerance or by conversion of a locus from a non-tolerant genotype to a tolerant genotype.

As used herein, "linkage" refers to relative frequency at which types of gametes are produced in a cross. For example, if locus A has genes "A" or "a" and locus B has genes "B" or "b" and a cross between parent I with AABB and parent B with aabb will produce four possible gametes where the genes are segregated into AB, Ab, aB and ab. The null expectation is that there will be independent equal segregation into each of the four possible genotypes, i.e. with no linkage ¼ of the gametes will of each genotype. Segregation of gametes into a genotypes differing from ¼ are attributed to linkage.

As used herein, the termed "linked", when used in the context of markers and/or genomic regions, means that the markers and/or genomic regions are located on the same linkage group or chromosome.

As used herein, "marker" means a detectable characteristic that can be used to discriminate between organisms. Examples of such characteristics include, but are not limited to, genetic markers, biochemical markers, fermentation yield, fermentation efficiency, energy yield, secondary compounds, metabolites, morphological characteristics, and agronomic characteristics.

As used herein, "marker assay" means a method for detecting a polymorphism at a particular locus using a particular method. Marker assays thus include, but are not limited to, measurement of at least one phenotype (such as seed color, flower color, or other visually detectable trait as well as any biochemical trait), restriction fragment length polymorphism (RFLP), single base extension, electrophoresis, sequence alignment, allelic specific oligonucleotide hybridization (ASO), random amplified polymorphic DNA (RAPD), microarray-based polymorphism detection technologies, and the like.

As used herein, "phenotype" means the detectable characteristics of a cell or organism which can be influenced by gene expression.

As used herein, a "nucleic acid molecule," of naturally occurring origins or otherwise, may be an "isolated" nucleic acid molecule. An isolated nucleic acid molecule is one removed from its native cellular and chromosomal environment. The term "isolated" is not intended to encompass molecules present in their native state. If desired, an isolated nucleic acid may be substantially purified, meaning that it is the predominant species present in a preparation. A substantially purified molecule may be at least about 60% free, preferably at least about 75% free, more preferably at least about 90% free, and most preferably at least about 95% free from the other molecules (exclusive of solvent) present in the preparation.

As used herein, "quantitative trait locus (QTL)" means a locus that controls to some degree numerically representable traits that are usually continuously distributed.

As used herein, the term "soybean" means *Glycine max* and includes all plant varieties that can be bred with soybean, including wild soybean species. In certain embodiments, soybean plants from the species *Glycine max* and the subspecies *Glycine max* L. ssp. max or *Glycine max* ssp. *formosana* can be genotyped using the compositions and methods of the present invention. In an additional aspect, the soybean plant is from the species *Glycine soja*, otherwise known as wild soybean, can be genotyped using these compositions and methods. Alternatively, soybean germplasm derived from any of *Glycine max, Glycine max* L. ssp. *max, Glycine max* ssp. *Formosana*, and/or *Glycine soja* can be genotyped using compositions and methods provided herein.

As used herein, the term "single nucleotide polymorphism," also referred to by the abbreviation "SNP," means a polymorphism at a single site wherein the polymorphism constitutes any or all of a single base pair change, an insertion of one or more base pairs, and/or a deletion of one or more base pairs.

As used herein, the phrases "low iron," "low-available iron," "low soluble iron," "low iron conditions," "low iron growth conditions," iron shortage" or "iron deficiency" or the like refer to conditions where iron availability is less than optimal for soybean growth, and can cause plant pathology, e.g., IDC, due to the lack of metabolically-available iron. It is recognized that under "iron deficient" conditions, the absolute concentration of atomic iron may be sufficient, but the form of the iron (e.g., its incorporation into various molecular structures) and other environmental factors may make the iron unavailable for plant use. For example, high carbonate levels, high pH, high salt content, herbicide applications, cool temperatures, saturated soils, or other environmental factors can decrease iron solubility, and reduce the solubilized forms of iron that the plant requires for uptake. One of skill in the art is familiar with assays to measure iron content of soil, as well as those concentrations of iron that are optimal or sub-optimal for plant growth.

As used herein, the terms "tolerance" or "improved tolerance" in reference to a soybean plant grown in low iron growth conditions is an indication that the soybean plant is less affected by the low-available iron conditions with respect to yield, survivability and/or other relevant agronomic measures, compared to a less tolerant, more "susceptible" plant. Tolerance is a relative term, indicating that a tolerant" plant survives and/or produces better yield of soybean in low-available iron growth conditions compared to a different (less tolerant) plant (e.g., a different soybean strain) grown in similar low-available iron conditions. That is, the low-available iron growth conditions cause a reduced decrease in soybean survival and/or yield in a tolerant soybean plant, as compared to a susceptible soybean plant. As used in the art, iron-deficiency "tolerance" is sometimes used interchangeably with iron-deficiency "resistance."

One of skill will appreciate that soybean plant tolerance to low-available iron conditions varies widely, and can represent a spectrum of more-tolerant or less-tolerant phenotypes. However, by simple observation, one of skill can generally determine the relative tolerance or susceptibility of different plants, plant lines or plant families under low-available iron conditions, and furthermore, will also recognize the phenotypic gradations of "tolerant."

In one example, a plant's tolerance can be approximately quantitated using a chlorosis scoring system. In such a system, a plant that is grown in a known iron-deficient area, or in low-available iron experimental conditions, and is assigned a tolerance rating of between 1 (highly susceptible; most or all plants dead; those that live are stunted and have little living tissue) to 9 (highly tolerant; yield and survivability not significantly affected; all plants normal green color). See also, Dahiya and Singh (1979) "Effect of salinity, alkalinity and iron sources on availability of iron," Plant and Soil 51:13-18.

II. Description of the Invention: Overview

In accordance with the present invention, Applicants have discovered genomic regions, associated markers, and associated methods for identifying and associating genotypes that effect an iron deficient growth condition tolerance trait. For example, in one embodiment, a method of the invention comprises screening for alleles of polymorphic nucleic acid markers, including, but not limited to NS0202842 (SEQ ID NO:4), NS0206055 (SEQ ID NO: 22), NS0092960 (SEQ ID NO: 26), and NS0202730 (SEQ ID NO: 50) that are associated with low iron growth condition tolerance loci described herein.

The advent of molecular genetic markers has facilitated mapping and selection of agriculturally important traits in soybean. Markers tightly linked to tolerance genes are an asset in the rapid identification of tolerant soybean lines on the basis of genotype by the use of marker assisted selection (MAS). Introgressing tolerance genes into a desired cultivar is also facilitated by using suitable nucleic acid markers.

The use of markers to infer a phenotype of interest results in the economization of a breeding program by substituting costly, time-intensive phenotyping assays with genotyping assays. Further, breeding programs can be designed to explicitly drive the frequency of specific, favorable phenotypes by targeting particular genotypes (U.S. Pat. No. 6,399, 855). Fidelity of these associations may be monitored continuously to ensure maintained predictive ability and, thus, informed breeding decisions (US Patent Application 2005/ 0015827). In this case, costly, time-intensive phenotyping assays required for determining if a plant or plants contains a genomic region associated with a low iron growth condition tolerant phenotype can be supplanted by genotypic assays that provide for identification of a plant or plants that contain the desired genomic region.

III. QTL Associated with Tolerance to Low Iron Growth Conditions

Provided herewith are certain QTL that have been identified as associated with a desirable phenotype of tolerance to growth in low iron conditions when present in certain allelic forms.

The several soybean QTL provided—that can be associated with a desirable low iron growth condition tolerant phenotype when present in certain allelic forms—are located on soybean chromosome 3 (soybean linkage group N), soybean chromosome 7 (soybean linkage group M), soybean chromosome 19 (soybean linkage group L), and soybean chromosome 10 (soybean linkage group O).

A series of public and other markers useful in practicing the methods of this invention are provided herewith in Tables 1-10. Nucleic acid sequences for certain non-public markers useful in the practice of the invention are provided herewith in the accompanying sequence listing, which is incorporated herein by reference in its entirety.

Tables 1, 4, 6, and 9 (corresponding to chromosomes 3, 19, 10, and 7, respectively) shows the relative positions of certain markers that have been disclosed in public databases and non-public (bolded) polymorphic nucleic acid markers, designated SEQ ID NOs, genetic positions (cM) on the chromosome, the allelic forms of certain polymorphic nucleic acid markers associated with a low iron growth condition tolerant phenotype, the allelic forms of those polymorphic nucleic acid markers not associated with the low iron growth condition tolerant phenotype, the polymorphic position within the sequence of the polymorphic nucleic acid marker, and a designation of whether a particular marker has been identified as within a genomic region associated with a low iron growth condition tolerant phenotype.

Tables 2, 5, 7, and 10 (corresponding to chromosomes 3, 19, 10, and 7, respectively) provides for each polymorphic nucleic acid marker/SEQ ID NO the linkage group corresponding to the chromosome and the relative physical map positions of the markers.

Tables 3, 8 (corresponding to chromosomes 3 and 10, respectively) provide for certain polymorphic nucleic acid markers, the type of marker, and primer and probe sequences useful in detecting such markers.

Table 12 of the Appendix to the Specification, which is incorporated herein by reference in its entirety, discloses the sources of certain of the markers contained in Tables 1-10.

TABLE 1

Chromosome 3 - QTL on chromosome 3 associated with a low iron growth condition tolerant phenotype.

| Marker or Locus Name | SEQ ID NO | cM Map Position on Chromosome Three (3) | Allelic Form(s) Associated With Low Fe Tolerance Phenotype[1] | Allelic Form(s) Not-Associated with Low Fe Tolerance Phenotype[1] | Polymorphic Position | Identified Within Region Associated With Low Fe Tolerance |
|---|---|---|---|---|---|---|
| Glyma03g34510 | — | — | — | — | — | — |
| Gm_W82_CR03.G378360 | — | — | — | — | — | — |
| Glyma03g34760 | — | — | — | — | — | — |
| Glyma03g34860 | — | — | — | — | — | — |
| NS0202712 | 1 | 122.3 | AA | TT | 218 | *** |
| Glyma03g35130 | — | — | — | — | — | *** |
| Glyma03g35280 | — | — | — | — | — | *** |
| NS0129403 | 2 | 130.7 | GG | AA | 83 | *** |
| NS0115624 | 3 | 131 | TT | AA | 582 | *** |
| Glyma03g36800 | — | — | — | — | — | *** |
| Glyma03g38030 | — | — | — | — | — | *** |
| NS0202842 | 4 | 141 | CC | TT | 145 | *** |
| NS0122122 | 5 | 141.3 | CC | TT | 271 | *** |
| NS0205984 | 6 | 141.9 | GG | AA | 244 | *** |
| Pvcon3607 | — | — | — | — | — | *** |
| Glyma03g39610 | — | — | — | — | — | *** |
| FE710890 | — | — | — | — | — | *** |
| NS0202698 | 7 | 149.8 | GG | AA | 421 | *** |
| Glyma03g41830 | — | — | — | — | — | — |
| Glyma03g42250 | — | — | — | — | — | — |

TABLE 2

Chromosome 3 - Physical positions of certain genetic markers on soybean chromosome 3 in proximity to QTL associated with a low iron growth condition tolerant phenotype.

| Marker or Locus Name | SEQ ID NO | LG | Chromosome | Middle Position | Start | Stop |
|---|---|---|---|---|---|---|
| Glyma03g34510 | — | N | 3 | 41915727 | 41914204 | 41917250 |
| Gm_W82_CR03.G378360 | — | N | 3 | 41915733 | 41914204 | 41917263 |
| Glyma03g34760 | — | N | 3 | 42086656 | 42085228 | 42088084 |
| Glyma03g34860 | — | N | 3 | 42164646 | 42160939 | 42168354 |
| NS0202712 | 1 | N | 3 | 42243449 | 42243249 | 42243649 |
| Glyma03g35130 | — | N | 3 | 42445457 | 42444310 | 42446604 |
| Glyma03g35280 | — | N | 3 | 42553329 | 42551024 | 42555635 |
| NS0129403 | 2 | N | 3 | 43515346 | 43515925 | 43514768 |
| NS0115624 | 3 | N | 3 | 43561673 | 43562124 | 43561223 |
| Glyma03g36800 | — | N | 3 | 43651286 | 43650506 | 43652066 |
| Glyma03g38030 | — | N | 3 | 44472415 | 44469992 | 44474838 |
| NS0202842 | 4 | N | 3 | 45075121 | 45075320 | 45074923 |
| NS0122122 | 5 | N | 3 | 45114092 | 45113696 | 45114489 |
| NS0205984 | 6 | N | 3 | 45207137 | 45207317 | 45206958 |
| Pvcon3607 | — | N | 3 | 45618970 | 45618216 | 45619724 |
| Glyma03g39610 | — | N | 3 | 45621485 | 45618205 | 45624765 |
| FE710890 | — | N | 3 | 45622786 | 45620962 | 45624610 |
| NS0202698 | 7 | N | 3 | 46401175 | 46400931 | 46401420 |
| Glyma03g41830 | — | N | 3 | 47201754 | 47200244 | 47203264 |
| Glyma03g42250 | — | N | 3 | 47498375 | 47496922 | 47499828 |

TABLE 3

Chromosome 3-Marker type and nucleic acid primers and probes useful in the detection of certain alleles of polymorphic nucleic acid markers associated with an iron deficiency growth condition tolerant phenotype.

| Marker or Locus Name | SEQ ID NO | Marker Type | Sequence |
|---|---|---|---|
| NS0129403 | 2 | TAQMAN | — |
| Forward Primer | 8 | — | GCGGATAGCCGGATAGCAT |
| Reverse Primer | 9 | — | GCATACAACTTAGTTTTATATACATATATAGTGTATATATATCA |
| Vic Probe | 10 | — | CATGTAACAGAGGTCA |
| Fam Probe | 11 | — | ATGTAGCAGAGGTCA |
| NS0115624 | 3 | TAQMAN | — |
| Forward Primer | 12 | — | GAGTCAAAGTAGGAATCTTTTCGCATA |
| Reverse Primer | 13 | — | TTACTTTGTCCTCAGGGATGAACA |
| Vic Probe | 14 | — | TTTGCAAGTAGCGAGC |
| Fam Probe | 15 | — | TTGCATGTAGCGAGC |
| NS0122122 | 5 | TAQMAN | — |
| Forward Primer | 16 | — | GGTTCCGTCTGACAGTATTTTGG |
| Reverse Primer | 17 | — | ATGGAGAAAAGAACAGAGGTGGTT |
| Vic Probe | 18 | — | CCCAACCACCATTAT |
| Fam Probe | 19 | — | AACACCCAACTACC |

TABLE 4

Chromosome 19 - QTL on chromosome 19 associated with a low iron growth condition tolerant phenotype.

| Marker or Locus Name | SEQ ID NO | cM Map Position on chromosome nineteen (19) | Allelic Form(s) Associated With Low Fe Tolerance Phenotype[1] | Allelic Form(s) Not-Associated with Low Fe Tolerance Phenotype[1] | Polymorphic Position | Identified Within Region Associated With Low Fe Tolerance |
|---|---|---|---|---|---|---|
| Glyma19g32880 | — | — | — | — | — | — |
| Glyma19g33540 | — | — | — | — | — | — |
| NS0206298 | 20 | 107.5 | AA | CC | 1044 | *** |
| NS0205620 | 21 | 110.9 | GG | CC | 275 | *** |
| NS0206055 | 22 | 111.9 | AA | GG | 530 | *** |
| Glyma19g34480 | — | — | — | — | — | *** |
| NS0204985 | 23 | 114.1 | CC | TT | 619 | *** |
| Gm_W82_CR19.G249620 | — | — | — | — | — | — |
| Glyma19g34740 | — | — | — | — | — | — |
| NGMAX005710149 | — | — | — | — | — | — |
| 220298_3433_1666 | — | — | — | — | — | — |
| Contig13742 | — | — | — | — | — | — |
| BARCSOYSSR_19_1192 | — | — | — | — | — | — |
| Glyma19g34750 | — | — | — | — | — | — |
| Gm_W82_CR19.G249630 | — | — | — | — | — | — |
| Contig9146 | — | — | — | — | — | — |

TABLE 5

Chromosome 19 - Physical positions of certain genetic markers on soybean chromosome 19 in proximity to QTL associated with a low iron growth condition tolerant phenotype.

| Marker or Locus Name | SEQ ID NO | LG | Chromosome | Middle Position | Start | Stop |
|---|---|---|---|---|---|---|
| Glyma19g32880 | — | L | 19 | 40563828 | 40562661 | 40564996 |
| Glyma19g33540 | — | L | 19 | 41122500 | 41119227 | 41125773 |
| NS0206298 | 20 | L | 19 | 41609816 | 41609250 | 41610382 |
| NS0205620 | 21 | L | 19 | 42012550 | 42012728 | 42012372 |

TABLE 5-continued

Chromosome 19 - Physical positions of certain genetic markers on soybean chromosome 19 in proximity to QTL associated with a low iron growth condition tolerant phenotype.

| Marker or Locus Name | SEQ ID NO | LG | Chromosome | Middle Position | Start | Stop |
|---|---|---|---|---|---|---|
| NS0206055 | 22 | L | 19 | 42018389 | 42018856 | 42017922 |
| Glyma19g34480 | — | L | 19 | 42073448 | 42072643 | 42074253 |
| NS0204985 | 23 | L | 19 | 42345212 | 42344620 | 42345805 |
| Gm_W82_CR19.G249620 | — | L | 19 | 42345294 | 42344177 | 42346412 |
| Glyma19g34740 | — | L | 19 | 42345351 | 42344291 | 42346412 |
| NGMAX005710149 | — | L | 19 | 42345386 | 42345236 | 42345537 |
| 220298_3433_1666 | — | L | 19 | 42345865 | 42345741 | 42345989 |
| Contig13742 | — | L | 19 | 42346076 | 42345967 | 42346185 |
| BARCSOYSSR_19_1192 | — | L | 19 | 42347717 | 42347702 | 42347733 |
| Glyma19g34750 | — | L | 19 | 42351644 | 42350923 | 42352365 |
| Gm_W82_CR19.G249630 | — | L | 19 | 42351644 | 42350923 | 42352365 |
| Contig9146 | — | L | 19 | 42351663 | 42351579 | 42351748 |

TABLE 6

Chromosome 10 - QTL on chromosome 10 associated with a low iron growth condition tolerant phenotype.

| Marker or Locus Name | SEQ ID NO | cM Map Position on chromosome ten (10) | Allelic Form(s) Associated With Low Fe Tolerance Phenotype[1] | Allelic Form(s) Not-Associated with Low Fe Tolerance Phenotype[1] | Polymorphic Position | Identified Within Region Associated With Low Fe Tolerance |
|---|---|---|---|---|---|---|
| NS0116559 | — | — | — | — | — | — |
| Glyma10g33710 | — | — | — | — | — | — |
| TA42233_3847 | — | — | — | — | — | — |
| AF108084.1 | — | — | — | — | — | — |
| AW734581 | — | — | — | — | — | — |
| Glyma10g34260 | — | — | — | — | — | — |
| Glyma10g34280 | — | — | — | — | — | — |
| Glyma10g34290 | — | — | — | — | — | — |
| Glyma10g34460 | — | — | — | — | — | — |
| Glyma10g34600 | — | — | — | — | — | — |
| Glyma10g34630 | — | — | — | — | — | — |
| Glyma10g34850 | — | — | — | — | — | — |
| NS0120070 | 24 | 148.6 | TT | CC | 468 | *** |
| NS0097952 | 25 | 148.6 | GG | AA | 420 | *** |
| NS0092960 | 26 | 149.8 | TT | AA | 89 | *** |
| Glyma10g36370 | — | — | — | — | — | *** |
| NS0118907 | 27 | 154.2 | AA | CC | 450 | *** |
| Glyma10g37560 | — | — | — | — | — | — |
| TC354083 | — | — | — | — | — | — |
| Glyma10g37600 | — | — | — | — | — | — |
| BW595896 | — | — | — | — | — | — |
| TC130824 | — | — | — | — | — | — |
| CV528982 | — | — | — | — | — | — |
| Glyma10g37610 | — | — | — | — | — | — |
| BG511181 | — | — | — | — | — | — |
| TA68568_3847 | — | — | — | — | — | — |
| NS0204740 | 28 | 162.1 | AA | CC | 424 | *** |
| NS0205036 | 29 | 163.5 | AA | TT | 33 | *** |
| Glyma10g37910 | — | — | — | — | — | *** |
| Glyma10g37920 | — | — | — | — | — | *** |
| Gm_W82_CR10.G221330 | — | — | — | — | — | *** |
| NS0206252 | 30 | 165.8 | CC | TT | 100 | *** |
| Glyma10g38600 | — | — | — | — | — | — |
| Glyma10g40520 | — | — | — | — | — | — |
| BF631841 | — | — | — | — | — | — |
| Glyma10g41460 | — | — | — | — | — | — |
| Glyma10g41470 | — | — | — | — | — | — |
| TC412490 | — | — | — | — | — | — |
| Gm_W82_CR10.G236520 | — | — | — | — | — | — |

TABLE 7

Chromosome 10 - Physical positions of certain genetic markers on soybean chromosome 10 in proximity to QTL associated with a low iron growth condition tolerant phenotype.

| Marker or Locus Name | SEQ ID NO | LG | Chromosome | Middle Position | Start | Stop |
|---|---|---|---|---|---|---|
| NS0116559 | — | O | 10 | 42075575 | 42075167 | 42075983 |
| Glyma10g33710 | — | O | 10 | 42593023 | 42590873 | 42595174 |
| TA42233_3847 | — | O | 10 | 42593038 | 42590903 | 42595173 |
| AF108084.1 | — | O | 10 | 42593043 | 42590914 | 42595173 |
| AW734581 | — | O | 10 | 42593522 | 42591892 | 42595153 |
| Glyma10g34260 | — | O | 10 | 43021758 | 43021192 | 43022324 |
| Glyma10g34280 | — | O | 10 | 43030489 | 43029802 | 43031177 |
| Glyma10g34290 | — | O | 10 | 43035456 | 43034563 | 43036349 |
| Glyma10g34460 | — | O | 10 | 43204121 | 43201964 | 43206279 |
| Glyma10g34600 | — | O | 10 | 43366015 | 43361916 | 43370114 |
| Glyma10g34630 | — | O | 10 | 43409208 | 43408273 | 43410144 |
| Glyma10g34850 | — | O | 10 | 43607308 | 43606350 | 43608266 |
| NS0120070 | 24 | O | 10 | 44567643 | 44567905 | 44567382 |
| NS0097952 | 25 | O | 10 | 44571243 | 44571555 | 44570932 |
| NS0092960 | 26 | O | 10 | 44742555 | 44742322 | 44742789 |
| Glyma10g36370 | — | O | 10 | 45149778 | 45147589 | 45151968 |
| NS0118907 | 27 | O | 10 | 45409273 | 45409660 | 45408887 |
| Glyma10g37560 | — | O | 10 | 46113736 | 46112579 | 46114893 |
| TC354083 | — | O | 10 | 46143267 | 46141283 | 46145251 |
| Glyma10g37600 | — | O | 10 | 46143977 | 46141275 | 46146680 |
| BW595896 | — | O | 10 | 46144779 | 46144294 | 46145265 |
| TC130824 | — | O | 10 | 46145332 | 46144251 | 46146413 |
| CV528982 | — | O | 10 | 46154071 | 46153277 | 46154865 |
| Glyma10g37610 | — | O | 10 | 46156146 | 46154486 | 46157806 |
| BG511181 | — | O | 10 | 46156618 | 46156462 | 46156775 |
| TA68568_3847 | — | O | 10 | 46157451 | 46157096 | 46157806 |
| NS0204740 | 28 | O | 10 | 46254426 | 46254082 | 46254770 |
| NS0205036 | 29 | O | 10 | 46276912 | 46276995 | 46276829 |
| Glyma10g37910 | — | O | 10 | 46405425 | 46403762 | 46407089 |
| Glyma10g37920 | — | O | 10 | 46425433 | 46424402 | 46426465 |
| Gm_W82_CR10.G221330 | — | O | 10 | 46735180 | 46732478 | 46737883 |
| NS0206252 | 30 | O | 10 | 46749499 | 46749827 | 46749172 |
| Glyma10g38600 | — | O | 10 | 46983790 | 46982907 | 46984673 |
| Glyma10g40520 | — | O | 10 | 48498769 | 48497366 | 48500173 |
| BF631841 | — | O | 10 | 48536884 | 48536690 | 48537079 |
| Glyma10g41460 | — | O | 10 | 49116840 | 49114600 | 49119081 |
| Glyma10g41470 | — | O | 10 | 49123712 | 49121296 | 49126128 |
| TC412490 | — | O | 10 | 49124228 | 49122322 | 49126134 |
| Gm_W82_CR10.G236520 | — | O | 10 | 49715508 | 49712499 | 49718518 |

TABLE 8

Chromosome 10-Marker type and nucleic acid primer and probes useful in the detection of certain alleles of polymorphic nucleic acid markers associated with an iron deficiency growth condition tolerant phenotype.

| Marker or Locus Name | SEQ ID NO | Marker Type | Sequence |
|---|---|---|---|
| NS0120070 | 24 | TAQMAN | — |
| Forward Primer | 31 | — | AATATCCACGGTATGCTGTTTGAAT |
| Reverse Primer | 32 | — | CTCGTTCTAATGGAAAAGCGAATC |
| Vic Probe | 33 | — | CTTGATAGCTGCCATTT |
| Fam Probe | 34 | — | AGCTGTCATTTCTT |
| NS0097952 | 25 | TAQMAN | — |
| Forward Primer | 35 | — | CGAAGCATTACACTATTTTCTGTCAAA |
| Reverse Primer | 36 | — | AAAAAATCACATGATACGAGAAAAGATCT |
| Vic Probe | 37 | — | CAATTGAACCATTTCG |
| Fam Probe | 38 | — | TTGAACCGTTTCGAGC |
| NS0092960 | 26 | TAQMAN | — |
| Forward Primer | 39 | — | CCATTCTGAAGATGAGGCATTG |
| Reverse Primer | 40 | — | ACAAGAGTTTGTAGGAAAACATGATGTT |
| Vic Probe | 41 | — | TCCATTGGGTACTCC |

TABLE 8-continued

Chromosome 10-Marker type and nucleic acid primer and probes useful in the detection of certain alleles of polymorphic nucleic acid markers associated with an iron deficiency growth condition tolerant phenotype.

| Marker or Locus Name | SEQ ID NO | Marker Type | Sequence |
|---|---|---|---|
| Fam Probe | 42 | — | CATTGGGAACTCC |
| NS0118907 | 27 | TAQMAN | — |
| Forward Primer | 43 | — | CCTTTCAAAACCTTTAAGGCATGTA |
| Reverse Primer | 44 | — | GTTCCTAGCCAACAATGAGTTTCTC |
| Vic Probe | 45 | — | AGCTCCAACATATGAT |
| Fam Probe | 46 | — | CTCCAACCTATGATTG |

TABLE 9

Chromosome 7 - QTL on chromosome 7 associated with a low iron growth condition tolerant phenotype.

| Marker or Locus Name | SEQ ID NO | cM Map Position on chromosome seven (7) | Allelic Form(s) Associated With Low Fe Tolerance Phenotype[1] | Allelic Form(s) Not-Associated with Low Fe Tolerance Phenotype[1] | Polymorphic Position | Identified Within Region Associated With Low Fe Tolerance |
|---|---|---|---|---|---|---|
| Gm_W82_CR07.G4950 | — | — | — | — | — | — |
| TC112538 | — | — | — | — | — | — |
| Glyma07g03790 | — | — | — | — | — | — |
| Gm_W82_CR07.G8460 | — | — | — | — | — | — |
| Glyma07g03800 | — | — | — | — | — | — |
| Glyma07g03810 | — | — | — | — | — | — |
| NS0202654 | 47 | 27.6 | TT | GG | 117 | *** |
| NS0206351 | 48 | 27.7 | CC | GG | 131 | *** |
| Glyma07g04470 | — | — | — | — | — | *** |
| Glyma07g04840 | — | — | — | — | — | *** |
| NS0202966 | 49 | 36.2 | TT | GG | 180 | *** |
| Glyma07g05420 | — | — | — | — | — | — |
| Glyma07g05820 | — | — | — | — | — | — |
| NS0102362 | — | — | — | — | — | — |
| Glyma07g06150 | — | — | — | — | — | — |
| Glyma07g06510 | — | — | — | — | — | — |
| Glyma07g06560 | — | — | — | — | — | — |
| Glyma07g07380 | — | — | — | — | — | — |
| Gm_W82_CR07.G30600 | — | — | — | — | — | — |
| Pvcon9217 | — | — | — | — | — | — |
| TC119399 | — | — | — | — | — | — |
| Glyma07g07560 | — | — | — | — | — | — |
| TC385708 | — | — | — | — | — | — |
| Glyma07g08950 | — | — | — | — | — | — |
| Glyma07g09110 | — | — | — | — | — | — |
| Glyma07g09150 | — | — | — | — | — | — |
| Glyma07g09160 | — | — | — | — | — | — |
| Glyma07g09170 | — | — | — | — | — | — |
| Glyma07g09900 | — | — | — | — | — | — |
| Glyma07g09960 | — | — | — | — | — | — |
| Glyma07g09970 | — | — | — | — | — | — |
| NS0119842 | — | — | — | — | — | — |
| TA57919_3847 | — | — | — | — | — | — |
| Glyma07g11180 | — | — | — | — | — | — |
| Glyma07g12210 | — | — | — | — | — | — |
| Glyma07g29640 | — | — | — | — | — | — |
| Glyma07g29650 | — | — | — | — | — | — |
| Glyma07g29940 | — | — | — | — | — | — |
| Glyma07g31380 | — | — | — | — | — | — |
| Glyma07g31390 | — | — | — | — | — | — |
| NS0202730 | 50 | 129.3 | AA | GG | 212 | *** |
| NS0206314 | 51 | 129.5 | CC | TT | 44 | *** |
| Glyma07g31610 | — | — | — | — | — | — |
| Glyma07g32330 | — | — | — | — | — | — |
| Glyma07g33070 | — | — | — | — | — | — |

TABLE 9-continued

Chromosome 7 - QTL on chromosome 7 associated with a low iron growth condition tolerant phenotype.

| Marker or Locus Name | SEQ ID NO | cM Map Position on chromosome seven (7) | Allelic Form(s) Associated With Low Fe Tolerance Phenotype[1] | Allelic Form(s) Not-Associated with Low Fe Tolerance Phenotype[1] | Polymorphic Position | Identified Within Region Associated With Low Fe Tolerance |
|---|---|---|---|---|---|---|
| Glyma07g33090 | — | — | — | — | — | — |
| Glyma07g33560 | — | — | — | — | — | — |

TABLE 10

Chromosome 7 - Physical positions of certain genetic markers on soybean chromosome 7 in proximity to QTL associated with a low iron growth condition tolerant phenotype.

| Marker or Locus Name | SEQ ID NO | LG | Chromsome | Middle Position | Start | Stop |
|---|---|---|---|---|---|---|
| Gm_W82_CR07.G4950 | — | M | 7 | 1583569 | 1582889 | 1584249 |
| TC112538 | — | M | 7 | 2300269 | 2295259 | 2305279 |
| Glyma07g03790 | — | M | 7 | 2612066 | 2611352 | 2612781 |
| Gm_W82_CR07.G8460 | — | M | 7 | 2612066 | 2611352 | 2612781 |
| Glyma07g03800 | — | M | 7 | 2617193 | 2616471 | 2617916 |
| Glyma07g03810 | — | M | 7 | 2625857 | 2624956 | 2626758 |
| NS0202654 | 47 | M | 7 | 2799169 | 2799349 | 2798990 |
| NS0206351 | 48 | M | 7 | 2884070 | 2883889 | 2884252 |
| Glyma07g04470 | — | M | 7 | 3258830 | 3257169 | 3260492 |
| Glyma07g04840 | — | M | 7 | 3566409 | 3565090 | 3567728 |
| NS0202966 | 49 | M | 7 | 3874645 | 3874138 | 3875152 |
| Glyma07g05420 | — | M | 7 | 4097016 | 4095962 | 4098070 |
| Glyma07g05820 | — | M | 7 | 4509739 | 4508711 | 4510768 |
| NS0102362 | — | M | 7 | 4840904 | 4840559 | 4841250 |
| Glyma07g06150 | — | M | 7 | 4868984 | 4867327 | 4870641 |
| Glyma07g06510 | — | M | 7 | 5248237 | 5245895 | 5250579 |
| Glyma07g06560 | — | M | 7 | 5283366 | 5281545 | 5285187 |
| Glyma07g07380 | — | M | 7 | 6062119 | 6060096 | 6064143 |
| Gm_W82_CR07.G30600 | — | M | 7 | 6062119 | 6060096 | 6064143 |
| Pvcon9217 | — | M | 7 | 6063220 | 6062920 | 6063521 |
| TC119399 | — | M | 7 | 6063744 | 6063342 | 6064147 |
| Glyma07g07560 | — | M | 7 | 6267199 | 6266247 | 6268152 |
| TC385708 | — | M | 7 | 6660065 | 6659800 | 6660331 |
| Glyma07g08950 | — | M | 7 | 7481983 | 7480599 | 7483367 |
| Glyma07g09110 | — | M | 7 | 7584736 | 7583460 | 7586013 |
| Glyma07g09150 | — | M | 7 | 7623295 | 7617936 | 7628654 |
| Glyma07g09160 | — | M | 7 | 7634956 | 7632638 | 7637275 |
| Glyma07g09170 | — | M | 7 | 7650900 | 7646391 | 7655409 |
| Glyma07g09900 | — | M | 7 | 8354620 | 8353183 | 8356057 |
| Glyma07g09960 | — | M | 7 | 8379199 | 8377095 | 8381304 |
| Glyma07g09970 | — | M | 7 | 8384620 | 8383415 | 8385825 |
| NS0119842 | — | M | 7 | 8964940 | 8965292 | 8964589 |
| TA57919_3847 | — | M | 7 | 9404069 | 9399907 | 9408231 |
| Glyma07g11180 | — | M | 7 | 9406330 | 9399842 | 9412818 |
| Glyma07g12210 | — | M | 7 | 10528875 | 10527516 | 10530235 |
| Glyma07g29640 | — | M | 7 | 34637242 | 34635418 | 34639067 |
| Glyma07g29650 | — | M | 7 | 34646347 | 34640449 | 34652245 |
| Glyma07g29940 | — | M | 7 | 35026011 | 35025068 | 35026954 |
| Glyma07g31380 | — | M | 7 | 36403003 | 36400692 | 36405314 |
| Glyma07g31390 | — | M | 7 | 36408650 | 36407590 | 36409711 |
| NS0202730 | 50 | M | 7 | 36497284 | 36497794 | 36496774 |
| NS0206314 | 51 | M | 7 | 36529671 | 36529465 | 36529877 |
| Glyma07g31610 | — | M | 7 | 36591219 | 36590751 | 36591687 |
| Glyma07g32330 | — | M | 7 | 37262246 | 37261063 | 37263430 |
| Glyma07g33070 | — | M | 7 | 37970359 | 37969519 | 37971200 |
| Glyma07g33090 | — | M | 7 | 37977896 | 37976947 | 37978845 |
| Glyma07g33560 | — | M | 7 | 38479141 | 38477620 | 38480663 |

Provided herein is a QTL on chromosome 3—that is flanked by loci Glyma03g34510 and Glyma03g42250—that is associated with a low iron growth condition tolerant phenotype. Sub-regions of chromosome 3 that flank a QTL associated with a low iron growth condition tolerant phenotype include, but are not limited to sub-regions defined by any of the following sets of loci:

a) loci Glyma03g34510 and Glyma03g41830;
b) loci Gm_W82_CR03.G378360 and Glyma03g42250;
c) loci Gm_W82_CR03.G378360 and Glyma03g41830;
d) loci Glyma03g34760 and Glyma03g42250;

e) loci Glyma03g34760 and Glyma03g41830;
f) loci Glyma03g34860 and Glyma03g42250; or
g) loci Glyma03g34860 and Glyma03g41830.
(Table 1).

These loci flank a genomic interval that spans telomere proximal nucleotide 41914204 to centromere proximal nucleotide 47499828 in the physical map of linkage group N provided in the Table 2. Polymorphic nucleic acid markers located in this genomic interval that are associated with a low iron growth condition tolerant phenotype include, but are not limited to: NS0202712 (SEQ ID NO: 1); NS0129403 (SEQ ID NO: 2); NS0115624 (SEQ ID NO: 3); NS0202842 (SEQ ID NO: 4); NS0122122 (SEQ ID NO: 5); NS0205984 (SEQ ID NO: 6); and NS0202698 (SEQ ID NO: 7).

In certain embodiments of the invention, it is useful to detect in, or determine, whether a soybean plant has an allelic state that is associated with a low iron growth condition tolerant phenotype (Table 1). Certain non-limiting exemplary examples include identifying a soybean plant that has any one or more of: the AA allelic state of the polymorphic nucleic acid of NS0202712 (SEQ ID NO: 1); the GG allelic state of NS0129403 (SEQ ID NO: 2); the TT allelic state of NS0115624 (SEQ ID NO: 3); the CC allelic state of NS0202842 (SEQ ID NO: 4); the CC allelic state of NS0122122 (SEQ ID NO: 5); the GG allelic state of NS0205984 (SEQ ID NO: 6); or the GG NS0202698 (SEQ ID NO: 7). In certain preferred embodiments, a soybean plant is identified having the CC allelic state of NS0202842 (SEQ ID NO: 4). One of skill in the art will also recognize that it can be useful to identify at a genetic locus a polymorphic nucleic acid marker that is not associated with a low iron growth condition tolerant phenotype (Table 1) in a plant or germplasm, such as when introgressing a QTL associated with a low iron growth tolerant phenotype into a genetic background not associated with such a phenotype.

Provided herein is a QTL on chromosome 19—that is flanked by loci Glyma19g32880 and Contig9146—that is associated with a low iron growth condition tolerant phenotype. Sub-regions of chromosome 19 that flank a QTL associated with a low iron growth condition tolerant phenotype include, but are not limited to sub-regions defined by any of the following sets of loci:
  a) loci Glyma19g32880 and Gm_W82_CR19.G249630;
  b) loci Glyma19g32880 and Glyma19g34750;
  c) loci Glyma19g32880 and BARCSOYSSR_19_1192;
  d) loci Glyma19g32880 and Contig13742;
  e) loci Glyma19g32880 and 220298_3433_1666;
  f) loci Glyma19g32880 and NGMAX005710149;
  g) loci Glyma19g32880 and Glyma19g34740;
  h) loci Glyma19g32880 and Gm_W82_CR19.G249620;
  i) loci Glyma19g33540 and Contig9146;
  j) loci Glyma19g33540 and Gm_W82_CR19.G249630;
  k) loci Glyma19g33540 and Glyma19g34750;
  l) loci Glyma19g33540 and BARCSOYSSR_19_1192;
  m) loci Glyma19g33540 and Contig13742;
  n) loci Glyma19g33540 and 220298_3433_1666;
  o) loci Glyma19g33540 and NGMAX005710149;
  p) loci Glyma19g33540 and Glyma19g34740; or
  q) loci Glyma19g33540 and Gm_W82_CR19.G249620.
(Table 4).

These loci flank a genomic interval that spans telomere proximal nucleotide 40562661 to centromere proximal nucleotide 42351748 in the physical map of linkage group L provided in the Table 5. Polymorphic nucleic acid markers located in this genomic interval that are associated with a low iron growth condition tolerant phenotype can be detected with polymorphic nucleic acid markers that include, but are not limited to: NS0206298_(SEQ ID NO: 20); NS0205620 (SEQ ID NO: 21); NS0206055 (SEQ ID NO: 22); and NS0204985 (SEQ ID NO: 23).

In certain embodiments of the invention, it is useful to detect in, or determine, whether a soybean plant has an allelic state that is associated with a low iron growth condition tolerant phenotype (Table 4). Certain non-limiting exemplary examples include identifying a soybean plant that has any one or more of: the AA allelic state of the polymorphic nucleic acid of NS0206298_(SEQ ID NO: 20); the GG allelic state of NS0205620 (SEQ ID NO: 21); the AA allelic state of NS0206055 (SEQ ID NO: 22); or the CC allelic state of NS0204985 (SEQ ID NO: 23). In certain preferred embodiments, a soybean plant is identified having the AA allelic state of NS0206055 (SEQ ID NO: 22). One of skill in the art will also recognize that it can be useful to identify at a genetic locus a polymorphic nucleic acid marker that is not associated with a low iron growth condition tolerant phenotype (Table 4) in a plant or germplasm, such as when introgressing a QTL associated with a low iron growth tolerant phenotype into a genetic background not associated with such a phenotype.

Provided herein is a genomic interval on chromosome 10 spanning two QTL—that is flanked by loci NS0116559 and Gm_W82_CR10.G236520—that is associated with a low iron growth condition tolerant phenotype. Sub-regions of chromosome 10 that flank QTL associated with a low iron growth condition tolerant phenotype include, but are not limited to sub-regions defined by any of the following sets of loci:
  a) loci NS0116559 and TC412490;
  b) loci NS0116559 and Glyma10g41470;
  c) loci NS0116559 and Glyma10g41460;
  d) loci NS0116559 and BF631841;
  e) loci NS0116559 and Glyma10g40520;
  f) loci NS0116559 and Glyma10g38600;
  g) loci Glyma10g33710 and Gm_W82_CR10.G236520;
  h) loci Glyma10g33710 and TC412490;
  i) loci Glyma10g33710 and Glyma10g41470;
  j) loci Glyma10g33710 and Glyma10g41460;
  k) loci Glyma10g33710 and BF631841;
  l) loci Glyma10g33710 and Glyma10g40520;
  m) loci Glyma10g33710 and Glyma10g38600;
  n) loci TA42233_3847 and Gm_W82_CR10.G236520;
  o) loci TA42233_3847 and TC412490;
  p) loci TA42233_3847 and Glyma10g41470;
  q) loci TA42233_3847 and Glyma10g41460;
  r) loci TA42233_3847 and BF631841;
  s) loci TA42233_3847 and Glyma10g40520;
  t) loci TA42233_3847 and Glyma10g38600;
  u) loci AF108084.1 and Gm_W82_CR10.G236520;
  v) loci AF108084.1 and TC412490;
  w) loci AF108084.1 and Glyma10g41470;
  x) loci AF108084.1 and Glyma10g41460;
  y) loci AF108084.1 and BF631841;
  z) loci AF108084.1 and Glyma10g40520;
  aa) loci AF108084.1 and Glyma10g38600;
  bb) loci AW734581 and Gm_W82_CR10.G236520;
  cc) loci AW734581 and TC412490;
  dd) loci AW734581 and Glyma10g41470;
  ee) loci AW734581 and Glyma10g41460;
  ff) loci AW734581 and BF631841;
  gg) loci AW734581 and Glyma10g40520;
  hh) loci AW734581 and Glyma10g38600;
  ii) loci Glyma10g34260 and Gm_W82_CR10.G236520;
  jj) loci Glyma10g34260 and TC412490;
  kk) loci Glyma10g34260 and Glyma10g41470;

ll) loci Glyma10g34260 and Glyma10g41460;
mm) loci Glyma10g34260 and BF631841;
nn) loci Glyma10g34260 and Glyma10g40520;
oo) loci Glyma10g34260 and Glyma10g38600;
pp) loci Glyma10g34280 and Gm_W82_CR10.G236520;
qq) loci Glyma10g34280 and TC412490;
rr) loci Glyma10g34280 and Glyma10g41470;
ss) loci Glyma10g34280 and Glyma10g41460;
tt) loci Glyma10g34280 and BF631841;
uu) loci Glyma10g34280 and Glyma10g40520;
vv) loci Glyma10g34280 and Glyma10g38600;
ww) loci Glyma10g34290 and Gm_W82_CR10.G236520;
xx) loci Glyma10g34290 and TC412490;
yy) loci Glyma10g34290 and Glyma10g41470;
zz) loci Glyma10g34290 and Glyma10g41460;
aaa) loci Glyma10g34290 and BF631841;
bbb) loci Glyma10g34290 and Glyma10g40520;
ccc) loci Glyma10g34290 and Glyma10g38600;
ddd) loci Glyma10g34460 and Gm_W82_CR10.G236520;
eee) loci Glyma10g34460 and TC412490;
fff) loci Glyma10g34460 and Glyma10g41470;
ggg) loci Glyma10g34460 and Glyma10g41460;
hhh) loci Glyma10g34460 and BF631841;
iii) loci Glyma10g34460 and Glyma10g40520;
jjj) loci Glyma10g34460 and Glyma10g38600;
kkk) loci Glyma10g34600 and Gm_W82_CR10.G236520;
lll) loci Glyma10g34600 and TC412490;
mmm) loci Glyma10g34600 and Glyma10g41470;
nnn) loci Glyma10g34600 and Glyma10g41460;
ooo) loci Glyma10g34600 and BF631841;
ppp) loci Glyma10g34600 and Glyma10g40520;
qqq) loci Glyma10g34600 and Glyma10g38600;
rrr) loci Glyma10g34630 and Gm_W82_CR10.G236520;
sss) loci Glyma10g34630 and TC412490;
ttt) loci Glyma10g34630 and Glyma10g41470;
uuu) loci Glyma10g34630 and Glyma10g41460;
vvv) loci Glyma10g34630 and BF631841;
www) loci Glyma10g34630 and Glyma10g40520;
xxx) loci Glyma10g34630 and Glyma10g38600;
yyy) loci Glyma10g34850 and Gm_W82_CR10.G236520;
zzz) loci Glyma10g34850 and TC412490;
aaaa) loci Glyma10g34850 and Glyma10g41470;
bbbb) loci Glyma10g34850 and Glyma10g41460;
cccc) loci Glyma10g34850 and BF631841;
dddd) loci Glyma10g34850 and Glyma10g40520; or
eeee) loci Glyma10g34850 and Glyma10g38600.
(Table 6).

These loci flank a genomic interval that spans telomere proximal nucleotide 42075167 to centromere proximal nucleotide 49718518 in the physical map of linkage group O provided in the Table 7. Polymorphic nucleic acid markers located in this genomic interval that are associated with a low iron growth condition tolerant phenotype can be detected with polymorphic nucleic acid markers that include, but are not limited to: NS0120070 (SEQ ID NO: 24); NS0097952 (SEQ ID NO: 25); NS0092960 (SEQ ID NO: 26); NS0118907 (SEQ ID NO: 27); NS0204740 (SEQ ID NO: 28); NS0205036 (SEQ ID NO: 29); and NS0206252 (SEQ ID NO: 30).

In certain embodiments of the invention, it is useful to detect in, or determine whether, a soybean plant has an allelic state that is associated with a low iron growth condition tolerant phenotype (Table 6). Certain non-limiting exemplary examples include identifying a soybean plant that has any one or more of: the TT allelic state of the polymorphic nucleic acid of NS0120070 (SEQ ID NO: 24); the GG allelic state of NS0097952 (SEQ ID NO: 25); the TT allelic state of NS0092960 (SEQ ID NO: 26); the AA allelic state of NS0118907 (SEQ ID NO: 27); the AA allelic state of NS0204740 (SEQ ID NO: 28); the AA allelic state of NS0205036 (SEQ ID NO: 29); or the CC allelic state of NS0206252 (SEQ ID NO: 30). In certain preferred embodiments, a soybean plant is identified having the TT allelic state of NS0092960 (SEQ ID NO: 26). One of skill in the art will also recognize that it can be useful to identify at a genetic locus a polymorphic nucleic acid marker that is not associated with a low iron growth condition tolerant phenotype (Table 6) in a plant or germplasm, such as when introgressing a QTL associated with a low iron growth tolerant phenotype into a genetic background not associated with such a phenotype.

Provided herein is a first QTL on chromosome 10—that is flanked by loci NS0116559 and TA68568_3847—that is associated with a low iron growth condition tolerant phenotype. Sub-regions of chromosome 10 that flank this first QTL associated with a low iron growth condition tolerant phenotype include, but are not limited to sub-regions defined by any of the following sets of loci:
a) loci NS0116559 and BG511181;
b) loci NS0116559 and Glyma10g37610;
c) loci NS0116559 and CV528982;
d) loci NS0116559 and TC130824;
e) loci NS0116559 and BW595896;
f) loci NS0116559 and Glyma10g37600;
g) loci NS0116559 and TC354083;
h) loci NS0116559 and Glyma10g37560;
i) loci Glyma10g33710 and TA68568_3847;
j) loci Glyma10g33710 and BG511181;
k) loci Glyma10g33710 and Glyma10g37610;
l) loci Glyma10g33710 and CV528982;
m) loci Glyma10g33710 and TC130824;
n) loci Glyma10g33710 and BW595896;
o) loci Glyma10g33710 and Glyma10g37600;
p) loci Glyma10g33710 and TC354083;
q) loci Glyma10g33710 and Glyma10g37560;
r) loci TA42233_3847 and TA68568_3847;
s) loci TA42233_3847 and BG511181;
t) loci TA42233_3847 and Glyma10g37610;
u) loci TA42233_3847 and CV528982;
v) loci TA42233_3847 and TC130824;
w) loci TA42233_3847 and BW595896;
x) loci TA42233_3847 and Glyma10g37600;
y) loci TA42233_3847 and TC354083;
z) loci TA42233_3847 and Glyma10g37560;
aa) loci AF108084.1 and TA68568_3847;
bb) loci AF108084.1 and BG511181;
cc) loci AF108084.1 and Glyma10g37610;
dd) loci AF108084.1 and CV528982;
ee) loci AF108084.1 and TC130824;
ff) loci AF108084.1 and BW595896;
gg) loci AF108084.1 and Glyma10g37600;
hh) loci AF108084.1 and TC354083;
ii) loci AF108084.1 and Glyma10g37560;
jj) loci AW734581 and TA68568_3847;
kk) loci AW734581 and BG511181;
ll) loci AW734581 and Glyma10g37610;
mm) loci AW734581 and CV528982;
nn) loci AW734581 and TC130824;
oo) loci AW734581 and BW595896;
pp) loci AW734581 and Glyma10g37600;

qq) loci AW734581 and TC354083;
rr) loci AW734581 and Glyma10g37560;
ss) loci Glyma10g34260 and TA68568_3847;
tt) loci Glyma10g34260 and BG511181;
uu) loci Glyma10g34260 and Glyma10g37610;
vv) loci Glyma10g34260 and CV528982;
ww) loci Glyma10g34260 and TC130824;
xx) loci Glyma10g34260 and BW595896;
yy) loci Glyma10g34260 and Glyma10g37600;
zz) loci Glyma10g34260 and TC354083;
aaa) loci Glyma10g34260 and Glyma10g37560;
bbb) loci Glyma10g34280 and TA68568_3847;
ccc) loci Glyma10g34280 and BG511181;
ddd) loci Glyma10g34280 and Glyma10g37610;
eee) loci Glyma10g34280 and CV528982;
fff) loci Glyma10g34280 and TC130824;
ggg) loci Glyma10g34280 and BW595896;
hhh) loci Glyma10g34280 and Glyma10g37600;
iii) loci Glyma10g34280 and TC354083;
jjj) loci Glyma10g34280 and Glyma10g37560;
kkk) loci Glyma10g34290 and TA68568_3847;
lll) loci Glyma10g34290 and BG511181;
mmm) loci Glyma10g34290 and Glyma10g37610;
nnn) loci Glyma10g34290 and CV528982;
ooo) loci Glyma10g34290 and TC130824;
ppp) loci Glyma10g34290 and BW595896;
qqq) loci Glyma10g34290 and Glyma10g37600;
rrr) loci Glyma10g34290 and TC354083;
sss) loci Glyma10g34290 and Glyma1437560;
ttt) loci Glyma10g34460 and TA68568_3847;
uuu) loci Glyma10g34460 and BG511181;
vvv) loci Glyma10g34460 and Glyma10g37610;
www) loci Glyma10g34460 and CV528982;
xxx) loci Glyma10g34460 and TC130824;
yyy) loci Glyma10g34460 and BW595896;
zzz) loci Glyma10g34460 and Glyma10g37600;
aaaa) loci Glyma10g34460 and TC354083;
bbbb) loci Glyma10g34460 and Glyma10g37560;
cccc) loci Glyma10g34600 and TA68568_3847;
dddd) loci Glyma10g34600 and BG511181;
eeee) loci Glyma10g34600 and Glyma10g37610;
ffff) loci Glyma10g34600 and CV528982;
gggg) loci Glyma10g34600 and TC130824;
hhhh) loci Glyma10g34600 and BW595896;
iiii) loci Glyma10g34600 and Glyma10g37600;
jjjj) loci Glyma10g34600 and TC354083;
kkkk) loci Glyma10g34600 and Glyma10g37560;
llll) loci Glyma10g34630 and TA68568_3847;
mmmm) loci Glyma10g34630 and BG511181;
nnnn) loci Glyma10g34630 and Glyma10g37610;
oooo) loci Glyma10g34630 and CV528982;
pppp) loci Glyma10g34630 and TC130824;
qqqq) loci Glyma10g34630 and BW595896;
rrrr) loci Glyma10g34630 and Glyma10g37600;
ssss) loci Glyma10g34630 and TC354083;
tttt) loci Glyma10g34630 and Glyma10g37560;
uuuu) loci Glyma10g34850 and TA68568_3847;
vvvv) loci Glyma10g34850 and BG511181;
wwww) loci Glyma10g34850 and Glyma10g37610;
xxxx) loci Glyma10g34850 and CV528982;
yyyy) loci Glyma10g34850 and TC130824;
zzzz) loci Glyma10g34850 and BW595896;
aaaaa) loci Glyma10g34850 and Glyma10g37600;
bbbbb) loci Glyma10g34850 and TC354083; or
ccccc) loci Glyma10g34850 and Glyma10g37560.
(Table 6).

These loci flank a genomic interval that spans telomere proximal nucleotide 42075167 to centromere proximal nucleotide 46157806 in the physical map of linkage group O provided in the Table 7. Polymorphic nucleic acid markers located in this genomic interval that are associated with a low iron growth condition tolerant phenotype can be detected with polymorphic nucleic acid markers that include, but are not limited to: NS0120070 (SEQ ID NO: 24); NS0097952 (SEQ ID NO: 25); NS0092960 (SEQ ID NO: 26); and NS0118907 (SEQ ID NO: 27).

Provided herein is a second QTL on chromosome 10—that is flanked by loci Glyma10g37560 and Gm_W82_CR10.G236520—that is associated with a low iron growth condition tolerant phenotype. Sub-regions of chromosome 10 that flank this second QTL associated with a low iron growth condition tolerant phenotype include, but are not limited to sub-regions defined by any of the following sets of loci:
a) loci Glyma10g37560 and TC412490;
b) loci Glyma10g37560 and Glyma10g41470;
c) loci Glyma10g37560 and Glyma10g41460;
d) loci Glyma10g37560 and BF631841;
e) loci Glyma10g37560 and Glyma10g40520;
f) loci Glyma10g37560 and Glyma10g38600;
g) loci TC354083 and Gm_W82_CR10.G236520
h) loci TC354083 and TC412490;
i) loci TC354083 and Glyma10g41470;
j) loci TC354083 and Glyma10g41460;
k) loci TC354083 and BF631841;
l) loci TC354083 and Glyma10g40520;
m) loci TC354083 and Glyma10g38600;
n) loci Glyma10g37600 and Gm_W82_CR10.G236520
o) loci Glyma10g37600 and TC412490;
p) loci Glyma10g37600 and Glyma10g41470;
q) loci Glyma10g37600 and Glyma10g41460;
r) loci Glyma10g37600 and BF631841;
s) loci Glyma10g37600 and Glyma10g40520;
t) loci Glyma10g37600 and Glyma10g38600;
u) loci BW595896 and Gm_W82_CR10.G236520
v) loci BW595896 and TC412490;
w) loci BW595896 and Glyma10g41470;
x) loci BW595896 and Glyma10g41460;
y) loci BW595896 and BF631841;
z) loci BW595896 and Glyma10g40520;
aa) loci BW595896 and Glyma10g38600;
bb) loci TC130824 and Gm_W82_CR10.G236520
cc) loci TC130824 and TC412490;
dd) loci TC130824 and Glyma10g41470;
ee) loci TC130824 and Glyma10g41460;
ff) loci TC130824 and BF631841;
gg) loci TC130824 and Glyma10g40520;
hh) loci TC130824 and Glyma10g38600;
ii) loci CV528982 and Gm_W82_CR10.G236520
jj) loci CV528982 and TC412490;
kk) loci CV528982 and Glyma10g41470;
ll) loci CV528982 and Glyma10g41460;
mm) loci CV528982 and BF631841;
nn) loci CV528982 and Glyma10g40520;
oo) loci CV528982 and Glyma10g38600;
pp) loci Glyma10g37610 and Gm_W82_CR10.G236520
qq) loci Glyma10g37610 and TC412490;
rr) loci Glyma10g37610 and Glyma10g41470;
ss) loci Glyma10g37610 and Glyma10g41460;
tt) loci Glyma10g37610 and BF631841;

uu) loci Glyma10g37610 and Glyma10g40520;
vv) loci Glyma10g37610 and Glyma10g38600;
ww) loci BG511181 and Gm_W82_CR10.G236520
xx) loci BG511181 and TC412490;
yy) loci BG511181 and Glyma10g41470;
zz) loci BG511181 and Glyma10g41460;
aaa) loci BG511181 and BF631841;
bbb) loci BG511181 and Glyma10g40520;
ccc) loci BG511181 and Glyma10g38600;
ddd) loci TA68568_3847 and Gm_W82_CR10.G236520
ccc) loci TA68568_3847 and TC412490;
ddd) loci TA68568_3847 and Glyma10g41470;
eee) loci TA68568_3847 and Glyma10g41460;
fff) loci TA68568_3847 and BF631841;
ggg) loci TA68568_3847 and Glyma10g40520; or
hhh) loci TA68568_3847 and Glyma10g38600.
(Table 6).

These loci flank a genomic interval that spans telomere proximal nucleotide 46112579 to centromere proximal nucleotide 49718518 in the physical map of linkage group O provided in the Table 7. Polymorphic nucleic acid markers located in this genomic interval that are associated with a low iron growth condition tolerant phenotype can be detected with polymorphic nucleic acid markers that include, but are not limited to: NS0204740 (SEQ ID NO: 28); NS0205036 (SEQ ID NO:29); and NS0206252 (SEQ ID NO: 30).

Provided herein is a genomic interval on chromosome 7 spanning two QTL—that is flanked by loci Gm_W82_CR07.G4950 and Glyma07g33560—that is associated with a low iron growth condition tolerant phenotype. Sub-regions of chromosome 7 that flank QTL associated with a low iron growth condition tolerant phenotype include, but are not limited to sub-regions defined by any of the following sets of loci:
  a) loci Gm_W82_CR07.G4950 and any of loci: Glyma07g33090, Glyma07g33070, Glyma07g32330, or Glyma07g31610;
  b) loci TC112538 and any of loci: Glyma07g33560, Glyma07g33090, Glyma07g33070, Glyma07g32330, or Glyma07g31610;
  c) loci Glyma07g03790 and any of loci: Glyma07g33560, Glyma07g33090, Glyma07g33070, Glyma07g32330, or Glyma07g31610;
  d) loci Gm_W82_CR07.08460 and any of loci: Glyma07g33560, Glyma07g33090, Glyma07g33070, Glyma07g32330, or Glyma07g31610;
  e) loci Glyma07g03800 and any of loci: Glyma07g33560, Glyma07g33090, Glyma07g33070, Glyma07g32330, or Glyma07g31610; or
  f) loci Glyma07g03810 and any of loci: Glyma07g33560, Glyma07g33090, Glyma07g33070, Glyma07g32330, or Glyma07g31610.
(Table 9).

These loci flank a genomic interval that spans telomere proximal nucleotide 1582889 to centromere proximal nucleotide 38480663 in the physical map of linkage group M provided in the Table 10. Polymorphic nucleic acid markers located in this genomic interval that are associated with a low iron growth condition tolerant phenotype can be detected with polymorphic nucleic acid markers that include, but are not limited to: NS0202654 (SEQ ID NO: 47), NS0206351 (SEQ ID NO: 48), NS0202966 (SEQ ID NO: 49), NS0202730 (SEQ ID NO: 50), and NS0206314 (SEQ ID NO: 51).

In certain embodiments of the invention, it is useful to detect in, or determine whether, a soybean plant has an allelic state that is associated with a low iron growth condition tolerant phenotype (Table 9). Certain non-limiting exemplary examples include identifying a soybean plant that has any one or more of: the TT allelic state of the polymorphic nucleic acid of NS0202654 (SEQ ID NO: 47), the CC allelic state of NS0206351 (SEQ ID NO: 48), the TT allelic state of NS0202966 (SEQ ID NO: 49), the AA allelic state of NS0202730 (SEQ ID NO: 50), and the CC allelic state of NS0206314 (SEQ ID NO: 51). In certain preferred embodiments, a soybean plant is identified having the AA allelic state of NS0202730 (SEQ ID NO: 50). One of skill in the art will also recognize that it can be useful to identify at a genetic locus a polymorphic nucleic acid marker that is not associated with a low iron growth condition tolerant phenotype (Table 9) in a plant or germplasm, such as when introgressing a QTL associated with a low iron growth tolerant phenotype into a genetic background not associated with such a phenotype.

Provided herein is a first QTL on chromosome 7—that is flanked by loci Gm_W82_CR07.G4950 and Glyma07g12210—that is associated with a low iron growth condition tolerant phenotype. Sub-regions of chromosome 7 that flank this first QTL associated with a low iron growth condition tolerant phenotype include, but are not limited to sub-regions defined by any of the following sets of loci:
  a) loci Gm_W82_CR07.G4950 and any of loci: Glyma07g11180, TA57919_3847, NS0119842, Glyma07g09970, Glyma07g09960, Glyma07g09900, Glyma07g09170, Glyma07g09160, Glyma07g09150, Glyma07g09110, Glyma07g08950, TC385708, Glyma07g07560, TC119399, Pvcon9217, Gm_W82_CR07.G30600, Glyma07g07380, Glyma07g06560, Glyma07g06510, Glyma07g06150, NS0102362, Glyma07g05820, and Glyma07g05420;
  b) loci TC112538 and any of loci: Glyma07g12210, Glyma07g11180, TA57919_3847, NS0119842, Glyma07g09970, Glyma07g09960, Glyma07g09900, Glyma07g09170, Glyma07g09160, Glyma07g09150, Glyma07g09110, Glyma07g08950, TC385708, Glyma07g07560, TC119399, Pvcon9217, Gm_W82_CR07.G30600, Glyma07g07380, Glyma07g06560, Glyma07g06510, Glyma07g06150, NS0102362, Glyma07g05820, and Glyma07g05420;
  c) loci Glyma07g03790 and any of loci: Glyma07g12210, Glyma07g11180, TA57919_3847, NS0119842, Glyma07g09970, Glyma07g09960, Glyma07g09900, Glyma07g09170, Glyma07g09160, Glyma07g09150, Glyma07g09110, Glyma07g08950, TC385708, Glyma07g07560, TC119399, Pvcon9217, Gm_W82_CR07.G30600, Glyma07g07380, Glyma07g06560, Glyma07g06510, Glyma07g06150, NS0102362, Glyma07g05820, and Glyma07g05420;
  d) loci Gm_W82_CR07.G8460 and any of loci: Glyma07g12210, Glyma07g11180, TA57919_3847, NS0119842, Glyma07g09970, Glyma07g09960, Glyma07g09900, Glyma07g09170, Glyma07g09160, Glyma07g09150, Glyma07g09110, Glyma07g08950, TC385708, Glyma07g07560, TC119399, Pvcon9217, Gm_W82_CR07.G30600, Glyma07g07380, Glyma07g06560, Glyma07g06510, Glyma07g06150, NS0102362, Glyma07g05820, and Glyma07g05420;
  e) Glyma07g03800 and any of loci: Glyma07g12210, Glyma07g11180, TA57919_3847, NS0119842, Glyma07g09970, Glyma07g09960, Glyma07g09900, Glyma07g09170, Glyma07g09160, Glyma07g09150, Glyma07g09110, Glyma07g08950, TC385708, Glyma07g07560, TC119399, Pvcon9217, Gm_W82_CR07.G30600, Glyma07g07380, Glyma07g06560, Glyma07g06510, Glyma07g06150, NS0102362, Glyma07g05820, and Glyma07g05420; and f) Glyma07g03810 and any of loci: Glyma07g12210, Glyma07g11180, TA57919_3847, NS0119842, Glyma07g09970, Glyma07g09960, Glyma07g09900, Glyma07g09170, Glyma07g09160, Glyma07g09150, Glyma07g09110, Glyma07g08950, TC385708, Glyma07g07560, TC119399, Pvcon9217, Gm_W82_CR07.G30600, Glyma07g07380, Glyma07g06560, Glyma07g06510, Glyma07g06150, NS0102362, Glyma07g05820, and Glyma07g05420.

(Table 9).

These loci flank a genomic interval that spans telomere proximal nucleotide 1582889 to centromere proximal nucleotide 10530235 in the physical map of linkage group M provided in the Table 10. Polymorphic nucleic acid markers located in this genomic interval that are associated with a low iron growth condition tolerant phenotype can be detected with polymorphic nucleic acid markers that include, but are not limited to: NS00202654 (SEQ ID NO: 47); NS0206351 (SEQ ID NO: 48); and NS0202966 (SEQ ID NO: 49).

Provided herein is a second QTL on chromosome 7—that is flanked by loci Glyma07g29640 and Glyma07g33560—that is associated with a low iron growth condition tolerant phenotype. Sub-regions of chromosome 7 that flank this second QTL associated with a low iron growth condition tolerant phenotype include, but are not limited to sub-regions defined by any of the following sets of loci:

a) loci Glyma07g29640 and any of loci: Glyma07g33090, Glyma07g33070, Glyma07g32330, and Glyma07g31610;

b) loci Glyma07g29650 and any of loci: Glyma07g33560, Glyma07g33090, Glyma07g33070, Glyma07g32330, and Glyma07g31610;

c) loci Glyma07g29940 and any of loci: Glyma07g33560, Glyma07g33090, Glyma07g33070, Glyma07g32330, and Glyma07g31610;

d) loci Glyma07g31380 and any of loci: Glyma07g33560, Glyma07g33090, Glyma07g33070, Glyma07g32330, and Glyma07g31610; or e) loci Glyma07g31390 and any of loci: Glyma07g33560, Glyma07g33090, Glyma07g33070, Glyma07g32330, and Glyma07g31610.

(Table 9).

These loci flank a genomic interval that spans telomere proximal nucleotide 34635418 to centromere proximal nucleotide 38480663 in the physical map of linkage group M provided in the Table 10. Polymorphic nucleic acid markers located in this genomic interval that are associated with a low iron growth condition tolerant phenotype can be detected with polymorphic nucleic acid markers that include, but are not limited to: NS0202730 (SEQ ID NO: 50) and NS0206314 (SEQ ID NO: 51).

Further provided herewith are certain other QTL that have also been identified as associated with a desirable phenotype of tolerance to growth in low iron conditions when present in certain allelic forms.

These several soybean QTL provided—that can be associated with a desirable low iron growth condition tolerant phenotype when present in certain allelic forms—are located on soybean chromosome 18 (soybean linkage group G), soybean chromosome 5 (soybean linkage group A1), soybean chromosome 7 (soybean linkage group M), soybean chromosome 17 (soybean linkage group D2), soybean chromosome 19 (soybean linkage group L), and soybean chromosome 9 (soybean linkage group K).

A series of public and other markers useful in practicing the methods of this invention are provided herewith in Tables 14-31. Nucleic acid sequences for certain non-public markers useful in the practice of the invention are provided herewith in the accompanying sequence listing, which is incorporated herein by reference in its entirety.

Tables 15, 18, 21, 24, 27, and 30 (corresponding to chromosomes 18, 5, 7, 17, 19, and 9, respectively) shows the relative positions of certain markers that have been disclosed in public databases and non-public (bolded) polymorphic nucleic acid markers, designated SEQ ID NOs, genetic positions (cM) on the chromosome, the allelic forms of certain polymorphic nucleic acid markers associated with a low iron growth condition tolerant phenotype, the allelic forms of those polymorphic nucleic acid markers not associated with the low iron growth condition tolerant phenotype, and the polymorphic position within the sequence of the polymorphic nucleic acid marker. The bolded markers have been identified as within a genomic region associated with a low iron growth condition tolerant phenotype.

Tables 16, 19, 22, 25, 28 and 31 (corresponding to chromosomes 18, 5, 7, 17, 19, and 9, respectively) provides for each polymorphic nucleic acid marker/SEQ ID NO the linkage group corresponding to the chromosome and the relative physical map positions of the markers.

Tables 32, 33, and 34 (corresponding to chromosomes 18, 7 and 9, respectively) provide for certain polymorphic nucleic acid markers, the type of marker, and primer and probe sequences useful in detecting such markers.

Tables 14, 17, 20, 23, 26, and 29 of the Appendix to the Specification, which is incorporated herein by reference in its entirety, discloses the sources of certain of the markers contained in Tables 15, 16, 18, 19, 21, 22, 24, 25, 27, 28, 30, 31, and 32-34.

TABLE 15

Chromosome 18 - QTL on chromosome 18 associated with a low iron growth condition tolerant phenotype.

| Marker or Locus Name | SEQ ID NO: | cM Map Position on chromosome eighteen (18) | [-LOG10(P)] | Allelic Form(s) Associated With Low Fe Tolerance Phenotype[1] | Allelic Form(s) Not-Associated with Low Fe Tolerance Phenotype[1] | Polymorphic Position |
|---|---|---|---|---|---|---|
| FE898349 | — | — | — | — | — | — |
| TC126194 | — | — | — | — | — | — |
| Glyma18g50900 | — | — | — | — | — | — |
| Gm_W82_CR18.G397200 | — | — | — | — | — | — |
| NGMAX008183850 | 52 | 155.1 | 2.1 | CC | TT | 201 |
| NGMAX008184740 | 53 | 155.8 | 2.1 | GG | AA | 201 |

TABLE 15-continued

Chromosome 18 - QTL on chromosome 18 associated with a low iron growth condition tolerant phenotype.

| Marker or Locus Name | SEQ ID NO: | cM Map Position on chromosome eighteen (18) | [-LOG10(P)] | Allelic Form(s) Associated With Low Fe Tolerance Phenotype[1] | Allelic Form(s) Not-Associated with Low Fe Tolerance Phenotype[1] | Polymorphic Position |
|---|---|---|---|---|---|---|
| NS0204945 | 54 | | 3.6 | GG | AA | 378 |
| NGMAX008190659 | 55 | 159.5 | 2.5 | TT | AA | 201 |
| NGMAX008190985 | 56 | 159.6 | 2.1 | AA | TT | 201 |
| NS0205638 | 57 | 159.9 | 2.8 | GG | CC | 326 |
| NGMAX008191317 | 58 | 159.9 | 2.7 | TT | CC | 201 |
| NS0092671 | 59 | 160 | 2.3 | TT | CC | 170 |
| NS0118292 | 60 | 160 | 2.5 | CC | AA | 367 |
| NGMAX008194551 | 61 | 161.8 | 2.4 | TT | GG | 201 |
| NGMAX008194952 | 62 | 162.5 | 2.3 | TT | CC | 201 |
| 108285_2293_0177 | — | — | — | — | — | — |
| Cf17723d | — | — | — | — | — | — |
| Cf14688d | — | — | — | — | — | — |

TABLE 16

Chromosome 18 - Physical positions of certain genetic markers on soybean chromosome 18 in proximity to QTL associated with a low iron growth condition tolerant phenotype.

| Marker or Locus Name | SEQ ID NO: | Linkage Group | Chromosome | Middle Position | Start Position | Stop Position |
|---|---|---|---|---|---|---|
| FE898349 | — | G | — | 59902504 | 59900436 | 59904573 |
| TC126194 | — | G | — | 59903297 | 59900692 | 59905902 |
| Glyma18g50900 | — | G | — | 59903417 | 59900433 | 59906401 |
| Gm_W82_CR18.G397200 | — | G | — | 59903471 | 59900386 | 59906556 |
| NGMAX008183850 | 52 | G | 18 | 59904561 | 59904411 | 59904712 |
| NGMAX008184740 | 53 | G | 18 | 60061797 | 60061647 | 60061948 |
| NS0204945 | 54 | G | 18 | 60261484 | 60261216 | 60261753 |
| NGMAX008190659 | 55 | G | 18 | 61262979 | 61262829 | 61263130 |
| NGMAX008190985 | 56 | G | 18 | 61322827 | 61322677 | 61322978 |
| NS0205638 | 57 | G | 18 | 61388468 | 61388179 | 61388758 |
| NGMAX008191317 | 58 | G | 18 | 61392161 | 61392011 | 61392312 |
| NS0092671 | 59 | G | 18 | 61432643 | 61432518 | 61432769 |
| NS0118292 | 60 | G | 18 | — | — | — |
| NGMAX008194551 | 61 | G | 18 | 61994225 | 61994075 | 61994376 |
| NGMAX008194952 | 62 | G | 18 | 62083082 | 62082932 | 62083233 |
| 108285_2293_0177 | — | G | 18 | 62090546 | 62090438 | 62090654 |
| Cf17723d | — | G | 18 | 62092956 | 62091890 | 62094023 |
| Cf14688d | — | G | 18 | 62095310 | 62094940 | 62095680 |

TABLE 32

Chromosome 18-Marker type and nucleic acid primers and probes useful in the detection of certain alleles of polymorphic nucleic acid markers associated with an iron deficiency growth condition tolerant phenotype.

| Marker or Locus Name | SEQ ID NO | Marker Type | Sequence |
|---|---|---|---|
| NS0092671 | 59 | TAQMAN | — |
| Primer 1 | 63 | — | TCTCCATTGCTAATAATTGCTTGAGT |
| Primer 2 | 64 | — | AACGAAAAGGGCTCAAAAACTAGTT |
| Probe 1 | 65 | — | ATTTGTTCTTTTTCTTTTC |
| Probe 2 | 66 | — | ATTTGTTTTTTTTCTTTTCC |

TABLE 32-continued

Chromosome 18-Marker type and nucleic acid primers and probes useful in the detection of certain alleles of polymorphic nucleic acid markers associated with an iron deficiency growth condition tolerant phenotype.

| Marker or Locus Name | SEQ ID NO | Marker Type | Sequence |
|---|---|---|---|
| N50118292 | 60 | TAQMAN | — |
| Primer 1 | 67 | — | GCGTCAATATCCTTTTCTAAAAGAAAACT |
| Primer 2 | 68 | — | GAAACGAGACGGATCGGGTT |
| Probe 1 | 69 | — | TCTTAGTATGAAAACTTC |
| Probe 2 | 70 | — | CTTAGTCTGAAAACTT |

TABLE 18

Chromosome 5 - QTL on chromosome 5 associated with a low iron growth condition tolerant phenotype.

| Marker or Locus Name | SEQ ID NO: | cM Map Position on chromosome five (5) | [-LOG10(P)] | Allelic Form(s) Associated With Low Fe Tolerance Phenotype[1] | Allelic Form(s) Not-Associated with Low Fe Tolerance Phenotype[1] | Polymorphic Position |
|---|---|---|---|---|---|---|
| Mt7 | — | — | — | — | — | — |
| WmFPC_Contig7872 | — | — | — | — | — | — |
| NGMAX006398059 | 71 | 36.1 | 7.5 | CC | TT | 201 |
| NGMAX006398075 | 72 | 36.1 | 7.4 | GG | CC | 201 |
| NGMAX006398171 | 73 | 36.1 | 8.3 | AA | GG | 201 |
| NGMAX006398585 | 74 | 36.2 | 9.6 | GG | AA | 201 |
| NGMAX006398641 | 75 | 36.2 | 8.7 | CC | TT | 201 |
| NGMAX006398662 | 76 | 36.2 | 7.7 | GG | AA | 201 |
| NGMAX006398682 | 77 | 36.2 | 7.3 | CC | TT | 201 |
| NS0203176 | 78 | 36.3 | 7.5 | TT | CC | 158 |
| NGMAX006398725 | 79 | 36.3 | 8.8 | CC | TT | 201 |
| NGMAX006398726 | 80 | 36.3 | 7.7 | GG | AA | 201 |
| NGMAX006398800 | 81 | 36.3 | 8.3 | AA | TT | 201 |
| NGMAX006398923 | 82 | 36.4 | 2.5 | CC | TT | 201 |
| NGMAX006399042 | 83 | 36.6 | 2.4 | CC | TT | 201 |
| NGMAX006399063 | 84 | 36.7 | 2.3 | AA | TT | 201 |
| NGMAX006399066 | 85 | 36.7 | 2.4 | GG | AA | 201 |
| NGMAX006399168 | 86 | 37 | 2.5 | CC | TT | 201 |
| NGMAX006399482 | 87 | 37.8 | 2.5 | CC | GG | 201 |
| NGMAX006400296 | 88 | 39.7 | 2.4 | CC | TT | 201 |
| NGMAX006401034 | 89 | 41.3 | 2.4 | GG | AA | 201 |
| NGMAX006401429 | 90 | 42.1 | 2.4 | GG | AA | 201 |
| NGMAX006401765 | 91 | 43 | 2.4 | GG | AA | 201 |
| NGMAX008341472 | 92 | 43.1 | 2.4 | CC | TT | 201 |
| NGMAX006401896 | 93 | 43.4 | 2.3 | GG | AA | 201 |
| BARCSOYSSR_05_0638 | — | — | — | — | — | — |
| BARCSOYSSR_05_0639 | — | — | — | — | — | — |
| BARCSOYSSR_05_0640 | — | — | — | — | — | — |

TABLE 19

Chromosome 5 - Physical positions of certain genetic markers on soybean chromosome 5 in proximity to QTL associated with a low iron growth condition tolerant phenotype.

| Marker or Locus Name | SEQ ID NO: | Linkage Group | Chromosome | Middle Position | Start Position | Stop Position |
|---|---|---|---|---|---|---|
| Mt7 | — | A1 | — | 5025107 | 1030287 | 9019927 |
| WmFPC_Contig7872 | — | A1 | — | 8685833 | 8611032 | 8760634 |
| NGMAX006398059 | 71 | A1 | 5 | 8726151 | 8726001 | 8726302 |
| NGMAX006398075 | 72 | A1 | 5 | 8734523 | 8734373 | 8734674 |
| NGMAX006398171 | 73 | A1 | 5 | 8792710 | 8792560 | 8792861 |
| NGMAX006398585 | 74 | A1 | 5 | 8976142 | 8975992 | 8976293 |

TABLE 19-continued

Chromosome 5 - Physical positions of certain genetic markers on soybean chromosome 5 in proximity to QTL associated with a low iron growth condition tolerant phenotype.

| Marker or Locus Name | SEQ ID NO: | Linkage Group | Chromosome | Middle Position | Start Position | Stop Position |
|---|---|---|---|---|---|---|
| NGMAX006398641 | 75 | A1 | 5 | 9000620 | 9000470 | 9000771 |
| NGMAX006398662 | 76 | A1 | 5 | 9012963 | 9012813 | 9013114 |
| NGMAX006398682 | 77 | A1 | 5 | 9029814 | 9029664 | 9029965 |
| NS0203176 | 78 | A1 | 5 | — | — | — |
| NGMAX006398725 | 79 | A1 | 5 | 9049261 | 9049111 | 9049412 |
| NGMAX006398726 | 80 | A1 | 5 | 9049476 | 9049326 | 9049627 |
| NGMAX006398800 | 81 | A1 | 5 | 9097034 | 9096884 | 9097185 |
| NGMAX006398923 | 82 | A1 | 5 | 9314324 | 9314174 | 9314475 |
| NGMAX006399042 | 83 | A1 | 5 | 9965092 | 9964942 | 9965243 |
| NGMAX006399063 | 84 | A1 | 5 | 10105665 | 10105515 | 10105816 |
| NGMAX006399066 | 85 | A1 | 5 | 10128724 | 10128574 | 10128875 |
| NGMAX006399168 | 86 | A1 | 5 | 10753843 | 10753693 | 10753994 |
| NGMAX006399482 | 87 | A1 | 5 | 12716483 | 12716333 | 12716634 |
| NGMAX006400296 | 88 | A1 | 5 | 17294815 | 17294665 | 17294966 |
| NGMAX006401034 | 89 | A1 | 5 | 21201293 | 21201143 | 21201444 |
| NGMAX006401429 | 90 | A1 | 5 | 23025196 | 23025046 | 23025347 |
| NGMAX006401765 | 91 | A1 | 5 | 25295468 | 25295318 | 25295619 |
| NGMAX008341472 | 92 | A1 | 5 | 25645573 | 25645423 | 25645724 |
| NGMAX006401896 | 93 | A1 | 5 | 26170513 | 26170363 | 26170664 |
| BARCSOYSSR__05__0638 | — | A1 | 5 | 26175552 | 26175536 | 26175569 |
| BARCSOYSSR__05__0639 | — | A1 | 5 | 26175863 | 26175838 | 26175889 |
| BARCSOYSSR__05__0640 | — | A1 | 5 | 26176446 | 26176422 | 26176471 |

TABLE 21

Chromosome 7 - QTL on chromosome 7 associated with a low iron growth condition tolerant phenotype.

| Marker or Locus Name | SEQ ID NO: | cM Map Position on chromosome seven (7) | [-LOG10(P)] | Allelic Form(s) Associated With Low Fe Tolerance Phenotype[1] | Allelic Form(s) Not-Associated with Low Fe Tolerance Phenotype[1] | Polymorphic Position |
|---|---|---|---|---|---|---|
| BQ081048 | — | — | — | — | — | — |
| Cf9876d | — | — | — | — | — | — |
| BARCSOYSSR__07__0184 | — | — | — | — | — | — |
| NGMAX006621532 | 94 | 26.9 | — | — | — | 201 |
| NGMAX006621610 | 95 | 27 | — | — | — | 201 |
| NGMAX006621674 | 96 | 27.1 | — | — | — | 201 |
| NGMAX006621699 | 97 | 27.2 | 2.6 | CC | GG | 201 |
| NGMAX006621706 | 98 | 27.3 | 3.1 | GG | TT | 201 |
| NGMAX006621720 | 99 | 28 | 2.9 | AA | TT | 201 |
| NGMAX006621726 | 100 | 28.1 | 3.1 | CC | AA | 201 |
| NGMAX006621767 | 101 | 29.1 | 2.3 | GG | AA | 201 |
| NGMAX006621777 | 102 | 29.2 | 2.3 | TT | CC | 201 |
| NGMAX006622006 | 103 | 30.2 | 2.3 | AA | GG | 201 |
| NGMAX006622614 | 104 | 31.4 | 2.2 | AA | CC | 201 |
| NGMAX006622952 | 105 | 32.4 | 2.4 | AA | GG | 201 |
| NGMAX006623558 | 106 | 37.3 | 4.3 | TT | CC | 201 |
| NGMAX006623995 | 107 | 38.5 | 4.2 | AA | TT | 201 |
| NGMAX006624271 | 108 | 38.9 | 4.3 | AA | TT | 201 |
| NGMAX006625883 | 109 | 41.1 | 3.7 | GG | AA | 201 |
| NGMAX006626085 | 110 | 41.4 | — | — | — | 201 |
| TC381430 | — | — | — | — | — | — |
| BI785468 | — | — | — | — | — | — |
| TA53357__3847 | — | — | — | — | — | — |

TABLE 22

Chromosome 7 - Physical positions of certain genetic markers on soybean chromosome 7 in proximity to QTL associated with a low iron growth condition tolerant phenotype.

| Marker or Locus Name | SEQ ID NO: | Linkage Group | Chromosome | Middle Position | Start Position | Stop Position |
|---|---|---|---|---|---|---|
| BQ081048 | — | M | — | 3391310 | 3391037 | 3391584 |
| Cf9876d | — | M | — | 3391817 | 3391703 | 3391932 |
| BARCSOYSSR_07_0184 | — | M | — | 3391983 | 3391959 | 3392008 |
| NGMAX006621532 | 94 | M | 7 | 3393181 | 3393031 | 3393332 |
| NGMAX006621610 | 95 | M | 7 | 3416698 | 3416548 | 3416849 |
| NGMAX006621674 | 96 | M | 7 | 3427488 | 3427338 | 3427639 |
| NGMAX006621699 | 97 | M | 7 | 3440243 | 3440093 | 3440394 |
| NGMAX006621706 | 98 | M | 7 | 3446408 | 3446258 | 3446559 |
| NGMAX006621720 | 99 | M | 7 | 3541629 | 3541479 | 3541780 |
| NGMAX006621726 | 100 | M | 7 | 3547338 | 3547188 | 3547489 |
| NGMAX006621767 | 101 | M | 7 | 3679963 | 3679813 | 3680114 |
| NGMAX006621777 | 102 | M | 7 | 3682891 | 3682741 | 3683042 |
| NGMAX006622006 | 103 | M | 7 | 3816426 | 3816276 | 3816577 |
| NGMAX006622614 | 104 | M | 7 | 3981204 | 3981054 | 3981355 |
| NGMAX006622952 | 105 | M | 7 | 4126472 | 4126322 | 4126623 |
| NGMAX006623558 | 106 | M | 7 | 4850390 | 4850240 | 4850541 |
| NGMAX006623995 | 107 | M | 7 | 5035538 | 5035388 | 5035689 |
| NGMAX006624271 | 108 | M | 7 | 5093132 | 5092982 | 5093283 |
| NGMAX006625883 | 109 | M | 7 | 5418926 | 5418776 | 5419077 |
| NGMAX006626085 | 110 | M | 7 | 5457846 | 5457696 | 5457997 |
| TC381430 | — | M | — | 5458590 | 5457600 | 5459580 |
| BI785468 | — | M | — | 5458604 | 5457683 | 5459525 |
| TA53357_3847 | — | M | — | 5458975 | 5457605 | 5460346 |

TABLE 33

Chromosome 7-Marker type and nucleic acid primer and probes useful in the detection of certain alleles of polymorphic nucleic acid markers associated with an iron deficiency growth condition tolerant phenotype.

| Marker or Locus Name | SEQ ID NO | Marker Type | Sequence |
|---|---|---|---|
| NS0120070 | 108 | TAQMAN | — |
| Primer 1 | 111 | — | ATTACGAATACCGTTGTTCAGTGACT |
| Primer 2 | 112 | — | ATCTTAGGTATATGAATTAAAACGAAAAATTAAGTTGA |
| Probe 1 | 113 | — | TCATCCCTCATAGTCTCAT |
| Probe 2 | 114 | — | CATCCCTCATTGTCTCAT |

TABLE 24

Chromosome 17 - QTL on chromosome 17 associated with a low iron growth condition tolerant phenotype.

| Marker or Locus Name | SEQ ID NO: | cM Map Position on chromosome seventeen (17) | [-LOG10(P)] | Allelic Form(s) Associated With Low Fe Tolerance Phenotype[1] | Allelic Form(s) Not-Associated with Low Fe Tolerance Phenotype[1] | Polymorphic Position |
|---|---|---|---|---|---|---|
| BG726970 | — | — | — | — | — | — |
| BARCSOYSSR_17_0169 | — | — | — | — | — | — |
| NGMAX007790014 | 115 | 21.3 | 2.1 | AA | TT | 201 |
| NGMAX007790381 | 116 | 22.5 | 4.2 | AA | CC | 201 |
| NGMAX007790411 | 117 | 22.6 | 4.2 | GG | AA | 201 |
| NGMAX007790440 | 118 | 22.8 | 4.2 | CC | TT | 201 |
| NS0263544 | 119 | | 4.3 | GG | TT | 61 |
| NGMAX007790913 | 120 | 24.8 | 4.3 | GG | AA | 201 |
| NGMAX007790961 | 121 | 24.9 | 3.8 | AA | TT | 201 |
| NGMAX007790982 | 122 | 25 | 3.8 | CC | GG | 201 |
| NGMAX007793044 | 123 | 34.8 | 3.8 | AA | GG | 201 |
| BARCSOYSSR_17_0274 | — | — | — | — | — | — |

TABLE 24-continued

Chromosome 17 - QTL on chromosome 17 associated with a low iron growth condition tolerant phenotype.

| Marker or Locus Name | SEQ ID NO: | cM Map Position on chromosome seventeen (17) | [-LOG10(P)] | Allelic Form(s) Associated With Low Fe Tolerance Phenotype[1] | Allelic Form(s) Not-Associated with Low Fe Tolerance Phenotype[1] | Polymorphic Position |
|---|---|---|---|---|---|---|
| 086788_3391_0381 | — | — | — | — | — | — |
| Contig41076 | — | — | — | — | — | — |

TABLE 25

Chromosome 17 - Physical positions of certain genetic markers on soybean chromosome 17 in proximity to QTL associated with a low iron growth condition tolerant phenotype.

| Marker or Locus Name | SEQ ID NO: | Linkage Group | Chromosome | Middle Position | Start Position | Stop Position |
|---|---|---|---|---|---|---|
| BG726970 | — | D2 | — | 3146669 | 3146028 | 3147311 |
| BARCSOYSSR_17_0169 | — | D2 | — | 3147380 | 3147349 | 3147411 |
| NGMAX007790014 | 115 | D2 | 17 | 3155846 | 3155696 | 3155997 |
| NGMAX007790381 | 116 | D2 | 17 | 3323894 | 3323744 | 3324045 |
| NGMAX007790411 | 117 | D2 | 17 | 3330003 | 3329853 | 3330154 |
| NGMAX007790440 | 118 | D2 | 17 | 3364493 | 3364343 | 3364644 |
| NS0263544 | 119 | D2 | 17 | | | |
| NGMAX007790913 | 120 | D2 | 17 | 3633825 | 3633675 | 3633976 |
| NGMAX007790961 | 121 | D2 | 17 | 3647560 | 3647410 | 3647711 |
| NGMAX007790982 | 122 | D2 | 17 | 3656432 | 3656282 | 3656583 |
| NGMAX007793044 | 123 | D2 | 17 | 4984616 | 4984466 | 4984767 |
| BARCSOYSSR_17_0274 | — | D2 | — | 4996895 | 4996872 | 4996919 |
| 086788_3391_0381 | — | D2 | — | 4999026 | 4998989 | 4999064 |
| Contig41076 | — | D2 | — | 8774035 | 8773912 | 8774159 |

TABLE 27

Chromosome 19 - QTL on chromosome 19 associated with a low iron growth condition tolerant phenotype.

| Marker or Locus Name | SEQ ID NO: | cM Map Position on chromosome nineteen (19) | [-LOG10(P)] | Allelic Form(s) Associated With Low Fe Tolerance Phenotype[1] | Allelic Form(s) Not-Associated with Low Fe Tolerance Phenotype[1] | Polymorphic Position |
|---|---|---|---|---|---|---|
| Glyma19g01630 | — | — | — | — | — | — |
| AI437921 | — | — | — | — | — | — |
| BARCSOYSSR_19_0083 | — | — | — | — | — | — |
| NGMAX008199658 | 124 | 23 | 2.4 | GG | AA | 201 |
| NGMAX008199750 | 125 | 23.1 | 2.2 | CC | TT | 201 |
| NGMAX008199864 | 126 | 23.2 | 2.4 | AA | GG | 201 |
| NGMAX008199973 | 127 | 23.3 | 2.7 | AA | CC | 201 |
| NGMAX008200015 | 128 | 23.4 | 2.5 | AA | GG | 201 |
| NGMAX008200022 | 129 | 23.5 | 2.4 | GG | AA | 201 |
| NGMAX008200044 | 130 | 23.7 | 2.1 | GG | AA | 201 |
| NGMAX008200052 | 131 | 23.8 | 2.2 | TT | CC | 201 |
| NGMAX008200275 | 132 | 24.2 | 2.0 | CC | TT | 201 |
| NGMAX008200335 | 133 | 24.3 | 2.7 | CC | GG | 201 |
| NGMAX008200568 | 134 | 24.7 | 2.4 | GG | AA | 201 |
| NGMAX008200652 | 135 | 24.8 | 2.6 | TT | AA | 201 |
| NGMAX008200656 | 136 | 24.9 | 2.6 | AA | GG | 201 |
| NGMAX008200785 | 137 | 25 | 2.6 | TT | AA | 201 |
| NGMAX008200913 | 138 | 25.8 | — | — | — | 201 |
| 354114_3517_2150 | — | — | — | — | — | — |
| TC409049 | — | — | — | — | — | — |
| Contig30217 | — | — | — | — | — | — |
| TC27203 | — | — | — | — | — | — |

TABLE 28

Chromosome 19 - Physical positions of certain genetic markers on soybean chromosome 19 in proximity to QTL associated with a low iron growth condition tolerant phenotype.

| Marker or Locus Name | SEQ ID NO: | Linkage Group | Chromosome | Middle Position | Start Position | Stop Position |
|---|---|---|---|---|---|---|
| Glyma19g01630 | — | L | — | 1239942 | 1239090 | 1240794 |
| AI437921 | — | L | — | 1240076 | 1239926 | 1240227 |
| BARCSOYSSR_19_0083 | — | L | — | 1250166 | 1250134 | 1250199 |
| NGMAX008199658 | 124 | L | 19 | 1253876 | 1253726 | 1254027 |
| NGMAX008199750 | 125 | L | 19 | 1272580 | 1272430 | 1272731 |
| NGMAX008199864 | 126 | L | 19 | 1296597 | 1296447 | 1296748 |
| NGMAX008199973 | 127 | L | 19 | 1309430 | 1309280 | 1309581 |
| NGMAX008200015 | 128 | L | 19 | 1333922 | 1333772 | 1334073 |
| NGMAX008200022 | 129 | L | 19 | 1337886 | 1337736 | 1338037 |
| NGMAX008200044 | 130 | L | 19 | 1392293 | 1392143 | 1392444 |
| NGMAX008200052 | 131 | L | 19 | 1414176 | 1414026 | 1414327 |
| NGMAX008200275 | 132 | L | 19 | 1490595 | 1490445 | 1490746 |
| NGMAX008200335 | 133 | L | 19 | 1502649 | 1502499 | 1502800 |
| NGMAX008200568 | 134 | L | 19 | 1593019 | 1592869 | 1593170 |
| NGMAX008200652 | 135 | L | 19 | 1615310 | 1615160 | 1615461 |
| NGMAX008200656 | 136 | L | 19 | 1617556 | 1617406 | 1617707 |
| NGMAX008200785 | 137 | L | 19 | 1651426 | 1651276 | 1651577 |
| NGMAX008200913 | 138 | L | 19 | 1813963 | 1813813 | 1814114 |
| 354114_3517_2150 | — | L | — | 1815264 | 1815145 | 1815383 |
| TC409049 | — | L | — | 1817184 | 1817061 | 1817307 |
| Contig30217 | — | L | — | 1817248 | 1817012 | 1817485 |
| TC27203 | — | L | — | 1818026 | 1817097 | 1818955 |

TABLE 30

Chromosome 9 - QTL on chromosome 9 associated with a low iron growth condition tolerant phenotype.

| Marker or Locus Name | SEQ ID NO: | cM Map Position on chromosome nine (9) | [-LOG10(P)] | Allelic Form(s) Associated With Low Fe Tolerance Phenotype[1] | Allelic Form(s) Not-Associated with Low Fe Tolerance Phenotype[1] | Polymorphic Position |
|---|---|---|---|---|---|---|
| Cf4289d | — | — | — | — | — | — |
| Cf9351d | — | — | — | — | — | — |
| BARCSOYSSR_09_1350 | — | — | — | — | — | — |
| NGMAX006925911 | 139 | 120.4 | — | — | — | 201 |
| NGMAX006925967 | 140 | 120.5 | — | — | — | 201 |
| NGMAX006926063 | 141 | 120.6 | — | — | — | 201 |
| NGMAX006926228 | 142 | 121 | 2.1 | GG | AA | 201 |
| NGMAX006926426 | 143 | 121.5 | 2.5 | TT | CC | 201 |
| NGMAX006926451 | 144 | 121.6 | 2.2 | CC | GG | 201 |
| NGMAX006926709 | 145 | 122.3 | 2.1 | TT | GG | 201 |
| NGMAX006926784 | 146 | 122.7 | 2.2 | GG | AA | 201 |
| NGMAX006926934 | 147 | 123.1 | 4.6 | CC | TT | 201 |
| NGMAX006926989 | 148 | 123.2 | 4.5 | TT | CC | 201 |
| NGMAX006927044 | 149 | 123.3 | 3.6 | TT | AA | 201 |
| NGMAX006927083 | 150 | 123.4 | 3.8 | GG | AA | 201 |
| NGMAX006927293 | 151 | 123.7 | 3.2 | AA | GG | 201 |
| NGMAX006927454 | 152 | 123.9 | 3.5 | GG | TT | 201 |
| NGMAX006927578 | 153 | 124.1 | 3.7 | AA | GG | 201 |
| NS0094370 | 154 | | 3.7 | CC | TT | 835 |
| NS0202727 | 155 | 124.2 | 3.8 | CC | TT | 310 |
| NGMAX006927737 | 156 | 124.3 | 3.6 | CC | TT | 201 |
| NGMAX006927783 | 157 | 124.4 | 3.1 | TT | AA | 201 |
| NGMAX006927836 | 158 | 124.5 | 3.2 | GG | AA | 201 |
| NGMAX006928046 | 159 | 124.8 | 3.5 | CC | AA | 201 |
| NS0123372 | 160 | 126.6 | 3.1 | TT | AA | 935 |
| NGMAX006928148 | 161 | 125.1 | 2.8 | CC | TT | 201 |
| NGMAX006928238 | 162 | 125.2 | 2.7 | TT | CC | 201 |
| NGMAX006928269 | 163 | 125.3 | 2.4 | CC | TT | 201 |
| NGMAX006928358 | 164 | 125.5 | 2.4 | CC | TT | 201 |
| NGMAX006928507 | 165 | 125.7 | 2.3 | CC | AA | 201 |
| NGMAX006928537 | 166 | 125.8 | 2.1 | GG | AA | 201 |
| NGMAX006928614 | 167 | 126.2 | 2.2 | TT | AA | 201 |
| NGMAX006928650 | 168 | 126.4 | 2.3 | AA | CC | 201 |
| NGMAX006928755 | 169 | 126.5 | 2.1 | CC | TT | 201 |

TABLE 30-continued

Chromosome 9 - QTL on chromosome 9 associated with a low iron growth condition tolerant phenotype.

| Marker or Locus Name | SEQ ID NO: | cM Map Position on chromosome nine (9) | [-LOG10(P)] | Allelic Form(s) Associated With Low Fe Tolerance Phenotype[1] | Allelic Form(s) Not-Associated with Low Fe Tolerance Phenotype[1] | Polymorphic Position |
|---|---|---|---|---|---|---|
| NS0202939 | 170 | | 2.3 | GG | AA | 336 |
| NS0119073 | 171 | 126.6 | 2.1 | GG | AA | 378 |
| NGMAX006928836 | 172 | 126.6 | 2.6 | CC | TT | 201 |
| NS0202984 | 173 | 126.6 | 2.6 | GG | TT | 123 |
| NGMAX006928848 | 174 | 126.7 | 2.6 | GG | TT | 201 |
| Cf5524d | — | — | — | — | — | — |
| Glyma09g34600 | — | — | — | — | — | — |
| FE711739 | — | — | — | — | — | — |
| Cf974d | — | — | — | — | — | — |

TABLE 31

Chromosome 9 - Physical positions of certain genetic markers on soybean chromosome 9 in proximity to QTL associated with a low iron growth condition tolerant phenotype.

| Marker or Locus Name | SEQ ID NO: | Linkage Group | Chromosome | Middle Position | Start Position | Stop Position |
|---|---|---|---|---|---|---|
| Cf4289d | — | K | — | 40236382 | 40236306 | 40236458 |
| Cf9351d | — | K | — | 40236414 | 40236349 | 40236479 |
| BARCSOYSSR_09_1350 | — | K | — | 40240987 | 40240969 | 40241006 |
| NGMAX006925911 | 139 | K | 9 | 40243868 | 40243718 | 40244019 |
| NGMAX006925967 | 140 | K | 9 | 40257331 | 40257234 | 40257429 |
| NGMAX006926063 | 141 | K | 9 | 40257571 | 40256966 | 40258176 |
| NGMAX006926228 | 142 | K | 9 | 40257637 | 40257091 | 40258183 |
| NGMAX006926426 | 143 | K | 9 | 40257922 | 40257075 | 40258769 |
| NGMAX006926451 | 144 | K | 9 | 40258000 | 40257213 | 40258787 |
| NGMAX006926709 | 145 | K | 9 | 40258263 | 40257069 | 40259458 |
| NGMAX006926784 | 146 | K | 9 | 40258266 | 40257075 | 40259458 |
| NGMAX006926934 | 147 | K | 9 | 40258327 | 40257199 | 40259456 |
| NGMAX006926989 | 148 | K | 9 | 40258408 | 40258084 | 40258733 |
| NGMAX006927044 | 149 | K | 9 | 40258426 | 40258198 | 40258654 |
| NGMAX006927083 | 150 | K | 9 | 40258427 | 40258198 | 40258656 |
| NGMAX006927293 | 151 | K | 9 | 40258455 | 40258198 | 40258712 |
| NGMAX006927454 | 152 | K | 9 | 40259019 | 40258729 | 40259309 |
| NGMAX006927578 | 153 | K | 9 | 40259060 | 40258694 | 40259427 |
| NS0094370 | 154 | K | 9 | 40259070 | 40258694 | 40259446 |
| NS0202727 | 155 | K | 9 | 40259074 | 40258700 | 40259448 |
| NGMAX006927737 | 156 | K | 9 | 40259082 | 40258719 | 40259446 |
| NGMAX006927783 | 157 | K | 9 | 40259135 | 40258861 | 40259409 |
| NGMAX006927836 | 158 | K | 9 | 40259940 | 40259790 | 40260091 |
| NGMAX006928046 | 159 | K | 9 | 40272552 | 40272402 | 40272703 |
| NS0123372 | 160 | K | 9 | 40274627 | 40274616 | 40274639 |
| NGMAX006928148 | 161 | K | 9 | 40276462 | 40276310 | 40276615 |
| NGMAX006928238 | 162 | K | 9 | 40276527 | 40276422 | 40276633 |
| NGMAX006928269 | 163 | K | 9 | 40276939 | 40276924 | 40276955 |
| NGMAX006928358 | 164 | K | 9 | 40277052 | 40276121 | 40277983 |
| NGMAX006928507 | 165 | K | 9 | 40277093 | 40275787 | 40278399 |
| NGMAX006928537 | 166 | K | 9 | 40277287 | 40276191 | 40278383 |
| NGMAX006928614 | 167 | K | 9 | 40278128 | 40277917 | 40278340 |
| NGMAX006928650 | 168 | K | 9 | 40278248 | 40278098 | 40278399 |
| NGMAX006928755 | 169 | K | 9 | 40278294 | 40278252 | 40278337 |
| NS0202939 | 170 | K | 9 | 40282224 | 40281133 | 40283316 |
| NS0119073 | 171 | K | 9 | 40282249 | 40281111 | 40283388 |
| NGMAX006928836 | 172 | K | 9 | 40282297 | 40281142 | 40283452 |
| NS0202984 | 173 | K | 9 | 40283092 | 40281313 | 40284872 |
| NGMAX006928848 | 174 | K | 9 | 40283140 | 40281104 | 40285177 |
| Cf5524d | — | K | 9 | 40283166 | 40281155 | 40285177 |
| Glyma09g34600 | — | K | 9 | 40283199 | 40281116 | 40285283 |
| FE711739 | — | K | 9 | 40284092 | 40283359 | 40284825 |
| Cf974d | — | K | 9 | 40284100 | 40283206 | 40284995 |

TABLE 34

Chromosome 9-Marker type and nucleic acid primer and probes useful in the detection of certain alleles of polymorphic nucleic acid markers associated with an iron deficiency growth condition tolerant phenotype.

| Marker or Locus Name | SEQ ID NO | Marker Type | Sequence |
|---|---|---|---|
| NS0094370 | | TAQMAN | — |
| Primer 1 | 175 | — | CCGTATGCTGCATTTGTGTATTC |
| Primer 2 | 176 | — | TGCATAACCGTCCAATGTATTTTG |
| Probe 1 | 177 | — | TAGTGCAGCAGGAAA |
| Probe 2 | 178 | — | TGCAGTAGGAAATC |
| NS0123372 | | TAQMAN | — |
| Primer 1 | 179 | — | CCCGATCAGCTGCTTTTTAGG |
| Primer 2 | 180 | — | CGCCCTTCTCCTGGACAAC |
| Probe 1 | 181 | — | CTGATCTAGTTGGAATAG |
| Probe 2 | 182 | — | ACTGATCTAGTAGGAATAG |
| NS0119073 | | TAQMAN | — |
| Primer 1 | 183 | — | GAATGGAAGCTGGTATTGATATTTGATA |
| Primer 2 | 184 | — | TTATCTCCCCTCTCACTTTCACTACA |
| Probe 1 | 185 | — | TGACTACGACATGCAC |
| Probe 2 | 186 | — | TGACTATGACATGCACG |

Provided herein is a QTL on chromosome 18—that is flanked by loci FE898349 and Cf14688d—that is associated with a low iron growth condition tolerant phenotype. Sub-regions of chromosome 18 that flank a QTL associated with a low iron growth condition tolerant phenotype include, but are not limited to sub-regions defined by any of the following sets of loci:
a) loci FE898349 and 108285_2293_0177;
b) loci FE898349 and Cf17723d;
c) loci TC126194 and 108285_2293_0177;
d) loci TC126194 and Cf14688d;
e) loci TC126194 and Cf17723d;
f) loci Glyma18g50900 and 108285_2293_0177;
g) loci Glyma18g50900 and Cf14688d; or
h) loci Glyma18g50900 and Cf17723d.
(Table 15).

These loci flank a genomic interval that spans telomere proximal nucleotide 59900436 to centromere proximal nucleotide 62095680 in the physical map of linkage group G provided in the Table 16. Polymorphic nucleic acid markers located in this genomic interval that are associated with a low iron growth condition tolerant phenotype include, but are not limited to: NGMAX008183850 (SEQ ID NO: 52); NGMAX008184740 (SEQ ID NO: 53); NS0204945 (SEQ ID NO: 54); NGMAX008190659 (SEQ ID NO: 55); NGMAX008190985 (SEQ ID NO: 56); NS0205638 (SEQ ID NO: 57); NGMAX008191317 (SEQ ID NO: 58); NS0092671 (SEQ ID NO: 59); NS0118292 (SEQ ID NO: 60); NGMAX008194551 (SEQ ID NO: 61); and NGMAX008194952 (SEQ ID NO: 62).

In certain embodiments of the invention, it is useful to detect in, or determine, whether a soybean plant has an allelic state that is associated with a low iron growth condition tolerant phenotype (Table 15). Certain non-limiting exemplary examples include identifying a soybean plant that has any one or more of: the CC allelic state of the polymorphic nucleic acid of NGMAX008183850 (SEQ ID NO: 52); the GG allelic state of NGMAX008184740 (SEQ ID NO: 53); the GG allelic state of NS0204945 (SEQ ID NO: 54); the TT allelic state of NGMAX008090659 (SEQ ID NO: 55); the AA allelic state of NGMAX008190985 (SEQ ID NO: 56); the GG allelic state of NS0205638 (SEQ ID NO: 57); the TT allelic state of NGMAX008191317 (SEQ ID NO: 58); the TT allelic state of NS0092671 (SEQ ID NO: 59); the CC allelic state of NS0118292 (SEQ ID NO: 60); the TT allelic state of NGMAX008194551 (SEQ ID NO: 61); or the TT allelic state of NGMAX008194952 (SEQ ID NO: 62). One of skill in the art will also recognize that it can be useful to identify at a genetic locus a polymorphic nucleic acid marker that is not associated with a low iron growth condition tolerant phenotype (Table 15) in a plant or germplasm, such as when introgressing a QTL associated with a low iron growth tolerant phenotype into a genetic background not associated with such a phenotype.

Provided herein is a QTL on chromosome 5—that is flanked by loci Mt7 and BARCSOYSSR_05_0640—that is associated with a low iron growth condition tolerant phenotype. Sub-regions of chromosome 5 that flank a QTL associated with a low iron growth condition tolerant phenotype include, but are not limited to sub-regions defined by any of the following sets of loci:
a) loci Mt7 and BARCSOYSSR_05_0638;
b) loci Mt7 and BARCSOYSSR_05_0639;
c) loci WmFPC_Contig7872 and BARCSOYSSR_05_0638;
d) loci WmFPC_Contig7872 and BARCSOYSSR_05_0639; or
e) loci WmFPC_Contig7872 and BARCSOYSSR_05_0640.
(Table 18).

These loci flank a genomic interval that spans telomere proximal nucleotide 1030287 to centromere proximal nucleotide 26176471 in the physical map of linkage group A1 provided in Table 19. Polymorphic nucleic acid markers located in this genomic interval that are associated with a low iron growth condition tolerant phenotype can be detected with polymorphic nucleic acid markers that include, but are not limited to: NGMAX006398059 (SEQ ID NO: 71); NGMAX006398075 (SEQ ID NO: 72); NGMAX006398171 (SEQ ID NO: 73); NGMAX006398585 (SEQ ID NO: 74); NGMAX006398641 (SEQ ID NO: 75); NGMAX006398662 (SEQ ID NO: 76); NGMAX006398682 (SEQ ID NO: 77); NS0203176 (SEQ ID NO: 78); NGMAX006398725 (SEQ ID NO: 79); NGMAX006398726 (SEQ ID NO: 80); NGMAX006398800 (SEQ ID NO: 81); NGMAX006398923 (SEQ ID NO: 82); NGMAX006399042 (SEQ ID NO: 83); NGMAX006399063 (SEQ ID NO: 84); NGMAX006399066 (SEQ ID NO: 85); NGMAX006399168 (SEQ ID NO: 86); NGMAX006399482 (SEQ ID NO: 87); NGMAX006400296 (SEQ ID NO: 88); NGMAX006401034 (SEQ ID NO: 89); NGMAX006401429 (SEQ ID NO: 90); NGMAX006401765 (SEQ ID NO: 91);

NGMAX008341472 (SEQ ID NO: 92); and NGMAX006401896 (SEQ ID NO: 93).

In certain embodiments of the invention, it is useful to detect in, or determine, whether a soybean plant has an allelic state that is associated with a low iron growth condition tolerant phenotype (Table 18). Certain non-limiting exemplary examples include identifying a soybean plant that has any one or more of: the CC allelic state of the polymorphic nucleic acid of NGMAX006398059_(SEQ ID NO: 71); the GG allelic state of the polymorphic nucleic acid of NGMAX006398075 (SEQ ID NO: 72); the AA allelic state of the polymorphic nucleic acid of NGMAX006398171 (SEQ ID NO: 73); the GG allelic state of the polymorphic nucleic acid of NGMAX006398585 (SEQ ID NO: 74); the CC allelic state of the polymorphic nucleic acid of NGMAX006398641 (SEQ ID NO: 75); the GG allelic state of the polymorphic nucleic acid of NGMAX006398662 (SEQ ID NO: 76); the CC allelic state of the polymorphic nucleic acid of NGMAX006398682 (SEQ ID NO: 77); the TT allelic state of the polymorphic nucleic acid of NS0203176 (SEQ ID NO: 78); the CC allelic state of the polymorphic nucleic acid of NGMAX006398725 (SEQ ID NO: 79); the GG allelic state of the polymorphic nucleic acid of NGMAX006398726 (SEQ ID NO: 80); the AA allelic state of the polymorphic nucleic acid of NGMAX006398800 (SEQ ID NO: 81); the CC allelic state of the polymorphic nucleic acid of NGMAX006398923 (SEQ ID NO: 82); the CC allelic state of the polymorphic nucleic acid of NGMAX006399042 (SEQ ID NO: 83); the AA allelic state of the polymorphic nucleic acid of NGMAX006399063 (SEQ ID NO: 84); the GG allelic state of the polymorphic nucleic acid of NGMAX006399066 (SEQ ID NO: 85); the CC allelic state of the polymorphic nucleic acid of NGMAX006399168 (SEQ ID NO: 86); the CC allelic state of the polymorphic nucleic acid of NGMAX006399482 (SEQ ID NO: 87); the CC allelic state of the polymorphic nucleic acid of NGMAX006400296 (SEQ ID NO: 88); the GG allelic state of the polymorphic nucleic acid of NGMAX006401034 (SEQ ID NO: 89); the GG allelic state of the polymorphic nucleic acid of NGMAX006401429 (SEQ ID NO: 90); the GG allelic state of the polymorphic nucleic acid of NGMAX006401765 (SEQ ID NO: 91); the CC allelic state of the polymorphic nucleic acid of NGMAX008341472 (SEQ ID NO: 92); and the GG allelic state of the polymorphic nucleic acid of NGMAX006401896 (SEQ ID NO: 93). One of skill in the art will also recognize that it can be useful to identify at a genetic locus a polymorphic nucleic acid marker that is not associated with a low iron growth condition tolerant phenotype (Table 18) in a plant or germplasm, such as when introgressing a QTL associated with a low iron growth tolerant phenotype into a genetic background not associated with such a phenotype.

Provided herein is a QTL on chromosome 7—that is flanked by loci BQ081048 and TA53357_3847—that is associated with a low iron growth condition tolerant phenotype. Sub-regions of chromosome 7 that flank QTL associated with a low iron growth condition tolerant phenotype include, but are not limited to sub-regions defined by any of the following sets of loci:
 a) loci BQ081048 and NGMAX006626085;
 b) loci BQ081048 and TC381430;
 c) loci BQ081048 and BI785468;
 d) loci Cf9876d and NGMAX006626085;
 e) loci Cf9876d and TC381430;
 f) loci Cf9876d and BI785468;
 g) loci Cf9876d and TA53357_3847;
 h) loci BARCSOYSSR_07_0184 and NGMAX006626085;
 i) loci BARCSOYSSR_07_0184 and TC381430;
 j) loci BARCSOYSSR_07_0184 and BI785468;
 k) loci BARCSOYSSR_07_0184 and TA53357_3847;
 l) loci NGMAX006621532 and NGMAX006626085;
 m) loci NGMAX006621532 and TC381430;
 n) loci NGMAX006621532 and BI785468;
 o) loci NGMAX006621532 and TA53357_3847;
 p) loci NGMAX006621610 and NGMAX006626085;
 q) loci NGMAX006621610 and TC381430;
 r) loci NGMAX006621610 and BI785468;
 s) loci NGMAX006621610 and TA53357_3847;
 t) loci NGMAX006621674 and NGMAX006626085;
 u) loci NGMAX006621674 and TC381430;
 v) loci NGMAX006621674 and BI785468; or
 w) loci NGMAX006621674 and NGMAX006626085.
 (Table 21).

These loci flank a genomic interval that spans telomere proximal nucleotide 3391037 to centromere proximal nucleotide 5460346 in the physical map of linkage group M provided in the Table 22. Polymorphic nucleic acid markers located in this genomic interval that are associated with a low iron growth condition tolerant phenotype can be detected with polymorphic nucleic acid markers that include, but are not limited to: NGMAX006621699 (SEQ ID NO: 97); NGMAX006621706 (SEQ ID NO: 98); NGMAX006621720 (SEQ ID NO: 99); NGMAX006621726 (SEQ ID NO: 100); NGMAX006621767 (SEQ ID NO: 101); NGMAX006621777 (SEQ ID NO: 102); NGMAX006622006 (SEQ ID NO: 103); NGMAX006622614 (SEQ ID NO: 104); NGMAX006622952 (SEQ ID NO: 105); NGMAX006623558 (SEQ ID NO: 106); NGMAX006623995 (SEQ ID NO: 107); NGMAX006624271 (SEQ ID NO: 108); and NGMAX006625883 (SEQ ID NO: 109).

In certain embodiments of the invention, it is useful to detect in, or determine whether, a soybean plant has an allelic state that is associated with a low iron growth condition tolerant phenotype (Table 21). Certain non-limiting exemplary examples include identifying a soybean plant that has any one or more of: the CC allelic state of the polymorphic nucleic acid of NGMAX006621699 (SEQ ID NO: 97); the GG allelic state of the polymorphic nucleic acid of NGMAX006621706 (SEQ ID NO: 98); the AA allelic state of the polymorphic nucleic acid of NGMAX006621720 (SEQ ID NO: 99); the CC allelic state of the polymorphic nucleic acid of NGMAX006621726 (SEQ ID NO: 100); the GG allelic state of the polymorphic nucleic acid of NGMAX006621767 (SEQ ID NO: 101); the TT allelic state of the polymorphic nucleic acid of NGMAX006621777 (SEQ ID NO: 102); the AA allelic state of the polymorphic nucleic acid of NGMAX006622006 (SEQ ID NO: 103); the AA allelic state of the polymorphic nucleic acid of NGMAX006622614 (SEQ ID NO: 104); the AA allelic state of the polymorphic nucleic acid of NGMAX006622952 (SEQ ID NO: 105); the TT allelic state of the polymorphic nucleic acid of NGMAX006623558 (SEQ ID NO: 106); the AA allelic state of the polymorphic nucleic acid of NGMAX006623995 (SEQ ID NO: 107); the AA allelic state of the polymorphic nucleic acid of NGMAX006624271 (SEQ ID NO: 108); and the GG allelic state of the polymorphic nucleic acid of NGMAX006625883 (SEQ ID NO: 109). One of skill in the art will also recognize that it can be useful to identify at a genetic locus a polymorphic nucleic acid marker that is not associated with a low iron growth condition tolerant phenotype (Table 21) in a plant or germplasm, such as when introgressing a QTL associated with a low iron growth tolerant phenotype into a genetic background not associated with such a phenotype.

Provided herein is a QTL on chromosome 17—that is flanked by loci BG726970 and Contig41076—that is associated with a low iron growth condition tolerant phenotype. Sub-regions of chromosome 17 that flank this first QTL associated with a low iron growth condition tolerant phenotype include, but are not limited to sub-regions defined by any of the following sets of loci:
 a) loci BG726970 and BARCSOYSSR_17_0274;
 b) loci BG726970 and 086788_3391_0381;
 c) loci BARCSOYSSR_17_0169 and BARCSOYSSR_17_0274;
 d) loci BARCSOYSSR_17_0169 and 086788_3391_0381; or
 e) loci BARCSOYSSR_17_0169 and Contig41076.
 (Table 24).

These loci flank a genomic interval that spans telomere proximal nucleotide 3146028 to centromere proximal nucleotide 8774159 in the physical map of linkage group D2 provided in the Table 25. Polymorphic nucleic acid markers located in this genomic interval that are associated with a low iron growth condition tolerant phenotype can be detected with polymorphic nucleic acid markers that include, but are not limited to: NGMAX007790014 (SEQ ID NO: 115); NGMAX007790381 (SEQ ID NO: 116); NGMAX007790411 (SEQ ID NO: 117); NGMAX007790440 (SEQ ID NO: 118); NS0263544 (SEQ ID NO: 119); NGMAX007790913 (SEQ ID NO: 120); NGMAX007790961 (SEQ ID NO: 121); NGMAX007790982 (SEQ ID NO: 122); and NGMAX007793044 (SEQ ID NO: 123).

In certain embodiments of the invention, it is useful to detect in, or determine whether, a soybean plant has an allelic state that is associated with a low iron growth condition tolerant phenotype (Table 24). Certain non-limiting exemplary examples include identifying a soybean plant that has any one or more of: the AA allelic state of the polymorphic nucleic acid of NGMAX007790014 (SEQ ID NO: 115); the AA allelic state of the polymorphic nucleic acid of NGMAX007790381 (SEQ ID NO: 116); the GG allelic state of the polymorphic nucleic acid of NGMAX007790411 (SEQ ID NO: 117); the CC allelic state of the polymorphic nucleic acid of NGMAX007790440 (SEQ ID NO: 118); the GG allelic state of the polymorphic nucleic acid of NS0263544 (SEQ ID NO: 119); the GG allelic state of the polymorphic nucleic acid of NGMAX007790913 (SEQ ID NO: 120); the AA allelic state of the polymorphic nucleic acid of NGMAX007790961 (SEQ ID NO: 121); the CC allelic state of the polymorphic nucleic acid of NGMAX007790982 (SEQ ID NO: 122); and the AA allelic state of the polymorphic nucleic acid of NGMAX007793044 (SEQ ID NO: 123). One of skill in the art will also recognize that it can be useful to identify at a genetic locus a polymorphic nucleic acid marker that is not associated with a low iron growth condition tolerant phenotype (Table 24) in a plant or germplasm, such as when introgressing a QTL associated with a low iron growth tolerant phenotype into a genetic background not associated with such a phenotype.

Provided herein is a QTL on chromosome 19—that is flanked by loci Glyma19g01630 and TC27203—that is associated with a low iron growth condition tolerant phenotype. Sub-regions of chromosome 19 that flank QTL associated with a low iron growth condition tolerant phenotype include, but are not limited to sub-regions defined by any of the following sets of loci:
 a) loci Glyma19g01630 and NGMAX008200913;
 b) loci Glyma19g01630 and 354114_3517_2150;
 c) loci Glyma19g01630 and TC409049;
 d) loci Glyma19g01630 and Contig30217;
 e) loci AI37921 and NGMAX008200913;
 f) loci AI37921 and 354114_3517_2150;
 g) loci AI37921 and TC409049;
 h) loci AI37921 and Contig30217;
 i) loci AI37921 and TC27203;
 j) loci BARCSOYSSR_19_0083 and NGMAX008200913;
 k) loci BARCSOYSSR_19_0083 and 354114_3517_2150;
 l) loci BARCSOYSSR_19_0083 and TC409049;
 m) loci BARCSOYSSR_19_0083 and Contig30217; or
 n) loci BARCSOYSSR_19_0083 and TC27203.
 (Table 27).

These loci flank a genomic interval that spans telomere proximal nucleotide 1239090 to centromere proximal nucleotide 1818955 in the physical map of linkage group L provided in the Table 28. Polymorphic nucleic acid markers located in this genomic interval that are associated with a low iron growth condition tolerant phenotype can be detected with polymorphic nucleic acid markers that include, but are not limited to: NGMAX008199658 (SEQ ID NO: 124), NGMAX008199750 (SEQ ID NO: 125), NGMAX008199864 (SEQ ID NO: 126), NGMAX008199973 (SEQ ID NO: 127), NGMAX008200015 (SEQ ID NO: 128); NGMAX008200022 (SEQ ID NO: 129); NGMAX008200044 (SEQ ID NO: 130); NGMAX008200052 (SEQ ID NO: 131); NGMAX008200275 (SEQ ID NO: 132); NGMAX008200335 (SEQ ID NO: 133); NGMAX008200568 (SEQ ID NO: 134); NGMAX008200652 (SEQ ID NO: 135); NGMAX008200656 (SEQ ID NO: 136); and NGMAX008200785 (SEQ ID NO: 137).

In certain embodiments of the invention, it is useful to detect in, or determine whether, a soybean plant has an allelic state that is associated with a low iron growth condition tolerant phenotype (Table 27). Certain non-limiting exemplary examples include identifying a soybean plant that has any one or more of: the GG allelic state of the polymorphic nucleic acid of NGMAX008199658 (SEQ ID NO: 124), the CC allelic state of the polymorphic nucleic acid of NGMAX008199750 (SEQ ID NO: 125), the AA allelic state of the polymorphic nucleic acid of NGMAX008199864 (SEQ ID NO: 126), the AA allelic state of the polymorphic nucleic acid of NGMAX008199973 (SEQ ID NO: 127), the AA allelic state of the polymorphic nucleic acid of NGMAX008200015 (SEQ ID NO: 128); the GG allelic state of the polymorphic nucleic acid of NGMAX008200022 (SEQ ID NO: 129); the GG allelic state of the polymorphic nucleic acid of NGMAX008200044 (SEQ ID NO: 130); the TT allelic state of the polymorphic nucleic acid of NGMAX008200052 (SEQ ID NO: 131); the CC allelic state of the polymorphic nucleic acid of NGMAX008200275 (SEQ ID NO: 132); the CC allelic state of the polymorphic nucleic acid of NGMAX008200335 (SEQ ID NO: 133); the GG allelic state of the polymorphic nucleic acid of NGMAX008200568 (SEQ ID NO: 134); the TT allelic state of the polymorphic nucleic acid of NGMAX008200652 (SEQ ID NO: 135); the AA allelic state of the polymorphic nucleic acid of NGMAX008200656 (SEQ ID NO: 136); and the TT allelic state of the polymorphic nucleic acid of NGMAX008200785 (SEQ ID NO: 137). One of skill in the art will also recognize that it can be useful to identify at a genetic locus a polymorphic nucleic acid marker that is not associated with a low iron growth condition tolerant phenotype (Table 27) in a plant or germplasm, such as when introgressing a QTL associated with a low iron growth tolerant phenotype into a genetic background not associated with such a phenotype.

Provided herein is a QTL on chromosome 9—that is flanked by loci Cf4289d and Cf974d—that is associated with a low iron growth condition tolerant phenotype. Sub-regions of chromosome 9 that flank this first QTL associated with a low iron growth condition tolerant phenotype include, but are not limited to sub-regions defined by any of the following sets of loci:
a) loci Cf4289d and Cf5524d;
b) loci Cf4289d and Glyma09g34600;
c) loci Cf4289d and FE711739;
d) loci Cf9351d and Cf5524d;
e) loci Cf9351d and Glyma09g34600;
f) loci Cf9351d and FE711739;
g) loci Cf9351d and Cf974d;
h) loci BARCSOYSSR_09_1350 and Cf5524d;
i) loci BARCSOYSSR_09_1350 and Glyma09g34600;
j) loci BARCSOYSSR_09_1350 and FE711739; or
k) loci BARCSOYSSR_09_1350 and Cf974d.
(Table 30).

These loci flank a genomic interval that spans telomere proximal nucleotide 40236306 to centromere proximal nucleotide 40284995 in the physical map of linkage group K provided in the Table 31. Polymorphic nucleic acid markers located in this genomic interval that are associated with a low iron growth condition tolerant phenotype can be detected with polymorphic nucleic acid markers that include, but are not limited to: NGMAX006925911 (SEQ ID NO: 139), NGMAX006925967 (SEQ ID NO: 140), NGMAX006926063 (SEQ ID NO: 141), NGMAX006926228 (SEQ ID NO: 142), NGMAX006926426 (SEQ ID NO: 143); NGMAX006926451 (SEQ ID NO: 144); NGMAX006926709 (SEQ ID NO: 145); NGMAX006926784 (SEQ ID NO: 146); NGMAX006926934 (SEQ ID NO: 147); NGMAX006926989 (SEQ ID NO: 148); NGMAX006927044 (SEQ ID NO: 149); NGMAX006927083 (SEQ ID NO: 150); NGMAX006927293 (SEQ ID NO: 151); NGMAX006927454 (SEQ ID NO: 152); NGMAX006927578 (SEQ ID NO: 153); NS0094370 (SEQ ID NO: 154); NS0202727 (SEQ ID NO: 155); NGMAX006927737 (SEQ ID NO: 156); NGMAX006927783 (SEQ ID NO: 157); NGMAX006927836 (SEQ ID NO: 158); NGMAX006928046 (SEQ ID NO: 159); NS0123372 (SEQ ID NO: 160); NGMAX006928148 (SEQ ID NO: 161); NGMAX006928238 (SEQ ID NO: 162); NGMAX006928269 (SEQ ID NO: 163); NGMAX006928358 (SEQ ID NO: 164); NGMAX006928507 (SEQ ID NO: 165); NGMAX006928537 (SEQ ID NO: 166); NGMAX006928614 (SEQ ID NO: 167); NGMAX006928650 (SEQ ID NO: 168); NGMAX006928755 (SEQ ID NO: 169); NS0202939 (SEQ ID NO: 170); NS0119073 (SEQ ID NO: 171); NGMAX006928836 (SEQ ID NO: 172); NS0202984 (SEQ ID NO: 173); and NGMAX006928848 (SEQ ID NO: 174).

In certain embodiments of the invention, it is useful to detect in, or determine whether, a soybean plant has an allelic state that is associated with a low iron growth condition tolerant phenotype (Table 30). Certain non-limiting exemplary examples include identifying a soybean plant that has any one or more of: the GG allelic state of the polymorphic nucleic acid of NGMAX006926228 (SEQ ID NO: 142), the TT allelic state of the polymorphic nucleic acid of NGMAX006926426 (SEQ ID NO: 143); the CC allelic state of the polymorphic nucleic acid of NGMAX006926451 (SEQ ID NO: 144); the TT allelic state of the polymorphic nucleic acid of NGMAX006926709 (SEQ ID NO: 145); the GG allelic state of the polymorphic nucleic acid of NGMAX006926784 (SEQ ID NO: 146); the CC allelic state of the polymorphic nucleic acid of NGMAX006926934 (SEQ ID NO: 147); the TT allelic state of the polymorphic nucleic acid of NGMAX006926989 (SEQ ID NO: 148); the TT allelic state of the polymorphic nucleic acid of NGMAX006927044 (SEQ ID NO: 149); the GG allelic state of the polymorphic nucleic acid of NGMAX006927083 (SEQ ID NO: 150); the AA allelic state of the polymorphic nucleic acid of NGMAX006927393 (SEQ ID NO: 151); the GG allelic state of the polymorphic nucleic acid of NGMAX006927454 (SEQ ID NO: 152); the AA allelic state of the polymorphic nucleic acid of NGMAX006927578 (SEQ ID NO: 153); the CC allelic state of the polymorphic nucleic acid of NS0094370 (SEQ ID NO: 154); the CC allelic state of the polymorphic nucleic acid of NS0202727 (SEQ ID NO: 155); the CC allelic state of the polymorphic nucleic acid of NGMAX006927737 (SEQ ID NO: 156); the TT allelic state of the polymorphic nucleic acid of NGMAX006927783 (SEQ ID NO: 157); the GG allelic state of the polymorphic nucleic acid of NGMAX006927836 (SEQ ID NO: 158); the CC allelic state of the polymorphic nucleic acid of NGMAX006928046 (SEQ ID NO: 159); the TT allelic state of the polymorphic nucleic acid of NS0123372 (SEQ ID NO: 160); the CC allelic state of the polymorphic nucleic acid of NGMAX006928148 (SEQ ID NO: 161); the TT allelic state of the polymorphic nucleic acid of NGMAX006928238 (SEQ ID NO: 162); the CC allelic state of the polymorphic nucleic acid of NGMAX006928269 (SEQ ID NO: 163); the CC allelic state of the polymorphic nucleic acid of NGMAX006928358 (SEQ ID NO: 164); the CC allelic state of the polymorphic nucleic acid of NGMAX006928507 (SEQ ID NO: 165); the GG allelic state of the polymorphic nucleic acid of NGMAX006928537 (SEQ ID NO: 166); the TT allelic state of the polymorphic nucleic acid of NGMAX006928614 (SEQ ID NO: 167); the AA allelic state of the polymorphic nucleic acid of NGMAX006928650 (SEQ ID NO: 168); the CC allelic state of the polymorphic nucleic acid of NGMAX006928755 (SEQ ID NO: 169); the GG allelic state of the polymorphic nucleic acid of NS0202939 (SEQ ID NO: 170); the GG allelic state of the polymorphic nucleic acid of NS0119073 (SEQ ID NO: 171); the CC allelic state of the polymorphic nucleic acid of NGMAX006928836 (SEQ ID NO: 172); the GG allelic state of the polymorphic nucleic acid of NS0202984 (SEQ ID NO: 173); and the GG allelic state of the polymorphic nucleic acid of NGMAX006928848 (SEQ ID NO: 174). One of skill in the art will also recognize that it can be useful to identify at a genetic locus a polymorphic nucleic acid marker that is not associated with a low iron growth condition tolerant phenotype (Table 30) in a plant or germplasm, such as when introgressing a QTL associated with a low iron growth tolerant phenotype into a genetic background not associated with such a phenotype.

Additional genetic markers can be used either in conjunction with the polymorphic nucleic acid markers provided in any of the Tables herein or independently of such markers. Publicly available marker databases from which useful markers can be obtained include, but are not limited to, the soybase.org website on the internet (World Wide Web) that is administered by the United States Agricultural Research Service, the United States Department of Agriculture, and Iowa State University. Additional soybean markers that can be used and that have been described in the literature include, but are not limited to, Hyten et al., BMC Genomics. 11:38, 2010; Choi et al., Genetics. 176(1):685-96, 2007; Yoon et al., Theor Appl Genet. 2007 March; 114(5):885-99; and Hyten et al. Crop Sci. 2010 50: 960-968.

Given the provision herein of genomic regions, QTL, and polymorphic markers identified herein as well as an assortment of soybean germplasms and their decedents from which tolerance to low iron growth conditions has been observed, additional markers located either within or near this genomic region that are associated with these phenotypes can be obtained by merely typing the new markers in the various germplasms provided herewith. The genomic regions, QTL, and polymorphic markers identified herein can also be mapped relative to markers provided in any publicly available or other soybean physical or genetic map to place this genetic locus on that map.

IV. Identification of Plants Exhibiting Tolerance to Low Iron Growth Conditions

To observe the presence or absence of low iron growth condition tolerant phenotypes, soybean plants comprising genotypes of interest can be exposed to low iron or iron deficient growth conditions in seedling stages, early to mid-vegetative growth stages, or in early reproductive stages. Experienced plant breeders can recognize tolerant soybean plants in the field, and can select the tolerant individuals or populations for breeding purposes or for propagation. In this context, the plant breeder recognizes "tolerant" and "susceptible" soybean plants in fortuitous naturally-occurring filed observations.

Breeders will appreciate, however, that plant tolerance is a phenotypic spectrum consisting of extremes in tolerance, susceptibility, and a continuum of intermediate phenotypes. Tolerance also varies due to environmental effects. Evaluation of phenotypes using reproducible assays and tolerance scoring methods are of value to scientists who seek to identify genetic loci that impart tolerance, conduct marker assisted selection to create tolerant soybean populations, and for introgression techniques to breed a tolerance trait into an elite soybean line, for example.

In contrast to fortuitous field observations that classify plants as either "tolerant" or "susceptible," various methods are known in the art for determining (and quantitating) the tolerance of a soybean plant to iron-deficient growth conditions. These techniques can be applied to different fields at different times, or to experimental greenhouse or laboratory settings, and provide approximate tolerance scores that can be used to characterize the tolerance of a given strain or line regardless of growth conditions or location. See, for example, Diers et al. (1992) "Possible identification of quantitative trait loci affecting iron efficiency in soybean," *J. Plant Nutr.* 15:217-2136; Dahiya and M. Singh (1979) "Effect of salinity, alkalinity and iron sources on availability of iron," *Plant and Soil* 51:13-18; and Gonzalez-Vallejo et al. (2000) "Iron Deficiency Decreases the Fe(III)-Chelate Reducing Activity of Leaf Protoplasts" *Plant Physiol.* 122 (2): 337-344.

The degree of IDC in a particular plant or stand of plants can be quantitated by using a system to score the severity of the disease in each plant. A plant strain or variety or a number of plant strains or varieties are planted and grown in a single stand in soil that is known to produce chlorotic plants as a result of iron deficiency ("field screens," i.e., in filed that have previously demonstrated IDC), or alternatively, in controlled nursery conditions. When the assay is conducted in controlled nursery conditions, defined soils can be used, where the concentration of iron (e.g., available iron) has been previously measured. The plants can be scored at maturity, or at any time before maturity. The scoring system rates each plant on a scale of one (most susceptible—most severe disease) to nine (most tolerant—no disease), as shown in Table 11.

TABLE 11

| Plant or Plant Stand Score | Symptoms |
| --- | --- |
| 1 | Most plants are completely dead. The plants that are still alive are approximately 10% of normal height, and have very little living tissue. |
| 2 | Most leaves are almost dead, most stems are still green. Plants are severely stunted (10-20% of normal height). |
| 3 | Most plants are yellow and necrosis is seen on most leaves. Most plants are approximately 20-40% of normal height. |
| 4 | Most plants are yellow, and necrosis is seen on the edges of less than half the leaves. Most plants are approximately 50% of normal height. |
| 5 | Most plants are light green to yellow, and no necrosis is seen on the leaves. Most plants are stunted (50-75% of normal height). |
| 6 | More than half the plants show moderate chlorosis, but no necrosis is seen on the leaves. |
| 7 | Less than half of the plants showing moderate chlorosis (light green leaves). |
| 8 | A few plants are showing very light chlorosis on one or two leaves. |
| 9 | All plants are normal green color. |

It will be appreciated that any such scale is relative, and furthermore, there may be variability between practitioners as to how the individual plants and the entire stand as a whole are scored. Optionally, the degree of chlorosis can be measured using a chlorophyll meter, e.g., a Minolta SPAD-502 Chlorophyll Meter, where readings off a single plant or a stand of plants can be made. Optionally, multiple readings can be obtained and averaged.

The IDC scoring of soybean stands can occur at any time. For example, plots can be scored in the early season, typically mid-July (depending on geographic latitude), so that the results can be used in making crossing decisions. Alternatively, soybean plots can be scored in the late season, which generally yields more precise data.

In general, while there is a certain amount of subjectivity to assigning severity measurements for disease symptoms, assignment to a given scale as noted above is well within the ordinary skill of a practitioner in the field. Measurements can also be averaged across multiple scores to reduce variation in field measurements.

Although protocols using field nurseries known to produce chlorotic plants can be used in assessing tolerance, it is typical for tolerance ratings to be based on actual field observations of fortuitous natural disease incidence, with the information corresponding to disease incidence for a cultivar being averaged over many locations and, typically, several season of crop plantings. Optionally, field stands or nursery/greenhouse plantings can be co-cultivated with IDC susceptibility "reference checks." A reference check is a planting of soybean strains or varieties with known susceptibilities to low iron growth conditions, for example, highly tolerant strains and highly susceptible strains. This parallel planting can aid the breeder to compare the plant pathology in the experimental stands with the plant pathology in the reference stands.

When plants are studied in a fortuitous natural field setting, if there is no chlorosis present, the rating system in Table 11 cannot be used, because the existence of iron-deficient soil cannot be ascertained. However, if some number of plants demonstrate IDC symptoms, the growth conditions in that filed can be assumed to be iron-deficient, and the entire stand can be scored. These scores can be accumulated over multiple locations and years to show disease tolerance for given varieties or cultivars. Relative tolerance measurements between different strains in the same field at the same time can easily be made using the described or equivalent scoring system. Furthermore, the tolerance rating can be updated and refined each year based on the previous year's observation in the field.

V. Introgression of a Genomic Region Associated with a Low Iron Growth Condition Tolerance Phenotype Provided herewith are unique soybean germplasms comprising one or more introgressed genomic regions, QTL, or polymorphic nucleic acid markers associated with a low iron growth condition tolerant phenotype and methods of obtaining the same. Marker-assisted introgression involves the transfer of a chromosomal region, defined by one or more markers, from one germplasm to a second germplasm. Offspring of a cross that contain the introgressed genomic region can be identified by the combination of markers characteristic of the desired introgressed genomic locus from a first germplasm (e.g., a low iron growth condition tolerant germplasm) and both linked and unlinked markers characteristic of the desired genetic background of a second germplasm (e.g., a low iron growth condition susceptible germplasm). In addition to the polymorphic nucleic acid markers provided herewith that identify alleles of certain QTL associated with a low iron growth condition tolerant phenotype, flanking markers that fall on both the telomere proximal end and the centromere proximal end of the genomic intervals comprising the QTL are also provided in Tables 1-10 and 14-31. Such flanking markers are useful in a variety of breeding efforts that include, but are not limited to, introgression of genomic regions associated with a low iron growth condition tolerant phenotype into a genetic background comprising markers associated with germplasm that ordinarily contains a genotype associated with a susceptible phenotype. Numerous markers that are linked and either immediately adjacent or adjacent to a low iron growth condition tolerant QTL in soybean that permit introgression of low iron growth condition tolerant QTL in the absence of extraneous linked DNA from the source germplasm containing the QTL are provided herewith. In certain embodiments, the linked and immediately adjacent markers are within about 105 kilobases (kB), 80 kB, 60 kB, 50 kB, 40 kB, 30 kB, 20 kB, 10 kB, 5 kB, 1 kB, 0.5 kB, 0.2 kB, or 0.1 kB of the introgressed genomic region. In certain embodiments, the linked and adjacent markers are within 1,000 kB, 600 kB, 500 kB, 400 kB, 300 kB, 200 kB, 150 kB of the introgressed genomic region. In certain embodiments, genomic regions comprising some or all of one or more of a low iron growth condition tolerant QTL described herein can be introgressed into the genomes of susceptible varieties by using markers that include, but are not limited to, adjacent markers and/or immediately adjacent markers provided in Tables 1-10 and 14-31. Those skilled in the art will appreciate that when seeking to introgress a smaller genomic region comprising a low iron growth condition tolerant QTL locus described herein, that any of the telomere proximal or centromere proximal markers that are immediately adjacent to a larger genomic region comprising a low iron growth condition tolerant QTL locus can also be used to introgress that smaller genomic region.

Provided herein are methods of introgressing any of the genomic regions comprising a low iron growth condition tolerance QTL locus of Tables 1-10 and 14-31 into soybean germplasm that lacks such a locus. In certain embodiments, the soybean germplasm that lacks such a genomic region comprising a low iron growth condition tolerance QTL locus of Tables 1-10 and 14-31 is susceptible or has less than optimal levels of tolerance to low iron growth conditions. In certain embodiments, the methods of introgression provided herein can yield soybean plants comprising introgressed genomic regions comprising one or more low iron growth condition tolerance QTL loci of Tables 1-10 and 14-31, where the immediately adjacent genomic DNA and/or some or all of the adjacent genomic DNA between the introgressed genomic region and the telomere or centromere will comprise allelic forms of the markers of Tables 1-10 and 14-31 that are characteristic of the germplasm into which the genomic region is introgressed and distinct from the germplasm from which the genomic region is derived. In certain embodiments, the soybean germplasm into which the genomic region is introgressed is germplasm that lacks such a low iron growth condition tolerance locus. In certain embodiments, the soybean germplasm into which the genomic region is introgressed is germplasm that lacks such a low iron growth condition tolerance locus and is either susceptible to low iron growth conditions or has less than optimal tolerance to low iron growth conditions.

Also provided herein are soybean plants produced by the aforementioned methods of introgression. In certain embodiments, such soybean plants will comprising introgressed genomic regions comprising a low iron growth condition tolerance QTL locus of Tables 1-10 and 14-31, where the immediately adjacent genomic DNA and/or some or all of the adjacent genomic DNA between the introgressed genomic region and the telomere or centromere will comprise allelic forms of the markers of Tables 1-10 that are characteristic of the germ plasm into which the genomic region is introgressed and distinct from the germplasm from which the genomic region is derived.

Soybean plants or germplasm comprising an introgressed genomic region that is associated with a low iron growth condition tolerant phenotype, wherein at least 10%, 25%, 50%, 75%, 90%, or 99% of the remaining genomic sequences carry markers characteristic of soybean plants or germplasm that are otherwise or ordinarily comprise a genomic region associated with susceptibility to low iron growth conditions, are thus provided. Furthermore soybean plants comprising an introgressed region where closely linked regions adjacent and/or immediately adjacent to the genomic regions, QTL, and markers provided herewith that comprise genomic sequences carrying markers characteristic of soybean plants or germplasm that are otherwise or ordinarily comprise a genomic region associated with the susceptibility to low iron growth conditions are also provided.

VI. Soybean Donor Plants Comprising Genomic Region Associated with Low Iron Growth Condition Phenotypes Low iron growth condition tolerance QTL allele or alleles can be introduced from any plant that contains that allele (donor) to any recipient soybean plant. In one aspect, the recipient soybean plant can contain additional low iron growth condition tolerance loci. In another aspect, the recipient soybean plant can contain a transgene. In another aspect, while maintaining the introduced QTL, the genetic contribution of the plant providing the low iron growth condition tolerance QTL can be reduced by back-crossing or other suitable approaches. In one aspect, the nuclear genetic material derived from the donor material in the soybean plant can be less than or about 50%, less than or about 25%, less than or about 13%, less than or about 5%, 3%, 2% or 1%, but that genetic material contains the low iron growth condition tolerance locus or loci of interest Plants containing one or more of the low iron growth condition tolerance loci described herein can be donor plants. In certain embodiments, a donor plant can be a susceptible line. In certain embodiments, a donor plant can also be a recipient soybean plant. A non-limiting and exemplary list of soybean varieties that are believed to comprise genomic regions associated with a low iron growth condition tolerance phenotype include, but are not limited to AG00501, AG00901, AG0131, AG0202, AG0231, AG0331, AG0401, AG801, AG0808, AG1031, AG1102, AG1230, AG2131, DKB22-52, AG3039, and AG3830 (Branded names of Asgrow (designated "AG") and DELAKB soybean varieties from Monsanto CO. 800 N. Lindbergh Blvd., St. Louis, Mo., USA.)

In a preferred embodiment, the donor soybean plant is AG801 and derivatives thereof, and is used as the resistant parent in a bi-parental mapping population to select for genomic regions associated with a low iron growth condition tolerance phenotype.

Also provided herewith are additional soybean plants that comprise a genomic region associated with a low iron growth condition tolerance phenotype that are identified by use of the markers provided in Tables 1-10 and 14-31 and/or methods provided herein. Any of the soybean plants identified above or other soybean plants that are otherwise identified using the markers or methods provided herein can be used in methods that include, but are not limited to, methods of obtaining soybean plants with an introgressed low iron growth condition tolerance locus, obtaining a soybean plant that exhibits a low iron growth condition tolerance phenotype, or obtaining a soybean plant comprising in its genome a genetic region associated with a low iron growth condition tolerance phenotype.

In certain embodiments, the soybean plants provided herein or used in the methods provided herein can comprise a transgene that confers tolerance to glyphosate. Transgenes that can confer tolerance to glyphosate include, but are not limited to, transgenes that encode glyphosate tolerant Class I EPSPS (5-enolpyruvylshikimate-3-phosphate synthases) enzymes or glyphosate tolerant Class II EPSPS (5-enolpyruvylshikimate-3-phosphate synthases) enzymes. Useful glyphosate tolerant EPSPS enzymes provided herein are disclosed in U.S. Pat. No. 6,803,501, RE39,247, U.S. Pat. Nos. 6,225,114, 5,188,642, and 4,971,908. In certain embodiments, the glyphosate tolerant soybean plants can comprise a transgene encoding a glyphosate oxidoreductase or other enzyme which degrades glyphosate. Glyphosate oxidoreductase enzymes had been described in U.S. Pat. No. 5,776,760 and U.S. Reissue Pat. RE38,825. In certain embodiments the soybean plant can comprise a transgene encoding a glyphosate N-acetyltransferase gene that confers tolerance to glyphosate. In certain embodiments, the soybean plant can comprise a glyphosate n-acetyltransferase encoding transgene such as those described in U.S. Pat. No. 7,666,644. In still other embodiments, soybean plants comprising combinations of transgenes that confer glyphosate tolerance are provided. Soybean plants comprising both a glyphosate resistant EPSPS and a glyphosate N-acetyltransferase are also provided herewith. In certain embodiments, it is contemplated that the soybean plants used herein can comprise one or more specific genomic insertion(s) of a glyphosate tolerant transgene including, but not limited to, as those found in: i) MON89788 soybean (deposited under ATCC accession number PTA-6708 and described in US Patent Application Publication Number 20100099859), ii) GTS 40-3-2 soybean (Padgette et al., Crop Sci. 35: 1451-1461, 1995), iii) event 3560.4.3.5 soybean (seed deposited under ATCC accession number PTA-8287 and described in US Patent Publication 20090036308), or any combination of i (MON89788 soybean), ii (GTS 40-3-2 soybean), and iii (event 3560.4.3.5 soybean).

A low iron growth condition tolerance associated QTL of the present invention may also be introduced into an soybean line comprising one or more transgenes that confer tolerance to herbicides including, but not limited to, glufosinate, dicamba, chlorsulfuron, and the like, increased yield, insect control, fungal disease resistance, virus resistance, nematode resistance, bacterial disease resistance, mycoplasma disease resistance, modified oils production, high oil production, high protein production, germination and seedling growth control, enhanced animal and human nutrition, low raffinose, environmental stress resistant, increased digestibility, industrial enzymes, pharmaceutical proteins, peptides and small molecules, improved processing traits, improved flavor, nitrogen fixation, hybrid seed production, reduced allergenicity, biopolymers, and biofuels among others. These agronomic traits can be provided by the methods of plant biotechnology as transgenes in soybean.

In certain embodiments, it is contemplated that genotypic assays that provide for non-destructive identification of the plant or plants can be performed either in seed, the emergence stage, the "VC" stage (i.e. cotyledons unfolded), the V1 stage (appearance of first node and unifoliate leaves), the V2 stage (appearance of the first trifoliate leaf), and thereafter. In certain embodiments, non-destructive genotypic assays are performed in seed using apparati and associated methods as described in U.S. Pat. Nos. 6,959,617; 7,134,351; 7,454,989; 7,502,113; 7,591,101; 7,611,842; and 7,685,768, which are incorporated herein by reference in their entireties. In certain embodiments, non-destructive genotypic assays are performed in seed using apparati and associated methods as described in US Patent Application Publications 20100086963, 20090215060, and 20090025288, which are incorporated herein by reference in their entireties. Published U.S. Patent Applications US 2006/0042527, US 2006/0046244, US 2006/0046264, US 2006/0048247, US 2006/0048248, US 2007/0204366, and US 2007/0207485, which are incorporated herein by reference in their entirety, also disclose apparatus and systems for the automated sampling of seeds as well as methods of sampling, testing and bulking seeds. Thus, in a certain embodiments, any of the methods provided herein can comprise screening for markers in individual seeds of a population wherein only seed with at least one genotype of interest is advanced.

VII. Molecular Assisted Breeding Techniques

Genetic markers that can be used in the practice of the instant invention include, but are not limited to, are Restriction Fragment Length Polymorphisms (RFLP), Amplified Fragment Length Polymorphisms (AFLP), Simple Sequence Repeats (SSR), Single Nucleotide Polymorphisms (SNP), Insertion/Deletion Polymorphisms (Indels), Variable Number Tandem Repeats (VNTR), and Random Amplified Polymorphic DNA (RAPD), and others known to those skilled in the art. Marker discovery and development in crops provides the initial framework for applications to marker-assisted breeding activities (US Patent Applications 2005/0204780, 2005/0216545, 2005/0218305, and 2006/00504538). The resulting "genetic map" is the representation of the relative position of characterized loci (DNA markers or any other locus for which alleles can be identified) along the chromosomes. The measure of distance on this map is relative to the frequency of crossover events between sister chromatids at meiosis.

As a set, polymorphic markers serve as a useful tool for fingerprinting plants to inform the degree of identity of lines or varieties (U.S. Pat. No. 6,207,367). These markers can form abasis for determining associations with phenotype and can be used to drive genetic gain. The implementation of marker-assisted selection is dependent on the ability to detect underlying genetic differences between individuals.

Certain genetic markers for use in the present invention include "dominant" or "codominant" markers. "Codominant markers" reveal the presence of two or more alleles (two per diploid individual). "Dominant markers" reveal the presence of only a single allele. The presence of the dominant marker phenotype (e.g., a band of DNA) is an indication that one allele is present in either the homozygous or heterozygous condition. The absence of the dominant marker phenotype (e.g., absence of a DNA band) is merely evidence that "some other" undefined allele is present. In the case of populations where individuals are predominantly homozygous and loci are predominantly dimorphic, dominant and codominant markers can be equally valuable. As populations become more heterozygous and multiallelic, codominant markers often become more informative of the genotype than dominant markers.

In another embodiment, markers that include. but are not limited, to single sequence repeat markers (SSR), AFLP markers, RFLP markers, RAPD markers, phenotypic markers, isozyme markers, single nucleotide polymorphisms (SNPs), insertions or deletions (Indels), single feature polymorphisms (SFPs, for example, as described in Borevitz et al. 2003 Gen. Res. 13:513-523), microarray transcription profiles, DNA-derived sequences, and RNA-derived sequences that are genetically linked to or correlated with low iron growth condition tolerance loci, regions flanking low iron growth condition tolerance loci, regions linked to low iron growth condition tolerance loci, and/or regions that are unlinked to low iron growth condition tolerance loci can be used in certain embodiments of the instant invention.

In one embodiment, nucleic acid-based analyses for determining the presence or absence of the genetic polymorphism (i.e. for genotyping) can be used for the selection of seeds in a breeding population. A wide variety of genetic markers for the analysis of genetic polymorphisms are available and known to those of skill in the art. The analysis may be used to select for genes, portions of genes, QTL, alleles, or genomic regions (Genotypes) that comprise or are linked to a genetic marker that is linked to or correlated with low iron growth condition tolerance loci, regions flanking low iron growth condition tolerance loci, regions linked to low iron growth condition tolerance loci, and/or regions that are unlinked to low iron growth condition tolerance loci can be used in certain embodiments of the instant invention.

Herein, nucleic acid analysis methods include, but are not limited to, PCR-based detection methods (for example, TaqMan assays), microarray methods, mass spectrometry-based methods and/or nucleic acid sequencing methods. In one embodiment, the detection of polymorphic sites in a sample of DNA, RNA, or cDNA may be facilitated through the use of nucleic acid amplification methods. Such methods specifically increase the concentration of polynucleotides that span the polymorphic site, or include that site and sequences located either distal or proximal to it. Such amplified molecules can be readily detected by gel electrophoresis, fluorescence detection methods, or other means.

A method of achieving such amplification employs the polymerase chain reaction (PCR) (Mullis et al. 1986 Cold Spring Harbor Symp. Quant. Biol. 51:263-273; European Patent 50,424; European Patent 84,796; European Patent 258,017; European Patent 237,362; European Patent 201,184; U.S. Pat. Nos. 4,683,202; 4,582,788; and 4,683,194), using primer pairs that are capable of hybridizing to the proximal sequences that define a polymorphism in its double-stranded form.

Methods for typing DNA based on mass spectrometry can also be used. Such methods are disclosed in U.S. Pat. Nos. 6,613,509 and 6,503,710, and references found therein.

Polymorphisms in DNA sequences can be detected or typed by a variety of effective methods well known in the art including, but not limited to, those disclosed in U.S. Pat. Nos. 5,468,613, 5,217,863; 5,210,015; 5,876,930; 6,030,787; 6,004,744; 6,013,431; 5,595,890; 5,762,876; 5,945,283; 5,468,613; 6,090,558; 5,800,944; 5,616,464; 7,312,039; 7,238,476; 7,297,485; 7,282,355; 7,270,981 and 7,250,252 all of which are incorporated herein by reference in their entireties. However, the compositions and methods of the present invention can be used in conjunction with any polymorphism typing method to type polymorphisms in genomic DNA samples. These genomic DNA samples used include but are not limited to genomic DNA isolated directly from a plant, cloned genomic DNA, or amplified genomic DNA.

For instance, polymorphisms in DNA sequences can be detected by hybridization to allele-specific oligonucleotide (ASO) probes as disclosed in U.S. Pat. Nos. 5,468,613 and 5,217,863. U.S. Pat. No. 5,468,613 discloses allele specific oligonucleotide hybridizations where single or multiple nucleotide variations in nucleic acid sequence can be detected in nucleic acids by a process in which the sequence containing the nucleotide variation is amplified, spotted on a membrane and treated with a labeled sequence-specific oligonucleotide probe.

Target nucleic acid sequence can also be detected by probe ligation methods as disclosed in U.S. Pat. No. 5,800,944 where sequence of interest is amplified and hybridized to probes followed by ligation to detect a labeled part of the probe.

Microarrays can also be used for polymorphism detection, wherein oligonucleotide probe sets are assembled in an overlapping fashion to represent a single sequence such that a difference in the target sequence at one point would result in partial probe hybridization (Borevitz et al., Genome Res. 13:513-523 (2003); Cui et al., Bioinformatics 21:3852-3858 (2005). On any one microarray, it is expected there will be a plurality of target sequences, which may represent genes and/or noncoding regions wherein each target sequence is represented by a series of overlapping oligonucleotides, rather than by a single probe. This platform provides for high throughput screening a plurality of polymorphisms. A single-feature polymorphism (SFP) is a polymorphism detected by a single probe in an oligonucleotide array, wherein a feature is a probe in the array. Typing of target sequences by microarray-based methods is disclosed in U.S. Pat. Nos. 6,799,122; 6,913,879; and 6,996,476.

Target nucleic acid sequence can also be detected by probe linking methods as disclosed in U.S. Pat. No. 5,616,464, employing at least one pair of probes having sequences homologous to adjacent portions of the target nucleic acid sequence and having side chains which non-covalently bind to form a stem upon base pairing of the probes to the target nucleic acid sequence. At least one of the side chains has a photoactivatable group which can form a covalent cross-link with the other side chain member of the stem.

Other methods for detecting SNPs and Indels include single base extension (SBE) methods. Examples of SBE methods include, but are not limited to, those disclosed in U.S. Pat. Nos. 6,004,744; 6,013,431; 5,595,890; 5,762,876; and 5,945,283. SBE methods are based on extension of a nucleotide primer that is adjacent to a polymorphism to incorporate a detectable nucleotide residue upon extension of the primer. In certain embodiments, the SBE method uses three synthetic oligonucleotides. Two of the oligonucleotides serve as PCR primers and are complementary to sequence of the locus of genomic DNA which flanks a region containing the polymorphism to be assayed. Following amplification of the region of the genome containing the polymorphism, the PCR product is mixed with the third oligonucleotide (called an extension primer) which is designed to hybridize to the amplified DNA adjacent to the polymorphism in the presence of DNA polymerase and two differentially labeled dideoxynucleosidetriphosphates. If the polymorphism is present on the template, one of the labeled dideoxynucleosidetriphosphates can be added to the primer in a single base chain extension. The allele present is then inferred by determining which of the two differential labels was added to the extension primer. Homozygous samples will result in only one of the two labeled bases being incorporated and thus only one of the two labels will be detected. Heterozygous samples have both alleles present, and will thus direct incorporation of both labels (into different molecules of the extension primer) and thus both labels will be detected.

In another method for detecting polymorphisms, SNPs and Indels can be detected by methods disclosed in U.S. Pat. Nos. 5,210,015; 5,876,930; and 6,030,787 in which an oligonucleotide probe having a 5' fluorescent reporter dye and a 3' quencher dye covalently linked to the 5' and 3' ends of the probe. When the probe is intact, the proximity of the reporter dye to the quencher dye results in the suppression of the reporter dye fluorescence, e.g. by Forster-type energy transfer. During PCR forward and reverse primers hybridize to a specific sequence of the target DNA flanking a polymorphism while the hybridization probe hybridizes to polymorphism-containing sequence within the amplified PCR product. In the subsequent PCR cycle DNA polymerase with 5'→3' exonuclease activity cleaves the probe and separates the reporter dye from the quencher dye resulting in increased fluorescence of the reporter.

In another embodiment, the locus or loci of interest can be directly sequenced using nucleic acid sequencing technologies. Methods for nucleic acid sequencing are known in the art and include technologies provided by 454 Life Sciences (Branford, Conn.), Agencourt Bioscience (Beverly, Mass.), Applied Biosystems (Foster City, Calif.), LI-COR Biosciences (Lincoln, Nebr.), NimbleGen Systems (Madison, Wis.), Illumina (San Diego, Calif.), and VisiGen Biotechnologies (Houston, Tex.). Such nucleic acid sequencing technologies comprise formats such as parallel bead arrays, sequencing by ligation, capillary electrophoresis, electronic microchips, "biochips," microarrays, parallel microchips, and single-molecule arrays, as reviewed by R.F. Service Science 2006 311:1544-1546.

The markers to be used in the methods of the present invention should preferably be diagnostic of origin in order for inferences to be made about subsequent populations. Experience to date suggests that SNP markers may be ideal for mapping because the likelihood that a particular SNP allele is derived from independent origins in the extant populations of a particular species is very low. As such, SNP markers appear to be useful for tracking and assisting introgression of QTLs, particularly in the case of Genotypes.

APPENDIX TO THE SPECIFICATION

TABLE 12

| Marker or Locus Name | SEQ ID NO | Source |
|---|---|---|
| Chromosome 3 (LG N) | | |
| Glyma03g34510 | — | Glyma1 |
| Gm_W82_CR03.G378360 | — | Gm_W82_CR03 |
| Glyma03g34760 | — | Glyma1 |
| Glyma03g34860 | — | Glyma1 |
| NS0202712 | 1 | — |
| Glyma03g35130 | — | Glyma1 |
| Glyma03g35280 | — | Glyma1 |
| NS0129403 | 2 | — |
| NS0115624 | 3 | — |
| Glyma03g36800 | — | Glyma1 |
| Glyma03g38030 | — | Glyma1 |
| NS0202842 | 4 | — |
| NS0122122 | 5 | — |
| NS0205984 | 6 | — |
| Pvcon3607 | — | Phaseolus_vulgaris |
| Glyma03g39610 | — | Glyma1 |
| FE710890 | — | Phaseolus_vulgaris |
| NS0202698 | 7 | — |
| Glyma03g41830 | — | Glyma1 |
| Glyma03g42250 | — | Glyma1 |

TABLE 12-continued

| Marker or Locus Name | SEQ ID NO | Source |
|---|---|---|
| Chromosome 19 (LG L) | | |
| Glyma19g32880 | — | Glyma1 |
| Glyma19g33540 | — | Glyma1 |
| NS0206298 | 20 | — |
| NS0205620 | 21 | — |
| NS0206055 | 22 | — |
| Glyma19g34480 | — | Glyma1 |
| NS0204985 | 23 | — |
| Gm_W82_CR19.G249620 | — | Gm_W82_CR19 |
| Glyma19g34740 | — | Glyma1 |
| NGMAX005710149 | — | — |
| 220298_3433_1666 | — | cajanus_cajan |
| Contig13742 | — | cajanus_cajan |
| BARCSOYSSR_19_1192 | — | Wm82_potential_SSR |
| Glyma19g34750 | — | Glyma1 |
| Gm_W82_CR19.G249630 | — | Gm_W82_CR19 |
| Contig9146 | — | cajanus_cajan |
| Chromosome 14 (LG O) | | |
| NS0116559 | — | — |
| Glyma10g33710 | — | Glyma1 |
| TA42233_3847 | — | Glycine_max_release_2 |
| AF108084.1 | — | GenBank |
| AW734581 | — | Glycine_max_release_2 |
| Glyma10g34260 | — | Glyma1 |
| Glyma10g34280 | — | Glyma1 |
| Glyma10g34290 | — | Glyma1 |
| Glyma10g34460 | — | Glyma1 |
| Glyma10g34600 | — | Glyma1 |
| Glyma10g34630 | — | Glyma1 |
| Glyma10g34850 | — | Glyma1 |
| NS0120070 | 24 | — |
| NS0097952 | 25 | — |
| NS0092960 | 26 | — |
| Glyma10g36370 | — | Glyma1 |
| NS0118907 | 27 | — |
| Glyma10g37560 | — | Glyma1 |
| TC354083 | — | GMGI.042210 |
| Glyma10g37600 | — | Glyma1 |
| BW595896 | — | LJGI.070108 |
| TC130824 | — | MTGI.071708 |
| CV528982 | — | Phaseolus_vulgaris |
| Glyma10g37610 | — | Glyma1 |
| BG511181 | — | GMGI.042210 |
| TA68568_3847 | — | Glycine_max_release_2 |
| NS0204740 | 28 | — |
| NS0205036 | 29 | — |
| Glyma10g37910 | — | Glyma1 |
| Glyma10g37920 | — | Glyma1 |
| Gm_W82_CR10.G221330 | — | Gm_W82_CR10 |
| NS0206252 | 30 | — |
| Glyma10g38600 | — | Glyma1 |
| Glyma10g40520 | — | Glyma1 |
| BF631841 | — | MTGI.071708 |
| Glyma10g41460 | — | Glyma1 |
| Glyma10g41470 | — | Glyma1 |
| TC412490 | — | GMGI.042210 |
| Gm_W82_CR10.G236520 | — | Gm_W82_CR10 |
| Chromosome 7 (LG M) | | |
| Gm_W82_CR07.G4950 | — | Gm_W82_CR07 |
| TC112538 | — | MTGI.071708 |
| Glyma07g03790 | — | Glyma1 |
| Gm_W82_CR07.G8460 | — | Gm_W82_CR07 |
| Glyma07g03800 | — | Glyma1 |
| Glyma07g03810 | — | Glyma1 |
| NS0202654 | 47 | — |
| NS0206351 | 48 | — |
| Glyma07g04470 | — | Glyma1 |
| Glyma07g04840 | — | Glyma1 |
| NS0202966 | 49 | — |
| Glyma07g05420 | — | Glyma1 |
| Glyma07g05820 | — | Glyma1 |
| NS0102362 | — | — |
| Glyma07g06150 | — | Glyma1 |
| Glyma07g06510 | — | Glyma1 |
| Glyma07g06560 | — | Glyma1 |
| Glyma07g07380 | — | Glyma1 |
| Gm_W82_CR07.G30600 | — | Gm_W82_CR07 |
| Pvcon9217 | — | Phaseolus_vulgaris |
| TC119399 | — | MTGI.071708 |
| Glyma07g07560 | — | Glyma1 |
| TC385708 | — | GMGI.042210 |
| Glyma07g08950 | — | Glyma1 |
| Glyma07g09110 | — | Glyma1 |
| Glyma07g09150 | — | Glyma1 |
| Glyma07g09160 | — | Glyma1 |
| Glyma07g09170 | — | Glyma1 |
| Glyma07g09900 | — | Glyma1 |
| Glyma07g09960 | — | Glyma1 |
| Glyma07g09970 | — | Glyma1 |
| NS0119842 | — | — |
| TA57919_3847 | — | Glycine_max_release_2 |
| Glyma07g11180 | — | Glyma1 |
| Glyma07g12210 | — | Glyma1 |
| Glyma07g29640 | — | Glyma1 |
| Glyma07g29650 | — | Glyma1 |
| Glyma07g29940 | — | Glyma1 |
| Glyma07g31380 | — | Glyma1 |
| Glyma07g31390 | — | Glyma1 |
| NS0202730 | 50 | — |
| NS0206314 | 51 | — |
| Glyma07g31610 | — | Glyma1 |
| Glyma07g32330 | — | Glyma1 |
| Glyma07g33070 | — | Glyma1 |
| Glyma07g33090 | — | Glyma1 |
| Glyma07g33560 | — | Glyma1 |

TABLE 14

| | | | | |
|---|---|---|---|---|
| Chromosome 18 (LG G) | | | | |
| Locus/DisplayName (1) | SEQ ID NO: (2) | Source (3) | Start Base (4) | End Base (5) |
| Gm_W82_CR18.G397200 | — | Gm_W82_CR18 | 59900386 | 59906556 |
| NGMAX008183850 | 52 | — | 59904411 | 59904712 |
| Contig19662 | — | cajanus_cajan | 59905905 | 59906118 |
| BARCSOYSSR_18_1832 | — | Wm82_potential_SSR | 60056533 | 60056556 |
| NGMAX008184740 | 53 | — | 60061647 | 60061948 |
| Pvcon7024 | — | Phaseolus_vulgaris | 60065999 | 60067897 |
| TA4278_3885 | — | Phaseolus_vulgaris_release_2 | 60245743 | 60247776 |
| NS0204945 | 54 | — | 60247182 | 60246514 |
| TC378862 | — | GMGI.042210 | 60247386 | 60247845 |
| Gm_W82_CR18.G400990 | — | Gm_W82_CR18 | 61248610 | 61249504 |
| NGMAX008190659 | 55 | — | 61262829 | 61263130 |

TABLE 14-continued

Chromosome 18 (LG G)

| Locus/DisplayName (1) | SEQ ID NO: (2) | Source (3) | Start Base (4) | End Base (5) |
|---|---|---|---|---|
| 304729__3194__1618 | — | cajanus_cajan | 61262926 | 61263150 |
| TC373110 | — | GMGI.042210 | 61315062 | 61315579 |
| NGMAX008190985 | 56 | — | 61322677 | 61322978 |
| BM108253 | — | Glycine_max_release_2 | 61329398 | 61329834 |
| BARCSOYSSR_18_1891 | — | Wm82_potential_SSR | 61385362 | 61385381 |
| NS0205638 | 57 | — | 61388179 | 61388758 |
| Cf2356d | — | Chafa1_1clean | 61388553 | 61388793 |
| TC373562 | — | GMGI.042210 | 61390489 | 61391050 |
| NGMAX008191317 | 58 | — | 61392011 | 61392312 |
| Cf18802d | — | Chafa1_1clean | 61392112 | 61392386 |
| NP7265835 | — | MTGI.071708 | 61430944 | 61432625 |
| NS0092671 | 59 | — | 61432518 | 61432769 |
| Glyma18g53050 | — | Glyma1 | 61434592 | 61439004 |
| NS0118292 | 60 | — | | |
| NGMAX008194551 | 61 | — | 61994075 | 61994376 |
| NGMAX008194952 | 62 | — | 62082932 | 62083233 |
| 108285__2293__0177 | — | cajanus_cajan | 62090438 | 62090654 |

TABLE 17

Chromosome 5 (LG A1)

| Locus/DisplayName (1) | SEQ ID NO: (2) | Source (3) | Start Base (4) | End Base (5) |
|---|---|---|---|---|
| WmFPC_Contig7872 | — | Wm82 | 8611032 | 8760634 |
| NGMAX006398059 | 71 | — | 8726001 | 8726302 |
| TA74988_3847 | — | Glycine_max_release_2 | 8726509 | 8728196 |
| TA11305_34305 | — | Lotus_japonicus_release_1 | 8726743 | 8728281 |
| Glyma05g08860 | — | Glyma1 | 8731333 | 8733792 |
| Gm_W82_CR05.G36010 | — | Gm_W82_CR05 | 8731333 | 8733792 |
| NGMAX006398075 | 72 | — | 8734373 | 8734674 |
| Glyma05g08870 | — | Glyma1 | 8749735 | 8751567 |
| TC412701 | — | GMGI.042210 | 8789875 | 8790358 |
| CV534998 | — | Phaseolus_vulgaris | 8790063 | 8790596 |
| BARCSOYSSR_05_0384 | — | Wm82_potential_SSR | 8791244 | 8791303 |
| NGMAX006398171 | 73 | — | 8792560 | 8792861 |
| Contig45244 | — | cajanus_cajan | 8793029 | 8793205 |
| Contig16193 | — | cajanus_cajan | 8793151 | 8793206 |
| Contig48186 | — | cajanus_cajan | 8972135 | 8973187 |
| AW278035 | — | Glycine_max_release_2 | 8972910 | 8973235 |
| NGMAX006398585 | 74 | — | 8975992 | 8976293 |
| 442533__3845__3611 | — | cajanus_cajan | 8977523 | 8977782 |
| TC414557 | — | GMGI.042210 | 8977562 | 8977758 |
| Cf7706d | — | Chafa1_1clean | 8999539 | 8999973 |
| Glyma05g09220 | — | Glyma1 | 8995921 | 9005129 |
| NGMAX006398641 | 75 | — | 9000470 | 9000771 |
| TC416067 | — | GMGI.042210 | 9000945 | 9001313 |
| Glyma05g09240 | — | Glyma1 | 9010402 | 9011072 |
| Gm_W82_CR05.G38570 | — | Gm_W82_CR05 | 9010402 | 9011072 |
| 169777__3462__2392 | — | cajanus_cajan | 9010970 | 9011057 |
| NGMAX006398662 | 76 | — | 9012813 | 9013114 |
| Cf3250d | — | Chafa1_1clean | 9012500 | 9015254 |
| Glyma05g09250 | — | Glyma1 | 9014291 | 9015254 |
| Gm_W82_CR05.G38580 | — | Gm_W82_CR05 | 9014291 | 9015254 |
| BP044357 | — | Lotus_japonicus_release_1 | 9026484 | 9028268 |
| AV764725 | — | Lotus_japonicus_release_1 | 9026611 | 9028149 |
| CB540591 | — | Phaseolus_vulgaris | 9026676 | 9028170 |
| NGMAX006398682 | 77 | — | 9029664 | 9029965 |
| Contig40310 | — | cajanus_cajan | 9032015 | 9032233 |
| Contig32764 | — | cajanus_cajan | 9032145 | 9032358 |
| Glyma05g09320 | — | Glyma1 | 9048193 | 9049361 |
| Gm_W82_CR05.G38650 | — | Gm_W82_CR05 | 9048193 | 9049361 |
| NGMAX006398725 | 78 | — | 9049111 | 9049412 |
| NGMAX006398726 | 79 | — | 9049326 | 9049627 |
| Contig42115 | — | cajanus_cajan | 9049922 | 9050265 |
| Gm_W82_CR05.G38690 | — | Gm_W82_CR05 | 9091842 | 9095724 |
| NGMAX006398800 | 80 | — | 9096884 | 9097185 |
| Cf13029d | — | Chafa1_1clean | 9097111 | 9097317 |
| BARC-044481-08709 | — | marker_map4 | 9097066 | 9097473 |

TABLE 17-continued

Chromosome 5 (LG A1)

| Locus/DisplayName (1) | SEQ ID NO: (2) | Source (3) | Start Base (4) | End Base (5) |
|---|---|---|---|---|
| BM568328 | — | Glycine_soja_release_2 | 9231822 | 9232150 |
| NGMAX006398923 | 82 | — | 9314174 | 9314475 |
| Glyma05g09450 | — | Glyma1 | 9314231 | 9314482 |
| gi_251741293 | — | cajanus_cajan | 9957719 | 9957766 |
| NGMAX006399042 | 83 | — | 9964942 | 9965243 |
| Glyma05g10000 | — | Glyma1 | 9966305 | 9967626 |
| Cf16969d | — | Chafa1_1clean | 10085119 | 10088679 |
| NGMAX006399063 | 84 | — | 10105515 | 10105816 |
| BARCSOYSSR_05_0410 | — | Wm82_potential_SSR | 10110781 | 10110830 |
| Gm_W82_CR05.G41210 | — | Gm_W82_CR05 | 10127470 | 10128074 |
| NGMAX006399066 | 85 | — | 10128574 | 10128875 |
| BW597367 | — | LJGI.070108 | 10132125 | 10132681 |
| BARCSOYSSR_05_0420 | — | Wm82_potential_SSR | 10747843 | 10747892 |
| NGMAX006399168 | 86 | — | 10753693 | 10753994 |
| 138369_1624_0039 | — | cajanus_cajan | 10754650 | 10754859 |
| 033583_0211_2302 | — | cajanus_cajan | 12671045 | 12671171 |
| BARCSOYSSR_05_0445 | — | Wm82_potential_SSR | 12706029 | 12706048 |
| NGMAX006399482 | 87 | — | 12716333 | 12716634 |
| Glyma05g12510 | — | Glyma1 | 12744996 | 12745160 |
| Gm_W82_CR05.G105990 | — | Gm_W82_CR05 | 17286974 | 17287535 |
| BARCSOYSSR_05_0506 | — | Wm82_potential_SSR | 17292930 | 17292983 |
| NGMAX006400296 | 88 | — | 17294665 | 17294966 |
| Glyma05g15680 | — | Glyma1 | 17305698 | 17305960 |
| Contig15035 | — | cajanus_cajan | 21200771 | 21201057 |
| NGMAX006401034 | 89 | — | 21201143 | 21201444 |
| 199534_3796_0358 | — | cajanus_cajan | 21201471 | 21201711 |
| 152322_2470_3960 | — | cajanus_cajan | 22915341 | 22915534 |
| BARCSOYSSR_05_0564 | — | Wm82_potential_SSR | 22945692 | 22945743 |
| NGMAX006401429 | 90 | — | 23025046 | 23025347 |
| TC368157 | — | GMGI.042210 | 23027973 | 23029620 |
| Satt454 | — | marker_map4 | 25287587 | 25287839 |
| BARCSOYSSR_05_0609 | — | Wm82_potential_SSR | 25287731 | 25287781 |
| NGMAX006401765 | 91 | — | 25295318 | 25295619 |
| 381902_3512_4031 | — | cajanus_cajan | 25296404 | 25296662 |
| Glyma05g21200 | — | Glyma1 | 25627653 | 25634422 |
| Gm_W82_CR05.G152350 | — | Gm_W82_CR05 | 25627653 | 25634422 |
| NGMAX008341472 | 92 | — | 25645423 | 25645724 |
| BARCSOYSSR_05_0622 | — | Wm82_potential_SSR | 25648451 | 25648492 |
| Cf5490d | — | Chafa1_1clean | 26166473 | 26166936 |
| 318062_1525_0472 | — | cajanus_cajan | 26170236 | 26170357 |
| NGMAX006401896 | 93 | — | 26170363 | 26170664 |
| BARCSOYSSR_05_0638 | — | Wm82_potential_SSR | 26175536 | 26175569 |
| BARCSOYSSR_05_0639 | — | Wm82_potential_SSR | 26175838 | 26175889 |
| BARCSOYSSR_05_0640 | — | Wm82_potential_SSR | 26176422 | 26176471 |

TABLE 20

Chromosome 7 (LG M)

| Locus/DisplayName (1) | SEQ ID NO: (2) | Source (3) | Start Base (4) | End Base (5) |
|---|---|---|---|---|
| NGMAX006621532 | 94 | — | 3393031 | 3393332 |
| Glyma07g04610 | — | Glyma1 | 3402388 | 3404721 |
| Gm_W82_CR07.G10270 | — | Gm_W82_CR07 | 3402388 | 3404721 |
| TC403215 | — | GMGI.042210 | 3412126 | 3412400 |
| Glyma07g04620 | — | Glyma1 | 3412764 | 3413309 |
| NGMAX006621610 | 95 | — | 3416548 | 3416849 |
| BARCSOYSSR_07_0185 | — | Wm82_potential_SSR | 3417142 | 3417201 |
| NGMAX006621674 | 96 | — | 3427338 | 3427639 |
| BARCSOYSSR_07_0186 | — | Wm82_potential_SSR | 3429880 | 3429909 |
| Contig7081 | — | cajanus_cajan | 3430111 | 3430277 |
| ss181360748 | — | Wm82xPI468916 | 3433852 | 3433973 |
| NGMAX006621699 | 97 | — | 3440093 | 3440394 |
| AW720220 | — | LJGI.070108 | 3441581 | 3444258 |
| BM525303 | — | Glycine_soja_release_2 | 3441548 | 3444605 |
| 112768_3355_0899 | — | cajanus_cajan | 3444787 | 3445772 |
| 213668_2891_0626 | — | cajanus_cajan | 3445730 | 3446583 |
| NGMAX006621706 | 98 | — | 3446258 | 3446559 |
| Contig9107 | — | cajanus_cajan | 3444989 | 3447842 |

TABLE 20-continued

Chromosome 7 (LG M)

| Locus/DisplayName (1) | SEQ ID NO: (2) | Source (3) | Start Base (4) | End Base (5) |
|---|---|---|---|---|
| TA5004_3885 | — | Phaseolus_vulgaris_release_2 | 3446499 | 3448009 |
| Glyma07g04800 | — | Glyma1 | 3540566 | 3542258 |
| Gm_W82_CR07.G10660 | — | Gm_W82_CR07 | 3540566 | 3542258 |
| NGMAX006621720 | 99 | — | 3541479 | 3541780 |
| TC396277 | — | GMGI.042210 | 3542083 | 3542437 |
| TA49177_3847 | — | Glycine_max_release_2 | 3541831 | 3543402 |
| ss181360746 | — | Wm82xPI468916 | 3543470 | 3543591 |
| BARCSOYSSR_07_0190 | — | Wm82_potential_SSR | 3545904 | 3545967 |
| NGMAX006621726 | 100 | — | 3547188 | 3547489 |
| BF597028 | — | Glycine_soja_release_2 | 3551690 | 3552575 |
| BG043289 | — | Glycine_max_release_2 | 3663176 | 3665198 |
| TA2947_3886 | — | Phaseolus_coccineus_release_2 | 3663077 | 3665376 |
| AI443806 | — | Glycine_max_release_2 | 3664939 | 3665318 |
| Contig38368 | — | cajanus_cajan | 3664966 | 3665337 |
| NGMAX006621767 | 101 | — | 3679813 | 3680114 |
| NGMAX006621777 | 102 | — | 3682741 | 3683042 |
| BARC-041667-08063 | — | marker_map4 | 3683493 | 3683694 |
| 393760_2699_3151 | — | cajanus_cajan | 3809484 | 3809711 |
| FK446225 | — | GMGI.042210 | 3812085 | 3812372 |
| WmFPC_Contig66 | — | Wm82 | 3706750 | 3925221 |
| NGMAX006622006 | 103 | — | 3816276 | 3816577 |
| Contig45160 | — | cajanus_cajan | 3816479 | 3817114 |
| TA40883_3847 | — | Glycine_max_release_2 | 3816485 | 3817194 |
| TC375163 | — | GMGI.042210 | 3979825 | 3980713 |
| Contig13143 | — | cajanus_cajan | 3980387 | 3980595 |
| BARCSOYSSR_07_0207 | — | Wm82_potential_SSR | 3981130 | 3981165 |
| NGMAX006622614 | 104 | — | 3981054 | 3981355 |
| BARCSOYSSR_07_0208 | — | Wm82_potential_SSR | 3988651 | 3988670 |
| Glyma07g05350 | — | Glyma1 | 3988721 | 3990122 |
| BI969369 | — | Glycine_max_release_2 | 4122488 | 4124632 |
| TC367324 | — | GMGI.042210 | 4124193 | 4124669 |
| NGMAX006622952 | 105 | — | 4126322 | 4126623 |
| CD395608 | — | Glycine_max_release_2 | 4126664 | 4126991 |
| TC387188 | — | GMGI.042210 | 4849393 | 4849841 |
| NGMAX006623558 | 106 | — | 4850240 | 4850541 |
| TA12767_34305 | — | Lotus_japonicus_release_1 | 4854998 | 4857901 |
| TA47785_3847 | — | Glycine_max_release_2 | 5034853 | 5036117 |
| asmbl_4174 | — | Vigna_unguiculata | 5034852 | 5036125 |
| NGMAX006623995 | 107 | — | 5035388 | 5035689 |
| 259614_3432_2478 | — | cajanus_cajan | 5035714 | 5035850 |
| Glyma07g06360 | — | Glyma1 | 5084793 | 5084902 |
| BARCSOYSSR_07_0271 | — | Wm82_potential_SSR | 5089392 | 5089423 |
| NGMAX006624271 | 108 | — | 5092982 | 5093283 |
| Contig23159 | — | cajanus_cajan | 5094525 | 5094763 |
| Pvcon10792 | — | Phaseolus_vulgaris | 5418127 | 5418733 |
| 315592_2632_1694 | — | cajanus_cajan | 5418473 | 5418717 |
| NGMAX006625883 | 109 | — | 5418776 | 5419077 |
| Contig24687 | — | cajanus_cajan | 5419388 | 5419599 |
| Cf18742d | — | Chafa1_1clean | 5455985 | 5459507 |
| NGMAX006626085 | 110 | — | 5457696 | 5457997 |
| TC381430 | — | GMGI.042210 | 5457600 | 5459580 |
| BI785468 | — | Glycine_max_release_2 | 5457683 | 5459525 |
| TA53357_3847 | — | Glycine_max_release_2 | 5457605 | 5460346 |
| FE709341 | — | Phaseolus_vulgaris | 5458490 | 5459666 |

TABLE 23

Chromosome 17 (LG D2)

| Locus/DisplayName (1) | SEQ ID NO: (2) | Source (3) | Start Base (4) | End Base (5) |
|---|---|---|---|---|
| NGMAX007790014 | 115 | — | 3155696 | 3155997 |
| BF425454 | — | GMGI.042210 | 3155653 | 3156074 |
| BF425454 | — | Glycine_max_release_2 | 3155653 | 3156123 |
| Cf14786d | — | Chafa1_1clean | 3323205 | 3323429 |
| BG511404 | — | Glycine_max_release_2 | 3323134 | 3323620 |
| 105562_1346_1630 | — | cajanus_cajan | 3323270 | 3323498 |
| Contig39552 | — | cajanus_cajan | 3323309 | 3323550 |

TABLE 23-continued

Chromosome 17 (LG D2)

| Locus/DisplayName (1) | SEQ ID NO: (2) | Source (3) | Start Base (4) | End Base (5) |
|---|---|---|---|---|
| NGMAX007790381 | 116 | — | 3323744 | 3324045 |
| Cf17659d | — | Chafa1_1clean | 3320738 | 3328482 |
| Contig37026 | — | cajanus_cajan | 3326324 | 3326599 |
| Contig3555 | — | cajanus_cajan | 3326889 | 3327061 |
| CA908533 | — | Phaseolus_coccineus_release_2 | 3326779 | 3327187 |
| Glyma17g04950 | — | Glyma1 | 3326774 | 3328781 |
| Gm_W82_CR17.G16430 | — | Gm_W82_CR17 | 3326774 | 3328781 |
| NGMAX007790411 | 117 | — | 3329853 | 3330154 |
| Glyma17g04960 | — | Glyma1 | 3330115 | 3332472 |
| Gm_W82_CR17.G16440 | — | Gm_W82_CR17 | 3329999 | 3332810 |
| Contig24276 | — | cajanus_cajan | 3331849 | 3332089 |
| 125135_2424_0556 | — | cajanus_cajan | 3360193 | 3360344 |
| NGMAX007790440 | 118 | — | 3364343 | 3364644 |
| Cf16374d | — | Chafa1_1clean | 3365597 | 3366588 |
| BG838973 | — | Glycine_max_release_2 | 3365233 | 3367059 |
| BG507731 | — | GMGI.042210 | 3611762 | 3612075 |
| BARCSOYSSR_17_0195 | — | Wm82_potential_SSR | 3633036 | 3633099 |
| NGMAX007790913 | 120 | — | 3633675 | 3633976 |
| BW655748 | — | GMGI.042210 | 3635257 | 3636145 |
| Cf18958d | — | Chafa1_1clean | 3636566 | 3636904 |
| BARCSOYSSR_17_0196 | — | Wm82_potential_SSR | 3644289 | 3644308 |
| NGMAX007790961 | 121 | — | 3647410 | 3647711 |
| BG405534 | — | Glycine_max_release_2 | 3654628 | 3655142 |
| Cf13064d | — | Chafa1_1clean | 3655848 | 3655983 |
| Contig31396 | — | cajanus_cajan | 3655888 | 3656111 |
| NGMAX007790982 | 122 | — | 3656282 | 3656583 |
| Glyma17g05300 | — | Glyma1 | 3657812 | 3658198 |
| BARCSOYSSR_17_0197 | — | Wm82_potential_SSR | 3659872 | 3659903 |
| 085726_2424_0132 | — | cajanus_cajan | 4982475 | 4985016 |
| NGMAX007793044 | 123 | — | 4984466 | 4984767 |
| BARCSOYSSR_17_0274 | — | Wm82_potential_SSR | 4996872 | 4996919 |
| 086788_3391_0381 | — | cajanus_cajan | 4998989 | 4999064 |

TABLE 26

Chromosome 19 (LG L)

| Locus/DisplayName (1) | SEQ ID NO: (2) | Source (3) | Start Base (4) | End Base (5) |
|---|---|---|---|---|
| NGMAX008199658 | 124 | — | 1253726 | 1254027 |
| Cf21314d | — | Chafa1_1clean | 1254120 | 1255988 |
| Gm_W82_CR19.G10090 | — | Gm_W82_CR19 | 1271256 | 1272512 |
| NGMAX008199750 | 125 | — | 1272430 | 1272731 |
| BARCSOYSSR_19_0086 | — | Wm82_potential_SSR | 1272601 | 1272664 |
| WmFPC_Contig3730 | — | Wm82 | 1163579 | 1429575 |
| NGMAX008199864 | 126 | — | 1296447 | 1296748 |
| BARCSOYSSR_19_0088 | — | Wm82_potential_SSR | 1297586 | 1297645 |
| BARCSOYSSR_19_0089 | — | Wm82_potential_SSR | 1308871 | 1308956 |
| NGMAX008199973 | 127 | — | 1309280 | 1309581 |
| Glyma19g01720 | — | Glyma1 | 1309198 | 1310096 |
| Glyma19g01750 | — | Glyma1 | 1333537 | 1333700 |
| NGMAX008200015 | 128 | — | 1333772 | 1334073 |
| BARCSOYSSR_19_0092 | — | Wm82_potential_SSR | 1334292 | 1334333 |
| NGMAX008200022 | 129 | — | 1337736 | 1338037 |
| Gm_W82_CR19.G10370 | — | Gm_W82_CR19 | 1343268 | 1344198 |
| BI967966 | — | Glycine_max_release_2 | 1387373 | 1388013 |
| NGMAX008200044 | 130 | — | 1392143 | 1392444 |
| Contig37264 | — | cajanus_cajan | 1396218 | 1396421 |
| Glyma19g01820 | — | Glyma1 | 1396249 | 1396497 |
| NGMAX008200052 | 131 | — | 1414026 | 1414327 |
| BI321279 | — | GMGI.042210 | 1416432 | 1416851 |
| BG511671 | — | Glycine_max_release_2 | 1489429 | 1489735 |
| NGMAX008200275 | 132 | — | 1490445 | 1490746 |
| Glyma19g01870 | — | Glyma1 | 1492838 | 1495764 |
| Gm_W82_CR19.G15280 | — | Gm_W82_CR19 | 1492838 | 1495764 |
| Cf9954d | — | Chafa1_1clean | 1501094 | 1501508 |
| Glyma19g01880 | — | Glyma1 | 1499643 | 1504582 |
| Gm_W82_CR19.G15290 | — | Gm_W82_CR19 | 1499643 | 1504595 |
| NGMAX008200335 | 133 | — | 1502499 | 1502800 |

TABLE 26-continued

Chromosome 19 (LG L)

| Locus/DisplayName (1) | SEQ ID NO: (2) | Source (3) | Start Base (4) | End Base (5) |
|---|---|---|---|---|
| ss181360588 | — | Wm82xPI468916 | 1502646 | 1502767 |
| BARCSOYSSR_19_0099 | — | Wm82_potential_SSR | 1509013 | 1509038 |
| BARCSOYSSR_19_0100 | — | Wm82_potential_SSR | 1526039 | 1526136 |
| Contig11069 | — | cajanus_cajan | 1592437 | 1592670 |
| Contig3143 | — | cajanus_cajan | 1592554 | 1592758 |
| 268933_0047_1009 | — | cajanus_cajan | 1592619 | 1592881 |
| NGMAX008200568 | 134 | — | 1592869 | 1593170 |
| BARCSOYSSR_19_0105 | — | Wm82_potential_SSR | 1593154 | 1593203 |
| Contig1379 | — | cajanus_cajan | 1593217 | 1593635 |
| Contig48254 | — | cajanus_cajan | 1593271 | 1593819 |
| 285107_3537_3801 | — | cajanus_cajan | 1593451 | 1593714 |
| BARCSOYSSR_19_0106 | — | Wm82_potential_SSR | 1596261 | 1596300 |
| BARCSOYSSR_19_0107 | — | Wm82_potential_SSR | 1599519 | 1599558 |
| 071040_1554_2187 | — | cajanus_cajan | 1610939 | 1610980 |
| NGMAX008200652 | 135 | — | 1615160 | 1615461 |
| BARCSOYSSR_19_0108 | — | Wm82_potential_SSR | 1615763 | 1615782 |
| NGMAX008200656 | 136 | — | 1617406 | 1617707 |
| BARCSOYSSR_19_0109 | — | Wm82_potential_SSR | 1630429 | 1630452 |
| Satt446 | — | marker_map4 | 1634051 | 1634348 |
| Contig11069 | — | cajanus_cajan | 1651156 | 1651389 |
| Contig3143 | — | cajanus_cajan | 1651273 | 1651470 |
| NGMAX008200785 | 137 | — | 1651276 | 1651577 |
| 268933_0047_1009 | — | cajanus_cajan | 1651338 | 1651604 |
| Contig1379 | — | cajanus_cajan | 1651725 | 1652180 |
| Cf17202d | — | Chafa1_1clean | 1809590 | 1809811 |
| TC413656 | — | GMGI.042210 | 1810134 | 1810736 |
| NGMAX008200913 | 138 | — | 1813813 | 1814114 |
| 354114_3517_2150 | — | cajanus_cajan | 1815145 | 1815383 |
| TC409049 | — | GMGI.042210 | 1817061 | 1817307 |
| BI970322 | — | Glycine_max_release_2 | 7063345 | 7064079 |
| Contig8569 | — | cajanus_cajan | 44569360 | 44571272 |
| CB540932 | — | Phaseolus_vulgaris | 44569015 | 44571911 |

TABLE 29

Chromosome 9 (LG K)

| Locus/DisplayName (1) | SEQ ID NO: (2) | Source (3) | Start Base (4) | End Base (5) |
|---|---|---|---|---|
| NGMAX006925911 | 139 | — | 40243718 | 40244019 |
| Contig41696_primers | — | cajanus_cajan | 40257234 | 40257429 |
| Contig41696 | — | cajanus_cajan | 40256966 | 40258176 |
| BM108278 | — | Glycine_max_release_2 | 40257091 | 40258183 |
| Contig31037 | — | cajanus_cajan | 40258700 | 40259448 |
| asmbl_6000 | — | Vigna_unguiculata | 40258719 | 40259446 |
| BE823853 | — | Glycine_max_release_2 | 40258861 | 40259409 |
| NGMAX006925967 | 140 | — | 40259790 | 40260091 |
| NGMAX006926063 | 141 | — | 40272402 | 40272703 |
| BARCSOYSSR_09_1351 | — | Wm82_potential_SSR | 40274616 | 40274639 |
| Cf13555d | — | Chafa1_1clean | 40276310 | 40276615 |
| NGMAX006926228 | 142 | — | 40308770 | 40309071 |
| TC361317 | — | GMGI.042210 | 40312128 | 40312691 |
| TA56123_3847 | — | Glycine_max_release_2 | 40312116 | 40312852 |
| 218500_2738_3544 | — | cajanus_cajan | 40312576 | 40312893 |
| NGMAX006926426 | 143 | — | 40374697 | 40374998 |
| BM307669 | — | Glycine_max_release_2 | 40376529 | 40376938 |
| 351740_2368_1082 | — | cajanus_cajan | 40376719 | 40376915 |
| Cf15642d | — | Chafa1_1clean | 40376761 | 40376927 |
| BARCSOYSSR_09_1359 | — | Wm82_potential_SSR | 40378752 | 40378773 |
| BU080803 | — | Glycine_max_release_2 | 40378097 | 40380883 |
| NGMAX006926451 | 144 | — | 40381147 | 40381448 |
| 117697_1117_1653 | — | cajanus_cajan | 40385920 | 40386138 |
| Contig915 | — | cajanus_cajan | 40387459 | 40387654 |
| CA921370 | — | MTGI.071708 | 40448774 | 40449433 |
| Glyma09g34010 | — | Glyma1 | 40448819 | 40451396 |
| NGMAX006926709 | 145 | — | 40450053 | 40450354 |
| BI320313 | — | GMGI.042210 | 40466800 | 40466933 |
| NGMAX006926784 | 146 | — | 40492973 | 40493274 |
| Pvcon5634 | — | Phaseolus_vulgaris | 40493627 | 40494016 |

TABLE 29-continued

Chromosome 9 (LG K)

| Locus/DisplayName (1) | SEQ ID NO: (2) | Source (3) | Start Base (4) | End Base (5) |
|---|---|---|---|---|
| BP054761 | — | Lotus_japonicus_release_1 | 40493628 | 40494077 |
| BM892455 | — | GMGI.042210 | 40538148 | 40539515 |
| NGMAX006926934 | 147 | — | 40538904 | 40539205 |
| BM892455 | — | Glycine_max_release_2 | 40538148 | 40540469 |
| BU545056 | — | Glycine_max_release_2 | 40547146 | 40548442 |
| NGMAX006926989 | 148 | — | 40548839 | 40549140 |
| TA75773_3847 | — | Glycine_max_release_2 | 40565516 | 40566166 |
| TC356190 | — | GMGI.042210 | 40565516 | 40566166 |
| NGMAX006927044 | 149 | — | 40567379 | 40567680 |
| Contig25820 | — | cajanus_cajan | 40571216 | 40571379 |
| Contig4437 | — | cajanus_cajan | 40571319 | 40571422 |
| 008498_0634_0728 | — | cajanus_cajan | 40571401 | 40571432 |
| NGMAX006927083 | 150 | — | 40573731 | 40574032 |
| BARCSOYSSR_09_1372 | — | Wm82_potential_SSR | 40575734 | 40575771 |
| 368088_3993_0858 | — | cajanus_cajan | 40577562 | 40577807 |
| Glyma09g34170 | — | Glyma1 | 40606183 | 40615020 |
| Cf16214d | — | Chafa1_1clean | 40606988 | 40614651 |
| NGMAX006927293 | 151 | — | 40611728 | 40612029 |
| BU494285 | — | Lotus_japonicus_release_1 | 40610299 | 40613740 |
| BU494285 | — | LJGI.070108 | 40610302 | 40613740 |
| Glyma09g34190 | — | Glyma1 | 40633379 | 40638472 |
| NGMAX006927454 | 152 | — | 40636773 | 40637074 |
| TC413502 | — | GMGI.042210 | 40637328 | 40637485 |
| TA74376_3847 | — | Glycine_max_release_2 | 40660591 | 40660742 |
| TC410021 | — | GMGI.042210 | 40660591 | 40660742 |
| NGMAX006927578 | 153 | — | 40660778 | 40661079 |
| TC362522 | — | GMGI.042210 | 40660852 | 40662410 |
| TA49669_3847 | — | Glycine_max_release_2 | 40660954 | 40662419 |
| NS0094370 | 154 | — | | |
| 357928_2669_2557 | — | cajanus_cajan | 40663765 | 40664577 |
| TA3851_3886 | — | Phaseolus_coccineus_release_2 | 40663773 | 40664903 |
| TC404180 | — | GMGI.042210 | 40663478 | 40665282 |
| asmbl_6018 | — | Vigna_unguiculata | 40663844 | 40665198 |
| AI495278 | — | Glycine_max_release_2 | 40664775 | 40665263 |
| NS0202727 | 155 | — | 40667193 | 40666794 |
| 441702_2628_0479 | — | cajanus_cajan | 40667116 | 40667212 |
| Contig27394 | — | cajanus_cajan | 40667116 | 40667212 |
| BI424714 | — | Glycine_max_release_2 | 40667593 | 40668779 |
| BI424714 | — | GMGI.042210 | 40667677 | 40668779 |
| BI893945 | — | Glycine_max_release_2 | 40677514 | 40677927 |
| ss181358282 | — | Wm82xPI468916 | 40679987 | 40680108 |
| NGMAX006927737 | 156 | — | 40681901 | 40682202 |
| TC396512 | — | GMGI.042210 | 40682388 | 40685072 |
| Glyma09g34250 | — | Glyma1 | 40682388 | 40685488 |
| TC368672 | — | GMGI.042210 | 40682923 | 40685164 |
| Gm_W82_CR09.G172960 | — | Gm_W82_CR09 | 40682388 | 40685746 |
| BARCSOYSSR_09_1385 | — | Wm82_potential_SSR | 40692420 | 40692461 |
| NGMAX006927783 | 157 | — | 40693382 | 40693683 |
| Glyma09g34260 | — | Glyma1 | 40693196 | 40695274 |
| Gm_W82_CR09.G172970 | — | Gm_W82_CR09 | 40693196 | 40695274 |
| BARCSOYSSR_09_1386 | — | Wm82_potential_SSR | 40695711 | 40695732 |
| 310291_2136_0449 | — | cajanus_cajan | 40699187 | 40699273 |
| Contig29803 | — | cajanus_cajan | 40699810 | 40700422 |
| NGMAX006927836 | 158 | — | 40700573 | 40700874 |
| 221522_3792_2185 | — | cajanus_cajan | 40701635 | 40701833 |
| 113453_3824_1247 | — | cajanus_cajan | 40701634 | 40701848 |
| FE697104 | — | Phaseolus_vulgaris | 40701670 | 40702507 |
| Glyma09g34320 | — | Glyma1 | 40735795 | 40736472 |
| BARCSOYSSR_09_1388 | — | Wm82_potential_SSR | 40737394 | 40737419 |
| NGMAX006928046 | 159 | — | 40738085 | 40738386 |
| asmbl_6023 | — | Vigna_unguiculata | 40738466 | 40741661 |
| TA12621_34305 | — | Lotus_japonicus_release_1 | 40757487 | 40758228 |
| TC35672 | — | LJGI.070108 | 40757487 | 40758228 |
| NS0123372 | 160 | — | 40757850 | 40758506 |
| 339112_3138_3869 | — | cajanus_cajan | 40758893 | 40759121 |
| 381244_3433_2042 | — | cajanus_cajan | 40759267 | 40759490 |
| 074045_1887_1079 | — | cajanus_cajan | 40765413 | 40765510 |
| 200842_1421_3709 | — | cajanus_cajan | 40765605 | 40765747 |
| NGMAX006928148 | 161 | — | 40771660 | 40771761 |
| TC389778 | — | GMGI.042210 | 40772519 | 40773261 |
| TA44560_3847 | — | Glycine_max_release_2 | 40772519 | 40773559 |
| FE709357 | — | Phaseolus_vulgaris | 40775661 | 40776891 |
| Contig34874 | — | cajanus_cajan | 40776637 | 40776916 |
| NGMAX006928238 | 162 | — | 40780407 | 40780708 |

TABLE 29-continued

| Chromosome 9 (LG K) | | | | |
|---|---|---|---|---|
| Locus/DisplayName (1) | SEQ ID NO: (2) | Source (3) | Start Base (4) | End Base (5) |
| Contig39370 | — | cajanus_cajan | 40781564 | 40783018 |
| asmbl_6024 | — | Vigna_unguiculata | 40786818 | 40787111 |
| Contig6058 | — | cajanus_cajan | 40787205 | 40787407 |
| NGMAX006928269 | 163 | — | 40790581 | 40790882 |
| TA44261_3847 | — | Glycine_max_release_2 | 40791854 | 40792498 |
| BE801808 | — | Glycine_max_release_2 | 40791923 | 40792444 |
| Cf4870d | — | Chafa1_1clean | 40806197 | 40806526 |
| FK576691 | — | GMGI.042210 | 40806485 | 40806679 |
| NGMAX006928358 | 164 | — | 40808949 | 40809250 |
| Glyma09g34430 | — | Glyma1 | 40809022 | 40811799 |
| Gm_W82_CR09.G173740 | — | Gm_W82_CR09 | 40809022 | 40811799 |
| BARC-059665-15981 | — | marker_map4 | 40827693 | 40828086 |
| NGMAX006928507 | 165 | — | 40834823 | 40835124 |
| Gm_W82_CR09.G173770 | — | Gm_W82_CR09 | 40839879 | 40843063 |
| Glyma09g34460 | — | Glyma1 | 40840286 | 40843063 |
| NGMAX006928537 | 166 | — | 40841840 | 40842141 |
| TA70211_3847 | — | Glycine_max_release_2 | 40841283 | 40843007 |
| TC349093 | — | GMGI.042210 | 40841283 | 40843007 |
| FE702368 | — | Phaseolus_vulgaris | 40884481 | 40886140 |
| AM162189 | — | Pisum_sativum_release_2 | 40885122 | 40885709 |
| NGMAX006928614 | 167 | — | 40887274 | 40887575 |
| BM139756 | — | Glycine_max_release_2 | 40887540 | 40887691 |
| DW246746 | — | Glycine_max_release_2 | 40887692 | 40887860 |
| 271518_0250_0536 | — | cajanus_cajan | 40898791 | 40898892 |
| 139280_1004_2213 | — | cajanus_cajan | 40898807 | 40898893 |
| NGMAX006928650 | 168 | — | 40901958 | 40902259 |
| 315453_0615_0207 | — | cajanus_cajan | 40909988 | 40910230 |
| TC391225 | — | GMGI.042210 | 40909479 | 40910839 |
| Glyma09g34540 | — | Glyma1 | 40915819 | 40917570 |
| 135326_1839_1598 | — | cajanus_cajan | 40919347 | 40919571 |
| NGMAX006928755 | 169 | — | 40919514 | 40919815 |
| CD418184 | — | Glycine_max_release_2 | 40919571 | 40920074 |
| NS0202939 | 170 | — | | |
| Glyma09g34560 | — | Glyma1 | 40925986 | 40926726 |
| Pvcon4656 | — | Phaseolus_vulgaris | 40926434 | 40929444 |
| NS0119073 | 171 | — | 40927939 | 40928620 |
| BM309243 | — | GMGI.042210 | 40928556 | 40928983 |
| 230306_1435_0813 | — | cajanus_cajan | 40928906 | 40929123 |
| Cf15892d | — | Chafa1_1clean | 40932401 | 40932559 |
| Glyma09g34580 | — | Glyma1 | 40932359 | 40933733 |
| Gm_W82_CR09.G174470 | — | Gm_W82_CR09 | 40932359 | 40933733 |
| NGMAX006928836 | 172 | — | 40933766 | 40934067 |
| Glyma09g34590 | — | Glyma1 | 40933583 | 40935779 |
| AW781873 | — | Glycine_max_release_2 | 40934635 | 40935110 |
| AI900149 | — | Glycine_max_release_2 | 40934700 | 40935424 |
| TC368843 | — | GMGI.042210 | 40934635 | 40935779 |
| TA55686_3847 | — | Glycine_max_release_2 | 40934761 | 40935778 |
| NS0202984 | 173 | — | 40935137 | 40935465 |
| CD394340 | — | Glycine_max_release_2 | 40935262 | 40935757 |
| BARCSOYSSR_09_1395 | — | Wm82_potential_SSR | 40938697 | 40938724 |
| BARCSOYSSR_09_1396 | — | Wm82_potential_SSR | 40941652 | 40941677 |
| NGMAX006928848 | 174 | — | 40944266 | 40944567 |
| Cf5524d | — | Chafa1_1clean | 40948145 | 40948510 |
| Glyma09g34600 | — | Glyma1 | 40947262 | 40950520 |
| FE711739 | — | Phaseolus_vulgaris | 40948145 | 40949768 |

What is claimed is:

1. A method of producing a population of soybean plants that comprises a genotype associated with a low iron growth condition tolerant phenotype, the method comprising:

i) genotyping a first population of soybean plants, wherein the first population contains at least one allele associated with the low iron growth condition tolerant phenotype, wherein the allele is located on linkage group A1 within 500 kb telomere proximal or 500 kb centromere proximal of the nucleic acid marker of SEQ ID NO: 77;

ii) selecting from said first population of soybean plants based upon said genotyping one or more soybean plants comprising the at least one allele associated with a low iron growth condition tolerant phenotype; and iii) producing offspring from the one or more selected soybean plants of the first population of soybean plants, thereby producing a second population of soybean plants comprising a genotype associated with a low iron growth condition tolerant phenotype, wherein at least one plant of the second population of soybean plants is assayed to determine if it exhibits a low iron growth condition tolerant phenotype.

2. The method of claim 1, wherein said selected plant exhibits a low iron growth condition tolerant phenotype.

3. The method of claim 1, wherein said genotype associated with a low iron growth condition tolerant phenotype comprises at least one allele associated with a low iron growth condition tolerant phenotype of one or more markers selected from the group consisting of SEQ ID NO: 71, SEQ ID NO: 72, SEQ ID NO: 73, SEQ ID NO: 74, SEQ ID NO: 75, SEQ ID NO: 76, SEQ ID NO: 77, SEQ ID NO: 78, SEQ ID NO: 79, SEQ ID NO: 80, and SEQ ID NO: 81.

4. The method of claim 3, wherein said selected plant exhibits a low iron growth condition tolerant phenotype.

* * * * *